(12) United States Patent
Gambhir et al.

(10) Patent No.: US 7,834,148 B2
(45) Date of Patent: Nov. 16, 2010

(54) PROTEIN PHOSPHORYLATION IMAGING SYSTEMS, METHODS OF MAKING PHOSPHORYLATION IMAGING SYSTEMS, AND METHODS OF USE THEREOF

(75) Inventors: Sanjiv S. Gambhir, Portola Valley, CA (US); Ramasamy Paulmurugan, Mountain View, CA (US)

(73) Assignee: Stanford University, Palo Alto, CA (US)

( * ) Notice: Subject to any disclaimer, the term of this patent is extended or adjusted under 35 U.S.C. 154(b) by 760 days.

(21) Appl. No.: 11/805,425

(22) Filed: May 23, 2007

(65) Prior Publication Data

US 2007/0275428 A1 Nov. 29, 2007

Related U.S. Application Data

(60) Provisional application No. 60/802,860, filed on May 23, 2006.

(51) Int. Cl.
*C07K 1/00* (2006.01)

(52) U.S. Cl. .................................................. 530/350
(58) Field of Classification Search ................. 530/350
See application file for complete search history.

(56) References Cited

U.S. PATENT DOCUMENTS 7,601,517 B2 * 10/2009 Gambhir et al. ............ 435/69.7

* cited by examiner

*Primary Examiner*—Maryam Monshipouri
(74) *Attorney, Agent, or Firm*—Thomas, Kayden, Horstemeyer & Risley, LLP

(57) ABSTRACT

Briefly described, embodiments of this disclosure include phosphorylation sensing systems, methods of detecting phosphorylation, noninvasive methods for detecting the interaction of a first protein with a second protein within a living animal, fusion proteins including the phosphorylation sensing system, vectors including the phosphorylation sensing system, kits including the phosphorylation sensing system, transgenic cells including the phosphorylation sensing system, and the like are provided.

23 Claims, 18 Drawing Sheets

(9 of 18 Drawing Sheet(s) Filed in Color)

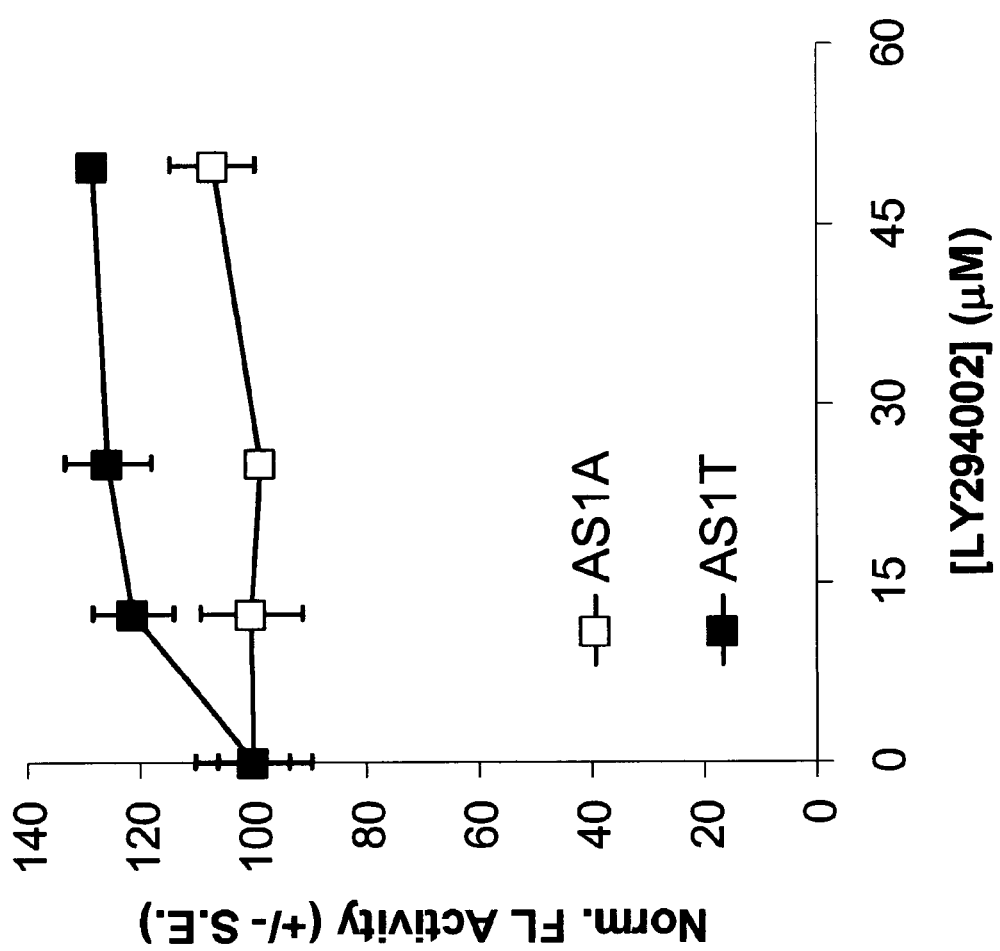

PROTEIN PHOSPHORYLATION IMAGING SYSTEMS, METHODS OF MAKING PHOSPHORYLATION IMAGING SYSTEMS, AND METHODS OF USE THEREOF

CROSS-REFERENCE TO RELATED APPLICATION

This application claims priority to U.S. provisional applications entitled, "PROTEIN PHOSPHORYLATION IMAGING SYSTEMS, AND METHODS OF USE THEREOF," having Ser. No. 60/802,860, filed on May 23, 2006, which is entirely incorporated herein by reference.

STATEMENT REGARDING FEDERALLY SPONSORED RESEARCH OR DEVELOPMENT

This invention was made with Government support under contracts CA114747 and CA082214 awarded by the National Institutes of Health. The Government has certain rights in this invention.

BACKGROUND

In general, cellular processes are a combination of many complex sets of interactions that include gene transcription, mRNA translation, protein-RNA interactions, protein-DNA interactions, protein-protein interactions, and protein modifications such as phosphorylation. As biology moves forward with a "systems biology" approach, so must imaging of molecular/cellular events in living subjects, to lead to a "systems imaging" approach. It will be important to characterize more complex interactions that occur in living subjects by developing approaches that can monitor intracellular communication pathways including protein phosphorylation. Protein phosphorylation is at the heart of signal transduction, developmental biology, cell assembly, cellular metabolism, and a whole array of other biological processes. In addition, many cellular protein-protein interactions are specifically controlled by phosphorylation and de-phosphorylation of proteins at specific amino acids in sequence-specific regions. Therefore, methods are needed that would allow imaging of complex interactions in the context of intact cells anywhere within a living subject.

SUMMARY

Briefly described, embodiments of this disclosure include phosphorylation sensing systems, methods of detecting phosphorylation, noninvasive methods for detecting the interaction of a first protein with a second protein within a living animal, fusion proteins including the phosphorylation sensing system, vectors including the phosphorylation sensing system, kits including the phosphorylation sensing system, transgenic cells including the phosphorylation sensing system, and the like are provided.

One exemplary phosphorylation sensing system, among others, includes: a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein.

One exemplary fusion protein, among others, includes: a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein.

One exemplary vector, among others, includes: a polynucleotide sequence encoding a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein.

One exemplary kit, among others, includes: a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein; and directions for use.

One exemplary transgenic cell or progeny thereof, among others, includes: a transgene comprising a polynucleotide encoding a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein.

One exemplary method of detecting phosphorylation, among others, includes: providing a phosphorylation sensing system that includes: a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein; exposing the phosphorylation sensing system to a system having conditions that initiate phosphorylation of the phosphorylation domain; introducing a bioluminescence initiating compound to the system; and monitoring for the presence of a bioluminescent signal.

One exemplary noninvasive method for detecting the interaction of a first protein with a second protein within a living animal, among others, includes: providing a vector, comprising a first polynucleotide that encodes a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein; administering the first vector to the living animal; generating a fusion protein in the living animal; administering a bioluminescence initiating compound to the living animal, wherein a bioluminescence energy is emitted from the bioluminescence donor molecule upon interaction with the bioluminescence initiating compound; and monitoring for the presence of a bioluminescent signal in the living animal.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 6b illustrates the inhibition of Akt kinase activity led to increase in complemented FL activity in BT474 cells transiently transfected with AS1T. BT474 cells were transiently transfected with AS1A or AS1T for 24 hours in the presence of the PI-3K inhibitor LY294002 (LY) or carrier control. RL was used a transfection control. Complemented FL and RL activities were determined by luminometer assay and normalized for transfection efficiency using RL activity and for protein content. LY led to a dose-dependent increase in complemented FL activity in BT474 cells transiently transfected with AS1T, compared to that of carrier control treated cells. It should be noted that $p<0.05$ relative to carrier control treated cells.

FIG. 7a illustrates 293T/AS1T cells that were treated with different concentrations of LY or carrier control (1% DMSO) for 6, 12 and 24 hours prior to analysis of complemented FL activity by bioluminescence imaging of intact cells. FIG. 7b illustrates a graph of the quantitation of data from FIG. 7a. Protein content in each well was determined upon cell lysis. Complemented FL activity in each well was normalized for protein content and then to carrier control treated cells. Each data point represents the average normalized complemented FL activity+/−S.E.M. It should be noted that p<0.05 relative to AS1A cells treated with LY for the same duration. FIG. 7c illustrates the effect of perifosine on complemented FL activity in 293T/AS1A and 293T/AS1T cells were determined as in a, except 1% ethanol was used as the carrier control. FIG. 7d illustrates a graph of the quantitation of data from FIG. 7c. It should be noted that p<0.05 relative to AS1A cells treated with perifosine for the same duration.

FIG. 8a illustrates the reversibility of AS1T for indirect monitoring of Akt kinase activity. 293T/AS1T and 293T/AS1A cells were treated with 50 μM of LY or carrier control (1% DMSO) for 24 hours, prior to medium change with 50 μM of LY or carrier control for another 24 hours. Complemented FL activity in 293T/AS1T cells was determined in as FIG. 7a (left) and normalized for protein content and then to carrier control treated cells. It should be noted that p<0.05 relative to AS1A and that p<0.05 relative to carrier control treated cells. FIG. 8b illustrates the reversibility of AS1T in response to perifosine. 293T/AS1T and 293T/AS1A cells were treated with 25 μM of perifosine or carrier control (1% ethanol) for 6 hour, prior to medium change 25 μM perifosine or carrier control for another 6 hours. Complemented FL activity was determined as in FIG. 8a.

FIG. 9a illustrates 293T/AS1A and 293T/AS1T cells that were treated with 50 μM of LY or carrier control for 24 hours. Complemented FL activity was determined by bioluminescence imaging (left), followed by normalization of protein content (right). It should be noted that p<0.05 relative to AS1A treated with the same concentrations of LY or carrier control for 24 hours. FIG. 9b illustrates Akt phosphorylation and kinase activity in LY treated cells from FIG. 9a. The top of FIG. 9b illustrates the amount of phosphorylated Akt in cell lysates as determined by phosphorylation-specific western blotting, followed by stripping and reprobing for total Akt. α-tubulin was used as a loading control. The ratio of phosphorylated to total Akt, as well as normalized pAkt (to α-tubulin and to carrier control treated cells) were indicated. The bottom of FIG. 9b illustrates in vitro Akt kinase activity in cell lysates was determined using purified GSK-3β as a substrate. The amount of phosphorylated GSK-3β was normalized for amount of total Akt immunoprecipitated for each sample and to carrier control treated cells. The ratio of phosphorylated to total Akt for each sample was also indicated on the bottom. FIG. 9c illustrates 293T/AS1T and 293T/AS1A cells that were treated with 25 μM of perifosine or carrier control for 6 hours, and complemented FL activity was determined in as FIG. 9a. It should be noted that p<0.05 relative to AS1A treated with the same concentrations of perifosine or carrier control for 6 hours. FIG. 9d illustrates Akt phosphorylation and kinase activity in 293T/AS1A and 293T/AS1T cells treated with perifosine for 6 hours from FIG. 9c.

FIG. 10a illustrates the efficacy of perifosine in inhibition of Akt kinase activity in living subjects was determined by bioluminescence imaging of nude mice bearing 293T/AS1A and 293T/AS1T xenografts. Mice were treated with 30 mg/kg of perifosine or carrier control at time 0 hour and re-imaged at 6, 15, 27 and 39 hours upon i.p. injection of D-Luciferin. FIG. 10b illustrate the max photons at each time point was normalized to that of carrier control treated mice and expressed as average normalized max photons+/−S.E.M. for each xenograft. It should be noted that p<0.05 relative to AS1A xenografts.

DETAILED DESCRIPTION

Figure 1:
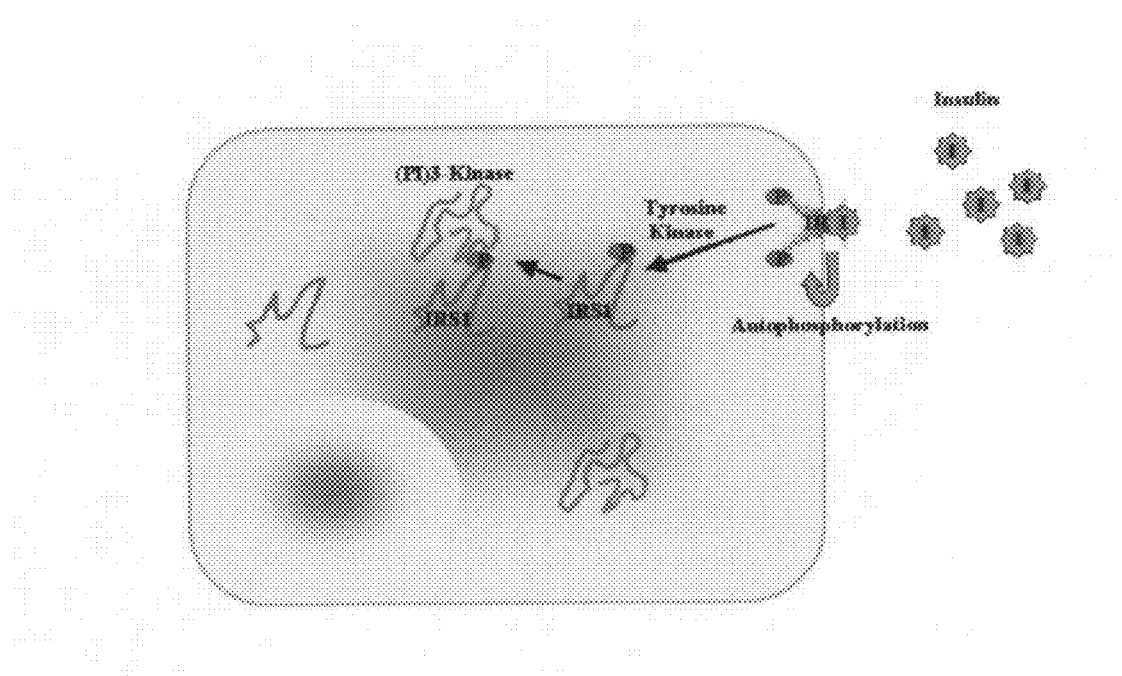
FIG. 1 illustrates the insulin receptor pathway.

Embodiments of the present disclosure will employ, unless otherwise indicated, techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

The term "complementing fragments" or "complementary fragments" when used in reference to split protein fragments refers to fragments of a bioluminescent protein that are individually inactive (e.g., do not express the reporter phenotype), wherein binding of the complementing fragments restores reporter activity. The terms "complementing" or "complementation" refer to when the fragments bind together. The terms "self-complementing", "self-assembling", and "spontaneously-associating", when used to describe two fragments of the same protein, mean that the fragments are capable of reconstituting into an active bioluminescent protein when the individual fragments are soluble and are sufficiently close to or in contact with one another.

"Bioluminescent initiator molecule" is a molecule that can react with a bioluminescent protein to generate bioluminescence.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous overall) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biologically functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also refers to the degree of sequence relatedness between polypeptide as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073, (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminus of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. (Robertson, et al., *J. Am. Chem. Soc.,* 113: 2722, 1991; Ellman, et al., *Methods Enzymol.,* 202: 301, 1991; Chung, et al., *Science,* 259: 806-9, 1993; and Chung, et al., *Proc. Natl. Acad. Sci. USA,* 90: 10145-9, 1993). In a second method, translation is carried out in *Xenopus oocytes* by microinjection of mutated mRNA and chemically aminoacylated suppressor tRNAs (Turcatti, et al., *J. Biol. Chem.,* 271: 19991-8, 1996). In a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., *Biochem.,* 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., *Protein Sci.,* 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells, inter alia.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminus of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain or mRNA that make up an amino acid or termination signal.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genome or plasmid DNA, animal viral genome, or viral DNA, or may contain elements of both.

As used herein, the term "vector" or "expression vector" is used to denote a DNA molecule, linear or circular, which includes a segment encoding a polypeptide of interest operably linked to additional segments that provide for its transcription and translation upon introduction into a host cell or host cell organelles. Such additional segments include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of one or more of the above.

"DNA regulatory sequences", as used herein, are transcriptional and translational control sequences, such as promoters, enhancers, polyadenylation signals, termination signals, and the like, that provide for and/or regulate expression of a coding sequence in a host cell.

A "promoter sequence" is a DNA regulatory region in an operon capable of binding RNA polymerase in a cell and initiating mRNA transcription of a downstream (3' direction) coding sequence. For purposes of defining the present invention, the promoter sequence is bound at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

As used herein, the term "hybridization" refers to the process of association of two nucleic acid strands to form an antiparallel duplex stabilized by means of hydrogen bonding between residues of the opposite nucleic acid strands.

"Hybridizing" and "binding", with respect to polynucleotides, are used interchangeably. The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions sets forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, substantially similar conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature. Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more.

As used herein the term "isolated" is meant to describe a polynucleotide, a polypeptide, an antibody, or a host cell that is in an environment different from that in which the polynucleotide, the polypeptide, the antibody, or the host cell naturally occurs.

By "administration" is meant introducing a sensor of the present disclosure into a subject. The preferred route of administration of the sensor is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the sensor of the present disclosure is defined as an amount sufficient to yield an acceptable image using equipment that is available for clinical use. A detectably effective amount of the sensor of the present disclosure may be administered in more than one injection. The detectably effective amount of the sensor of the present disclosure can vary according to factors such as the degree of susceptibility of the individual, the age, sex, and weight of the individual, idiosyncratic responses of the individual, the dosimetry, and the like. Detectably effective amounts of the sensor of the present disclosure can also vary according to instrument and film-related factors. Optimization of such factors is well within the level of skill in the art.

As used herein, the term "organelle" refers to cellular membrane-bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

As used herein, the term "host" or "organism" includes humans, mammals (e.g., cats, dogs, horses, etc.), living cells, and other living organisms. A living organism can be as simple as, for example, a single eukaryotic cell or as complex as a mammal.

General Discussion

The present disclosure includes phosphorylation sensor systems, methods of producing phosphorylation sensor systems, methods of using phosphorylation sensor systems, methods of using split protein fragments (e.g., bioluminescent protein fragments) for detecting (e.g., phosphorylation and/or de-phosphorylation), methods of detecting the phosphorylation state (e.g., phosphorylation and/or de-phosphorylation, methods of screening phosphorylation and/or de-phosphorylation related molecules (e.g., drugs), and the like.

In general, embodiments of phosphorylation sensor systems include, but are not limited to, a first split protein fragment, a phosphorylation domain, a first linker peptide, a substrate recognition domain, and a second split protein fragment. Examples 1 and 2 illustrate two embodiments of the phosphorylation sensor system. The first split protein fragment and the second split protein fragment can complement (e.g., self complement or spontaneously self complement) with one another to form a bioluminescent protein. The bioluminescent protein emits bioluminescent energy when exposed to a bioluminescence initiating compound. Although embodiments of the split protein fragments are not bioluminescent when separated, the split protein fragments can be induced to complement or are able to spontaneously self complement upon coming into sufficiently close contact with one another to form a bioluminescent protein (e.g., a Luciferase protein).

In an embodiment, the first linker peptide is semi-rigid or rigid and inhibits the first split protein fragment from interacting with the second split protein fragment unless the phosphorylation domain is phosphorylated. The phosphorylation domain is phosphorylated when a target protein or target substrate is phosphorylated. When the phosphorylation domain is phosphorylated, the phosphorylation domain binds to the substrate recognition domain, and the first split protein fragment and the second split protein fragment can complement. When the first split protein fragment and the second split protein fragment complement with one another to form the bioluminescent protein, the bioluminescent protein can interact with a bioluminescent initiating compound to generate a bioluminescent signal. Thus, the presence or absence of a bioluminescent signal in a host can be correlated to the phosphorylation or de-phosphorylation (or to the fact that the phosphorylation domain is not phosphorylated) of the phosphorylation domain. The phosphorylation state of the phosphorylation domain can be used to indirectly measure the phosphorylation or de-phosphorylation of a target in a host. Additional details are provided in Example 1.

In another embodiment, when the phosphorylation domain is phosphorylated, the phosphorylation domain binds to the substrate recognition domain. The relative position of the first split protein fragment and the second split protein fragment when the phosphorylation domain binds to the substrate recognition domain is such that the first split protein fragment and the second split protein fragment are sterically hindered from interacting. Thus, when the phosphorylation domain binds to the substrate recognition domain the first split protein fragment and the second split protein fragment do not or do not substantially complement with one another. When the phosphorylation domain is not phosphorylated, the phosphorylation domain does not bind to the substrate recognition domain. The relative position of the first split protein fragment and the second split protein fragment when the phosphorylation domain does not bind to the substrate recognition domain is such that the first split protein fragment and the second split protein fragment are able to interact and complement with one another. When the first split protein fragment and the second split protein fragment complement with one another to form the bioluminescent protein, the bioluminescent protein can interact with a bioluminescent initiating compound to generate a bioluminescent signal. Thus, the presence or absence of a bioluminescent signal in a host can be correlated to the de-phosphorylation (or the fact that the phosphorylation domain is unphosphorylated) or phosphorylation of the phosphorylation domain. The phosphorylation state of the phosphorylation domain can be used to indirectly measure the phosphorylation or de-phosphorylation of a target in a host. Additional details are provided in Example 2.

Thus, phosphorylation sensor systems can be used to directly or indirectly detect, study, monitor, evaluate, and/or screen, biological events in vivo or in vitro, such as, but not limited to, the phosphorulation state (e.g., phosphorylated, unphosphorylated) of a target protein (e.g., a target substrate). In addition, phosphorylation sensor systems can be used to screen molecules (e.g., drugs) related to the phosphorylation and/or de-phosphorylation of the target protein of a phosphorylation and/or de-phosphorylation process of interest.

Embodiments of the present disclosure can be used to detect (and visualize) and/or quantitate phosphorylation and/or de-phosphorylation events in in vitro as well as in in vivo studies, which can decrease time and expense since the same system can be used for cells and living organisms. Embodiments of the present disclosure can be used to test an event occurance in a large number of samples, and has the capacity to transition from single cells to living animals without changing the phosphorylation sensor system and/or the imaging device.

Briefly described, embodiments of this disclosure, among others, include phosphorylation sensor systems, fusion proteins including phosphorylation sensor systems, vectors encoding phosphorylation sensor systems, and methods of using the phosphorylation sensor systems, fusion proteins, vectors, and the like. Note that for each phosphorylation sensor system, protein, fusion protein, protein fragment, and nucleotide, one skilled in the art would be able to determine the corresponding nucleotide sequence or protein sequence, respectively, and be able to introduce each into a system of interest.

Phosphorylation Sensor Systems and Methods of Use

In general, the phosphorylation sensor system can be used in vivo and/or in vitro. In an embodiment, the phosphorylation sensor system can be introduced into an environment system (e.g., inside a cell or outside a cell and/or to a host), the phosphorylation sensor system can be expressed (e.g., using a vector) in the environment, and/or the phosphorylation sensor system can be included in a transgenic animal. In an embodiment, the phosphorylation sensor system can be introduced into a host or organism in vivo.

The phosphorylation sensor system is placed in conditions that may initiate phosphorylation or de-phosphorylation (or the fact that the phosphorylation domain is not phosphorylated) in a target protein of interest. The phosphorylation domain and the substrate recognition domain are selected to bind once the phosphorylation reaction occurs to the target protein of interest. In this regard, the phosphorylation sensor system can be used to indirectly determine the phosphorylation state (e.g., phosphorylated, unphosphorylated and de-phosphorylated) of the phosphorylation domain.

In an embodiment, once binding occurs between the phosphorylation domain and the substrate recognition domain, the first linker protein bends or flexes and allows the first split protein and the second split protein to interact (e.g., complement with one another). A bioluminescent signal is generated upon interaction of the complemented first and second split proteins (the bioluminescent protein) and a bioluminescent initiating compound. If the phosphorylation domain is de-phosphorylated, the first split protein and the second split protein are separated and the bioluminescent signal ceases (turned-off). Thus, the phosphorylation sensor system is responsive (e.g., an event occurs or does not occur) to the phosphorylation state of a target protein of interest.

In another embodiment, once binding occurs between the phosphorylated domain and the substrate recognition domain, the first split protein and the second split protein are not able to interact with one another and a bioluminescent signal is not generated. If the phosphorylation domain is de-phosphorylated (or unphosphrylated), the separation of the substrate binding domain from the phosphorylation domain leads to flexibility in the fusion protein and the first split protein and the second split protein can interact to form the bioluminescent protein. A bioluminescent signal is generated upon interaction of the bioluminescent protein and a bioluminescent initiating compound. Thus, the phosphorylation sensor system is responsive to the phosphorylation state of a target protein of interest.

As mentioned above, the phosphorylation sensor system is used in methods of detecting phosphorylation or de-phosphorylation (or unphosphorylated). Protein phosphorylation controls the functional activity of many cellular proteins. So far, only the phosphospecific antibody has been used to identify this event, and this approach is restricted to cell lysates and intact cells. In contrast, embodiments of the present disclosure can be used to study cell lysates, intact cells, and living animals. In an embodiment, phosphorylation sensor systems can be used to construct vectors expressing fusion proteins containing phosphorylation specific interacting proteins as well as other expression systems.

In an embodiment, the phosphorylation domain is selected so that when the target protein is phosphorylated (e.g., phosphorylation of the insulin receptor substrate 1), the phosphorylation domain is phosphorylated and binds to the substrate recognition domain. In an embodiment, the binding of the phosphorylation domain and the substrate recognition domain brings the first split protein fragment and the second split protein fragment into relatively close proximity so that the first split protein fragment and the second split protein fragment can complement one another. The first linker peptide bends or flexes because of the relative strength of the interaction between the phosphorylation domain and the substrate recognition domain. Subsequently, a bioluminescent signal is generated upon interaction of the complemented first and second split proteins with a bioluminescent initiating compound, which indicates that the target protein was phosphorylated.

In particular, the method includes a phosphorylation sensor system (also referred to as the "phosphorylation sensor structure") such as, but not limited to, a first split protein fragment (e.g., N-terminal fragment), the phosphorylation domain, a first linker peptide, a substrate recognition domain, and a second split protein fragment (e.g., C-terminal fragment). A phosphorylation domain corresponding to the phosphorylation reaction of interest (e.g., the phosphorylation of a target protein) is attached to a first end of the first split protein fragment. A substrate recognition domain that binds with the phosphorylation domain upon phosphorylation of the phosphorylation domain is attached to the first end of the second split protein fragment. A first linker peptide is attached (e.g., directly or indirectly (e.g., a polypeptide sequence)) to each of the phosphorylation domain and the substrate recognition domain to form a continuous structure.

In an embodiment, the phosphorylation sensor structure has the following order: the first split protein fragment, the phosphorylation domain, the first linker peptide, the substrate recognition domain, and the second split protein fragment. It should be noted that additional peptide sequences could be included in the phosphorylation sensor structure such as, but not limited to, one or more linker peptides, one or more peptides to connect one or more of the components, and also the use of different phosphorylation domains and substrate recognition domains, and combinations thereof. However, additional sequences would not alter the function of the phosphorylation sensor structure, but would merely act to connect one or more of the components.

Other embodiments of the phosphorylation sensor structure are contemplated that have a different component order. For example, the phosphorylation domain and the substrate recognition domain should typically be positioned so that when the phosphorylation domain is phosphorylated, the phosphorylation domain and the substrate recognition domain can bind. In an embodiment, the first split protein fragment and the second split protein fragment are positioned so that when the phosphorylation domain and the substrate recognition domain bind, the first split protein fragment and the second split protein fragment are able to complement with one another. In another embodiment, the first split protein fragment and the second split protein fragment are positioned so that when the phosphorylation domain and the substrate recognition domain bind, the first split protein fragment and the second split protein fragment are hindered from complementing with one another. It is contemplated that two or more linker peptides may be used in the phosphorylation sensor structure, and in another embodiment, it is contemplated that no linker peptides are included in the phosphorylation sensor structure.

In another embodiment, de-phosphorylation (or the lack of phosphorylation of the phosphorylation domain) can be examined. In an embodiment, a bioluminescent signal is present when the target protein has been phosphorylated, but the bioluminescent signal is no longer present when the target protein is de-phosphorylated. So, when the target protein is de-phosphorylated, the bioluminescent signal is "turned off". In other words, the phosphorylation domain and the substrate recognition domain of the phosphorylation sensor system are no longer bound and the first linker peptide pulls the first split protein fragment and the second split protein fragment apart, which "turns off" the bioluminescent signal. Thus, phosphorylation sensor systems can be used to detect, study, monitor, evaluate, and/or screen, phosphorylation events (e.g., the phosphorylation state) in vivo or in vitro by ascertaining when the bioluminescent signal is no longer present.

In another embodiment, de-phosphorylation (or unphosphorylation) can be examined. In an embodiment, a bioluminescent signal is not present when the target protein has been phosphorylated, but a bioluminescent signal is generated when the target protein is de-phosphorylated. So, when the target protein is de-phosphorylated, the bioluminescent signal is "turned on". In other words, the phosphorylation domain and the substrate recognition domain of the phosphorylation sensor system are bound after de-phosphorylation and the first split protein fragment and the second split protein fragment are able to complement, which "turns on" the bioluminescent signal. Thus, phosphorylation sensor systems can be used to detect, study, monitor, evaluate, and/or screen, phosphorylation events (e.g., the phosphorylation state) in vivo or in vitro by ascertaining when the bioluminescent signal is present.

In an embodiment, the phosphorylation sensor system can be used to screen molecules such as, but not limited to, molecules that induce and/or are involved in phosphorylation and/or de-phosphorylation of a target protein, molecules related to phosphorylation and/or de-phosphorylation processes (e.g., events that may occur prior to or after the phosphorylation and/or de-phosphorylation of interest), molecules that inhibit or enhance the upstream process of phosphorylation, and the like. In an embodiment, the phosphorylation sensor system can be used to examine drug-mediated modulation of proteins in a host.

In an embodiment, a phosphorylation sensor system is selected that is appropriate for the phosphorylation and/or de-phosphorylation reaction or process of interest. In particular, the phosphorylation domain is selected to be responsive to the phosphorylation event state or process of interest. The molecules to be screened are individually introduced into the environment (e.g., a cell, a host, or transgenic animal) that includes the phosphorylation sensor system. When testing for phosphorylation, the phosphorylation sensor system will generate a bioluminescent signal (e.g., be "turned on") if phosphorylation occurs, which can indicate that the molecule induced phosphorylation or did not inhibit phosphorylation, for example. If phosphorylation does not occur (or if de-phosphorylation occurs), then a bioluminescent signal is not generated, which can indicate that the molecule did not induce phosphorylation or inhibited phosphorylation, for example. In one embodiment, when testing for the phosphorylation event (e.g., de-phosphorylation), the phosphorylation sensor system will initially (e.g., prior to introduction of the molecule) generate a bioluminescent signal, but the signal will be turned off if de-phosphorylation (or if it is unphosphorylated) occurs. Proper design of the phosphorylation sensor system and the experiments can assist in determining the effect the molecules are having on the system.

In an embodiment, a phosphorylation sensor system is selected that is appropriate for the phosphorylation event state or process of interest. In particular, the phosphorylation domain is selected to be responsive to the phosphorylation event state, or process of interest. The molecules to be screened are individually introduced into the environment (e.g., a cell, a host, or transgenic animal) that includes the phosphorylation sensor system. When testing for phosphorylation, the phosphorylation sensor system will not generate a bioluminescent signal (e.g., be "turned off") if phosphorylation occurs, which can indicate that the molecule induced phosphorylation or did not inhibit phosphorylation, for example. If phosphorylation does not occur, then a bioluminescent signal is generated, which can indicate that the molecule did not induce phosphorylation or inhibited phosphorylation, for example. When testing for de-phosphorylation (or if it is unphsophorylated), the phosphorylation sensor system will not initially (e.g., prior to introduction of the molecule) generate a bioluminescent signal, but the signal will be turned on if de-phosphorylation occurs. Proper design of the phosphorylation sensor system and the experiments can assist in determining the effect the molecules are having on the system.

In an embodiment, phosphorylation sensor systems can also be designed to sense phosphorylation processes that occur within a protein that leads to changes in the protein conformation (e.g., folding). In this embodiment a bioluminescent signal can be measured in a protein, and upon the phosphorylation of a particular amino acid within the protein, the folding pattern of the protein changes and "turns off" the bioluminescent signal. Similarly, this strategy will also work in the other way that leads to signal through phosphorylation.

It should be noted that the amount effective to result in uptake of the phosphorylation sensor system into the cells or tissue of interest will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine or tissue samples, or blood urine or tissue samples of the animals mentioned for veterinary applications.

Split Protein Fragments

The split protein fragments and the bioluminescent protein are often used in an interchangeable manner, but the spit protein fragments refer to two protein fragments that can complement to form the bioluminescent protein. Each of the protein fragment sequences is obtained from the bioluminescent protein. The combination of the protein fragment sequences may not include the entire exact bioluminescent protein sequence, and/or portions of the protein fragments sequences may overlap one another. However, the complementation of the split protein fragments forms an active bioluminescent protein.

The split protein can include, but is not limited to, non-self complementing split protein fragments and self complementing split protein fragments. In particular, the split protein can be obtained from biolumincscent proteins such as, but not limited to, Luciferases or photoproteins. In an embodiment, the split protein can obtained from biolumincscent proteins such as, but not limited to, *Renilla* Luciferase (the nucleotide sequences are described below and the amino acid sequence is SEQ ID: No 1 as well as other sequences described below), portions thereof, mutants thereof, variants thereof; Coleoptera Luciferase (the nucleotide sequence is SEQ ID: No 15, and the amino acid sequence is SEQ ID: No 16), portions thereof, mutants thereof, variants thereof; Firefly Luciferase (the nucleotide sequence is SEQ ID: No 4 and the amino acid sequence is SEQ ID: No 33), portions thereof, mutants thereof, variants thereof; Gaussia Luciferase (the nucleotide sequence is SEQ ID: No 17 and the amino acid sequence is SEQ ID: No 18), portions thereof, mutants thereof, variants thereof; aqeuorin photoproteinm Luciferase (the nucleotide sequence is SEQ ID: No 19, and the amino acid sequence is SEQ ID: No 20), portions thereof, mutants thereof, variants thereof; and Bacterial Luciferase (the nucleotide sequence is SEQ ID: No 21, and the amino acid sequence is SEQ ID: No 22), portions thereof, mutants thereof, variants thereof; and the like.

The split protein fragments can be included in a fusion protein. For example, the fusion protein can include the split protein of each of the fragments separated by the phosphorylation domain, substrate recognition domain, the first linker peptide, other linker peptides, and/or other components consistent with the teachings of this disclosure. The split protein fragments or a fusion protein including the split protein fragment can be expressed in a system (e.g., a cell) using a vector, for example, by methods known to those of skill in the art.

In an embodiment, the bioluminescent protein can include, but is not limited to, a *Renilla* Luciferase protein (SEQ ID: No 1, or split sequences corresponding to SEQ ID No. 24 and 26), double mutant (C124A/M185V) *Renilla* Luciferase proteins (e.g., SEQ ID: No 2), mutated *Renilla* Luciferase proteins (e.g., SEQ ID: No 3), variants of each, conservatively modified variants of each, and combinations thereof. Each of the double mutant (C124A/M185V) *Renilla* Luciferase (SEQ ID: No 8) and the mutated *Renilla* Luciferase proteins (SEQ ID: No 9) have the split to form the split protein fragments at the same amino acid as *Renilla* Luciferase protein (SEQ ID: No 7, or split sequences corresponding to SEQ ID No. 37 and 38). In other words, the splits sequences of each of the double mutant (C124A/M185V) *Renilla* Luciferase and the mutated *Renilla* Luciferase protein are the same as the *Renilla* Luciferase protein (SEQ ID: No 7, or split sequences corresponding to SEQ ID No. 37 and 38) except for the mutations.

The term "mutant" is employed broadly to refer to a protein that differs in some way from a reference wild-type protein, where the protein may retain biological properties of the reference wild-type (e.g., naturally occurring) protein, or may have biological properties that differ from the reference wild-type protein. The term "biological property" of the subject proteins includes, but is not limited to, spectral properties, such as emission maximum, quantum yield, brightness, and the like and in vivo and/or in vitro stability (e.g., half-life), and the like. Mutants can include single amino acid changes (point mutations), deletions of one or more amino acids (point-deletions), N-terminal truncations, C-terminal truncations, insertions, and the like. Mutants can be generated using standard techniques of molecular biology.

In an embodiment, the Luciferase mutants retain Luciferase activity (e.g., catalyze the conversion of a coelenterazine substrate into a luminescent product in the presence of molecular oxygen). In an embodiment, the Luciferase mutants have at least one of the following properties relative to their corresponding reference wild-type protein: modulated stability, enhanced light output, and/or modulated emission wavelength maximum and modulated substrate utilization. In certain embodiments, the subject mutants include two or more of the above properties (e.g., modulated stability and enhanced brightness, enhanced light output and modulated emission maximum, modulated stability and modulated emission maximum, and the like) or include three or more of the above properties (e.g., modulated stability, enhanced light output, and modulated emission maximum).

In an embodiment, the split protein fragments are self complementing fragments (e.g., inherent self affinity between the N- and C-terminal fragments of a split protein (e.g., a monomeric Firefly Luciferase protein) brings the fragments close to each other and generate an event called complementation) and do not bioluminescent when separated. The split protein self complementing fragments are able to spontaneously self complement upon coming into close enough proximity to recover the substrate binding property or coming in contact with one another to form a bioluminescent protein. An example of the self complementing fragments include the bioluminescent Firefly Luciferase protein which can spontaneously self complement and then bioluminescence upon interaction with a bioluminescence initiating compound.

In an embodiment of the split protein self complementing fragments, the fragments are obtained from the Firefly Luciferase protein and conservatively modified variants thereof. The split protein self complementing fragments include portions, or conservatively modified variants thereof, of the Firefly Luciferase protein (SEQ ID No. 4 (nucleotide sequence) and SEQ ID No. 33 (amino acid sequence). The Firefly Luciferase protein or the split protein self complementing fragments can include conservativley modified variants as long as the conservativley modified variant retains the bioluminescent characteristics of the Firefly Luciferase protein or the split protein self complementing fragments. It should be noted that polynucleotides encoding the conservativley modified variants are intended to be disclosed by this disclosure.

The split protein, self complementing fragments may include, but are not limited to, a N fragment (e.g., amino acid sequence SEQ. ID No. 6 and nucleotide sequence SEQ. ID No. 5 (corresponding to aa residue 1 to 475)) and a C fragment (e.g., aa residue 245 to 550 of SEQ ID: No 46 and 300 to 550 of SEQ ID: No 47 and a portion of the nucleotide sequence SEQ. ID No. 4 (corresponding to the appropriate amino acids) of the Firefly Luciferase protein. In particular, split protein self complementing fragments may include, but are not limited to, a Nfluc fragment (1-398 of SEQ ID: No 10), a Nfluc fragment (amino acid sequence (aa 1-474) SEQ. ID No. 6 and nucleotide sequence SEQ. ID No. 5), a Nfluc fragment (amino acid sequence (aa 1-455) of SEQ ID: No 33 and nucleotide sequence SEQ. ID No. 4 (corresponding to aa residue 1 to 455)), a Nfluc fragment (amino acid sequence (aa 1-450) of SEQ ID: No 33 and nucleotide sequence SEQ. ID No. 4 (corresponding to aa residue 1 to 450)), a Nfluc fragment (amino acid sequence (aa 1-398) of SEQ ID: No 10 and nucleotide sequence SEQ. ID No. 9), a Cfluc fragment (aa 245-550 of SEQ ID: No 33 and nucleotide sequence SEQ. ID No. 4 corresponding to aa 245 to 550), a Cfluc fragment (SEQ ID: No 8 and nucleotide sequence SEQ. ID No. 7 corresponding to aa 265 to 550), a Cfluc fragment (aa 300-550 of SEQ ID: No 33 and nucleotide sequence SEQ. ID No. 4 corresponding to aa 300 to 550), a Cfluc fragment (aa 310-550 of SEQ ID: No 33 and nucleotide sequence SEQ. ID No. 4 corresponding to aa 310 to 550), a Cfluc fragment (aa 325-550 of SEQ ID: No 33 and nucleotide sequence SEQ. ID No. 4 corresponding to aa 325 to 550), Cfluc fragment (aa 398-550 of SEQ ID: No 12 and nucleotide sequence SEQ. ID No. 11), and a Cfluc fragment (aa 394-550 of SEQ ID: No. 14 nucleotide sequence SEQ. ID No. 13).

The split protein self complementing fragments can be included in a fusion protein. For example, the fusion protein can include the split protein of one of the self complementing fragments while also including a protein of interest and/or other proteins, linker, and/or other components consistent with the teachings of this disclosure. The split protein self complementing fragments or a fusion protein including the split protein self complementing fragment can be expressed in a environment (e.g., a cell) using a vector, for example.

Phosphorylation Sensor System Vector

Embodiments of the present disclosure include, but are not limited to, polynucleotides that encode the phosphorylation sensor system as described above and degenerate nucleotide sequences thereof as well as fusion proteins of the phosphorylation sensor system and degenerate nucleotide sequences thereof. Methods of producing vectors (e.g., viral and non-viral) and polynucleotides are well known in the art. It should be noted that the fusion protein can be expressed using other expression systems, and the vector is merely an illustrative embodiment.

Linker Peptide

The linker peptide can be a peptide that bonds directly or indirectly to the phosphorylation domain and the substrate recognition domain. In an embodiment, the linker peptide acts to limit the interaction of the first split protein fragment and the second split protein fragment when the phosphorylation domain is not phosphorylated (See Examples for additional details). In another embodiment, the linker peptide acts to facilitate the interaction of the first split protein fragment and the second split protein fragment when the phosphorylation domain is not phosphorylated (See Examples for additional details).

As mentioned above, an embodiment of the linker peptide (e.g., the first linker peptide) can be a peptide that is semi-rigid or rigid. The rigidity of the first linker peptide is sufficient to substantially limit the interaction of the first split protein fragment and the second split protein fragment. In addition, the rigidity of the first linker peptide is flexible enough to allow the first split protein fragment and the second split protein fragment to interact upon a phosphorylation interaction between the phosphorylation domain and the substrate recognition domain under appropriate conditions. In an embodiment, the rigidity of the first linker peptide is weak enough that if the phosphorylation domain and the substrate recognition domain become unbound, the first split protein fragment and the second split protein fragment will be pulled apart.

In embodiments that include one or more linker peptides in addition to the first linker peptide, the combination of the first linker peptide and the other linker peptides has a rigidity sufficient to substantially limit the interaction of the first split protein fragment and the second split protein fragment, while also being flexible enough to allow the first split protein fragment and the second split protein fragment to interact upon a phosphorylation interaction between the phosphorylation domain and the substrate recognition domain under appropriate conditions. In an embodiment, the rigidity of the combination of the peptide linkers is weak enough that if the phosphorylation domain and the substrate recognition domain become unbound, the first split protein fragment and the second split protein fragment will be pulled apart.

In embodiments that include one or more linker peptides in addition to the first linker peptide, the combination of the first linker peptide and the other linker peptides is sufficiently flexible to not hinder the interaction of the first split protein fragment and the second split protein fragment upon a de-phosphorylation interaction between the phosphorylation domain and the substrate recognition domain under appropriate conditions.

The first linker peptide and/or other linker peptides selected for an embodiment may depend at least upon the strength of the complementation potential between the first split protein fragment and the second split protein fragment, the strength of the phosphorylation potential between the phosphorylation domain and the substrate recognition domain, and the like.

TABLE 1 illustrates exemplary linkers.

| SEQ. ID No. | Amino acid sequence of illustrative linkers |
|---|---|
| 34 | GGGGSGGGGS |
| 35 | ACGSLSCGSF |
| 36 | EAAAREAAAR |
| 37 | EAAAREAAAREAAAREAAAR |
| 38 | ACGSLSCGSFACGSLSCGSF |
| 39 | ATSATATSAT |

Phosphorylation Domain and the Substrate Recognition Domain

The phosphorylation domain and the substrate recognition domain can be selected to be responsive to conditions present and specific for a phosphorylation reaction of interest (e.g., phosphorylation reactions in normal and diseases cells). In an embodiment, the phosphorylation domain and the substrate recognition domain are related to the insulin mediated phosphorylation system (e.g., phosphorylation peptide of insulin receptor substrate 1 and the SH2 substrate recognition domain of PI3Kinase). In addition, the phosphorylation domain in this case is a tyrosine residue and is phosphorylated by tyrosine kinase. Additional details are provided in Example 1.

In another embodiment, the phosphorylation domain and the substrate recognition domain can be selected to be responsive to conditions present and specific for detecting protein Akt kinase mediated phosphorylation events (e.g., using a specific phosphorylation domain and the phosphothreonione substrate recognition domain ($AKM_T$)). In this case the phosphorylation domain containing amino acid threonine is phosphorylated by the enzyme serine/threonine kinase. Additional details are provided in Example 2.

In another embodiment, the phosphorylation domain and the substrate recognition domain can be selected to be responsive to conditions present and specific for detecting protein kinase B (PKB) and protein kinase C (PKC) mediated phosphorylation events (e.g., using a specific phosphorylation domain and the phosphothreonione substrate recognition domain (FHA2)).

The phosphorylation domain corresponds to a peptide sequence that is responsive to conditions present and specific for a phosphorylation reaction of interest (e.g., a target protein that undergoes a phosphorylation reaction). In particular, the phosphorylation domain undergoes phosphorylation under conditions necessary for phosphorylation to occur in the target protein or the target substrate. For example, the phosphorylation domain may include a portion of a peptide sequence present in the target protein that is responsive to the phosphorylation conditions present to phosphorylate the target protein. The phosphorylation domain could also include other peptides bonded to one or more other components, for example.

Illustrative embodiments of phosphorylation domains include, but are not limited to, peptides corresponding to a portion of the insulin receptor substrate 1, peptides corresponding to a portion of the substrates related to detecting protein Atk kinase mediated phosphorylation events, peptides corresponding to a portion of the substrates related to detecting protein kinase B (PKB) and protein kinase C (PKC) mediated phosphorylation events, peptides corresponding to other kinases, and the like.

The substrate recognition domain binds with the phosphorylation domain upon phosphorylation of the phosphorylation domain. In an embodiment, the interaction of the phosphorylated phosphorylation domain and the substrate recognition domain is strong enough to cause the first linker peptide to bend or flex. In another embodiment, the interaction of the phosphorylated phosphorylation domain and the substrate recognition domain and the relative position of each of the first split protein and the second split protein hinder the interaction of the first split protein and the second split protein. The substrate recognition domain is selected based, at least in part, on the interaction of the phosphorylation domain and the substrate recognition domain, the strength of the interaction between the phosphorylation domain and the substrate recognition domain relative to the first linker peptide, and the like. For example, the substrate recognition domain will be selected from the protein to which a phosphorylated protein interacts. To increase the specificity of the process, the substrate recognition domain will be added on either side with flanking amino acids identified from the same protein.

TABLE 2 illustrates exemplary phosphorylation domain and substrate recognition domain combinations.

| Phosphorylation domain | Substrate Recognition domain |
|---|---|
| PI3Kinase-SH2 domain | Thr-Glu-Glu-Ala-Tyr-Met-Lys-Met-Asp-Leu-Gly-Pro-Gly (SEQ ID No. 40) |
| PI3Kinase-SH2 domain | Lys-Lys-His-Thr-Asp-Asp-Gly-Tyr-Met-Pro-Met-Ser-Pro-Gly-Val-Ala (SEQ ID No. 41) |
| FHA2-Phosphothreonine | RKRDRLGTLGI (SEQ ID No. 42) |
| FHA2-Phosphothreonine | RFRRFQTLKIKAKA (SEQ ID No. 43) |

Bioluminescence Initiating Compound

As mentioned above, the phosphorylation sensing system is used in conjunction with a bioluminescence initiating compound to produce a radiation emission. The bioluminescence initiating compound can include, but is not limited to, coelenterazine, analogs, and functional derivatives thereof, and D-luciferin analogs, and functional derivatives thereof. Derivatives of coelenterazine include, but are not limited to, coelenterazine 400a, coelenterazine cp, coelenterazine f, coelenterazine fcp, coelenterazine h, coelenterazine hcp; coelenterazine ip, coelenterazine n, coelenterazine O, coelenterazine c, coelenterazine c, coelenterazine i, coelenterazine icp, coelenterazine 2-methyl, and deep blue coelenterazine (DBC) (described in more detail in U.S. Pat. Nos. 6,020,192; 5,968,750 and 5,874,304). In an embodiment, the bioluminescence initiating compound can be D-luciferine when the bioluminescence compound is Firefly Luciferase.

In general, coelenterazines are known to luminesce when acted upon by a wide variety of bioluminescent proteins, specifically luciferases. Useful, but non-limiting, coelenterazines are disclosed in U.S. patent application Ser. No. 10/053,482, filed Nov. 2, 2001, the disclosure which is hereby incorporated by reference in its entirety. Coelenterazines are available from Promega Corporation, Madison, Wis. and from Molecular Probes, Inc., Eugene, Oreg. Coelenterazines may also be synthesized as described for example in Shimomura et al., Biochem. J. 261: 913-20, 1989; Inouye et al., Biochem. Biophys. Res. Comm. 233: 349-53, 1997; and Teranishi et al., Anal. Biochem. 249: 37-43, 1997.

Additional Methods of Use

In an embodiment, the phosphorylation sensor system and methods described herein can be used to monitor and assess biological interactions by modifying vector constructs (e.g., protein phosphorylation and the like) in a transgenic animal.

In another embodiment, a cell line or transgenic animal is marked with vector sets described herein that are developed utilizing coding regions of a sequence for the phosphorylation sensor system, for example, followed by optical imaging to image and/or quantitate phosphorylation related events in the presence and absence of molecules (e.g., pharmaceuticals) designed to modulate the interaction. As will be appreciated by the skilled practitioner, this technique will significantly accelerate drug validation by allowing testing in vivo.

In this regard, the present disclosure also includes transgenic animals comprising exogenous DNA incorporated into the animal's cells to effect a permanent or transient genetic change, preferably a permanent genetic change. Permanent genetic change is generally achieved by introduction of the DNA into the genome of the cell. Vectors for stable integration include plasmids, retroviruses and other animal viruses, YACS, and the like. Generally, transgenic animals are mammals, most typically mice.

The exogenous nucleic acid sequence may be present as an extrachromosomal element or may be stably integrated in all or a portion of the animal's cells, especially in germ cells.

Unless otherwise indicated, a transgenic animal includes stable changes to the GERMLINE sequence. During the initial construction of the animal, chimeric animals (chimeras) are generated, in which only a subset of cells have the altered genome. Chimeras may then be bred to generate offspring heterozygous for the transgene. Male and female heterozygotes may then be bred to generate homozygous transgenic animals.

Typically, transgenic animals are generated using transgenes from a different species or transgenes with an altered nucleic acid sequence. For example, a human gene may be introduced as a transgene into the genome of a mouse or other animal. The introduced gene may be a wild-type gene, naturally occurring polymorphism, or a genetically manipulated sequence, for example having deletions, substitutions or insertions in the coding or non-coding regions.

For example, an introduced transgene may include genes corresponding to a phosphorylation sensor system, which may become functional via complementation or reconstitution when exposed to appropriate test proteins or, alternatively, which may become non-functional when exposed to a particular test proteins that blocks phosphorylation. Such a transgene, when introduced into a transgenic animal or cells in culture, is useful for testing potential therapeutic agents known or believed to interact with a particular target protein implicated in a disease or disorder. Where the introduced gene is a coding sequence, it is usually operably linked to a promoter, which may be constitutive or inducible, and other regulatory sequences required for expression in the host animal.

Transgenic animals can be produced by any suitable method known in the art, such as manipulation of embryos, embryonic stem cells, etc. Transgenic animals may be made through homologous recombination, where the endogenous locus is altered. Alternatively, a nucleic acid construct is randomly integrated into the genome. Vectors for stable integration include plasmids, retroviruses and other animal viruses, YACS, and the like.

Numerous methods for preparing transgenic animals are now known and others will likely be developed. See, e.g., U.S. Pats. Nos. 6,252,131, 6,455,757, 6,028,245, and 5,766,879, all incorporated herein by reference. Any method that produces a transgenic animal expressing a reporter gene following complementation or reconstitution is suitable for use in the practice of the present invention. The microinjection technique is particularly useful for incorporating transgenes into the genome without the accompanying removal of other genes.

Kits

This disclosure encompasses kits that include, but are not limited to, a phosphorylation sensor system or vectors thereof; a bioluminescence initiating compound; and directions (written instructions for their use). The components of the present disclosure listed above can be tailored to the particular biological event to be monitored as described herein. The kit can further include appropriate buffers and reagents known in the art for administering various combinations of the components listed above to the host cell or host organism. The components of the present disclosure and carrier may be provided in solution or in lyophilized form. When the components of the kit are in lyophilized form, the kit may optionally contain a sterile and physiologically acceptable reconstitution medium such as water, saline, buffered saline, and the like.

EXAMPLE

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

In this system insulin binds to the insulin receptor and causes a conformational change in the intracellular domain, which is a tyrosine kinase. The tyrosine kinase then phosphorylates itself (autophosphorylation) on tyrosine residues, initiating a cascade of events leading to stimulation of glucose transport and mitogenesis. The tyrosine kinase specifically phosphorylates insulin receptor substrate 1 (IRS-1), and the phosphorylated region of IRS-1 binds to the SH2 domain of PI-3 Kinase (Event detected by the present disclosure).

FIG. 1 illustrates the insulin receptor pathway. The insulin receptor is a receptor tyrosine kinase (RTK). Unlike most RTKs, it exists as a dimer in the absence of ligand (Insulin). Binding of insulin can initiate two distinct signaling pathways (Ras dependent and Ras independent). Insulin receptor substrate 1 (IRS-1) binds to the activated insulin receptor via its PTB (Phosphotyrosine binding/Substrate peptide) domain and then is phosphorylated by the receptor's tyrosine kinase activity. Phosphorylated IRS-1 binds PI-3 kinase causing 10-fold stimulation in its kinase activity (SH2 domain/Recognition domain). This accounts for the rapid rise in phosphoinositides observed in insulin-stimulated cells. The increase in phosphoinositides leads to recruitment of protein kinase B (PKB) (also called Akt) to the cell membrane. After phosphorylated PKB is released into the cytosol, it mediates many effects of insulin (e.g., glycogen synthesis).

Phosphorylation Sensor for the Insulin Receptor Substrate 1 (IRS-1) Based on Split Reporter Complementation.

Figure 2:
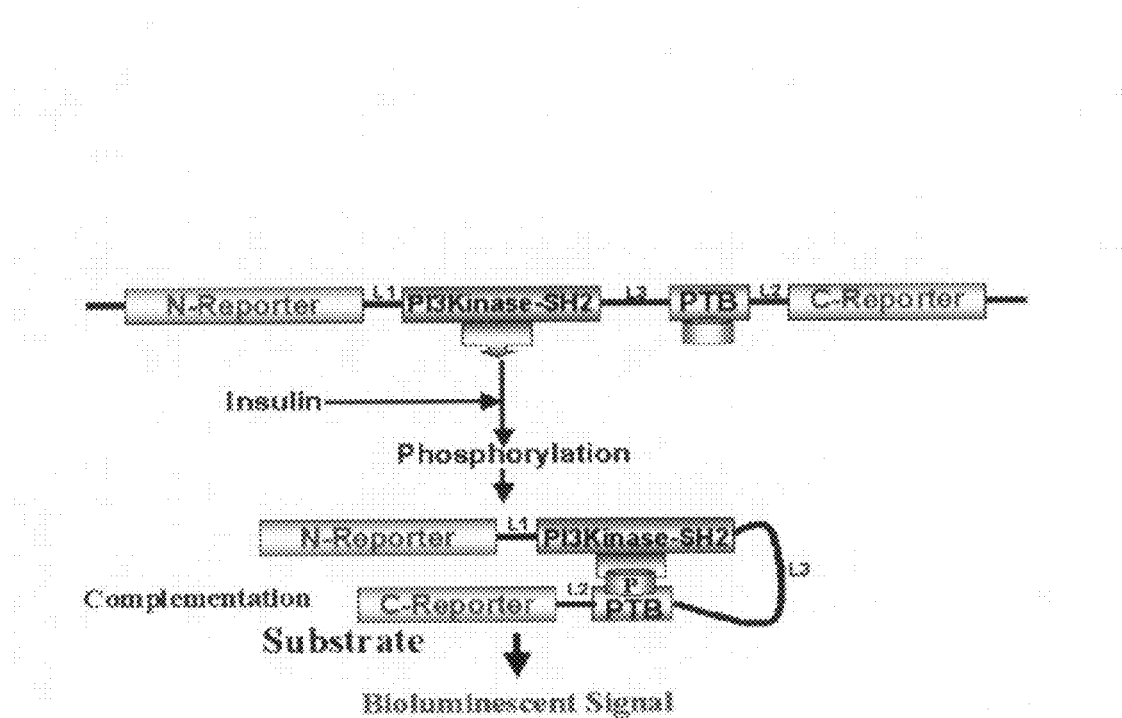
FIG. 2 illustrates the phosphorylation sensor for the insulin receptor substrate 1 (IRS-1).

The insulin receptor pathway has been extensively studied. A vector was constructed and is shown in the FIG. 2, in which phosphorylation of the PTB peptide should lead to split reporter complementation. A semi-rigid linker peptide keeps the split reporter fragments in the fusion system away from each other unless a forced interaction (in this case, phosphorylation) occurs.

This phosphorylation sensor is designed to sense the phosphorylation status of the insulin receptor substrate 1 (IRS-1). If IRS-1 is phosphorylated, so will the PTB peptide in the sensor, in turn causing the SH2 domain of the PI3 Kinase to bind to PTB. This interaction of PI3 Kinase-SH2 and PTB leads to complementation of the split reporters of choice. Complementation of the split reporters can be detected by light production in the presence of the appropriate substrate. The choice of linker (L3) helps to minimize signal prior to PTB being phosphorylated. See also FIG. 1 for insulin receptor pathway.

The IRS-1 phosphorylation sensor was tested based on split *renilla* and split Firefly Luciferase in transient transfection assays in cell culture with and without insulin. The single fusion vector (FIG. 2) was utilized with split *Renilla* Luciferase (split site 229, non-self complementing), with a semi-rigid peptide ((EAAAR)$_2$ (SEQ ID NO: 36)) through screening of different peptides. The phosphorylation domain was the PTB peptide and was chosen to be an 13 amino acid peptide (SEQ ID NO: 28) including Y941 (tyrosine at position 941 of IRS-1). The substrate recognition domain was chosen to be the SH2 domain of PI3 Kinase. The vector constructed was transiently transfected in CHO-IR (expressing the insulin receptor) and 293T cells (not expressing the insulin receptor). The results show insulin dependent recovery of *Renilla* Luciferase signal in the CHO-IR cells.

Figure 3:
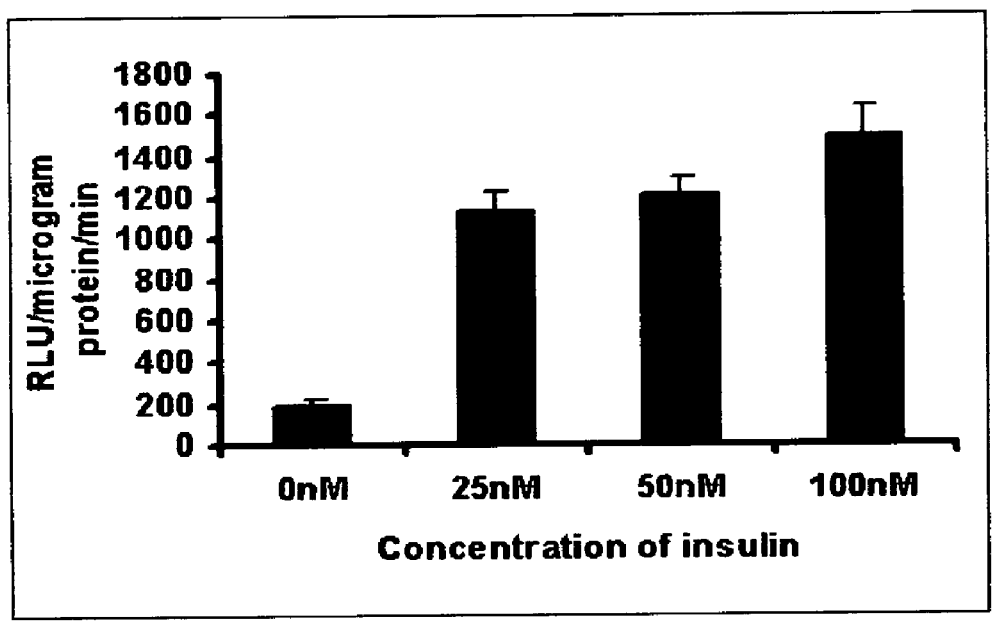
FIG. 3 is a graph of the activation of the *Renilla* Luciferase based IRS-1 phosphorylation sensor as a function of Insulin concentration. Luminometer assay result of CHO-IR cells transfected with a phosphorylation sensor vector and assayed after 24 h of incubation with the addition of different concentrations of insulin (0, 25, 50 and 100 nM). The result shows concentration dependent increase in complemented *Renilla* Luciferase activity.

Next, constructs were made using self-complementing split fragments of Firefly Luciferase with a semi-rigid linker or without any linker, and these were compared with two separate vectors (non-fusion approach) in CHO-IR cells in the presence and absence of insulin (FIG. 3). The results of these studies show signal from all three vectors in the presence of insulin, but the highest absolute signal is from the two fusion vectors. Furthermore, for the two fusion vectors the background signal is lowest (prior to insulin exposure) when using the fusion vector with a semi-rigid linker.

Figure 4:
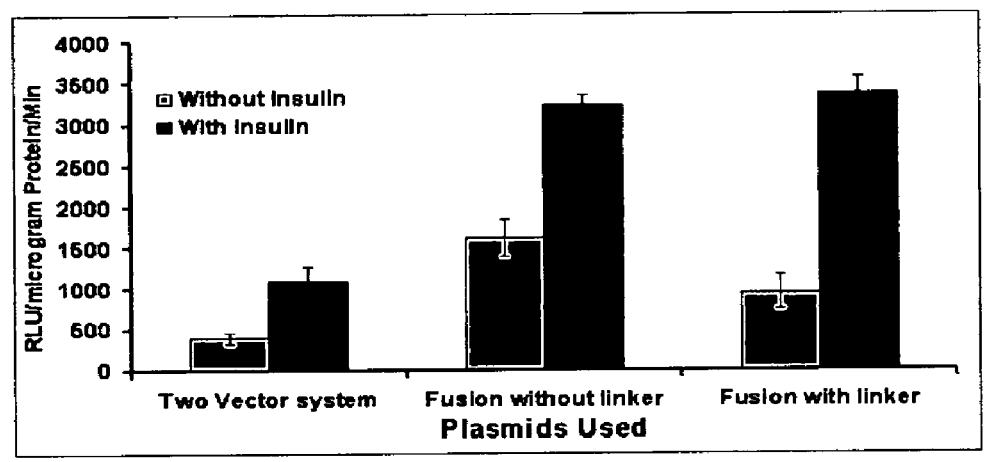
FIG. 4 is a graph of the activation of the Firefly Luciferase based IRS-1 phosphorylation sensor as a function of Insulin exposure. Results of CHO-IR cells transfected and co-transfected with a self-complementing Firefly Luciferase based IRS-1 sensor used for studying insulin mediated IRS-1 phosphorylation. A two-vector system, single fusion vector with and without a semi-rigid linker were all compared. Greater absolute signal is seen with the fusion vector strategies.

The results shown in FIG. 4 demonstrate that a split-reporter based phosphorylation sensor for IRS-1 based on split bioluminescence reporters is capable of producing increased signal in the presence of insulin as compared to no insulin exposure. The fusion strategy increases absolute signal as compared to using two separate vectors. Furthermore, using a semi-rigid linker decreases background signal in the fusion vector strategy. Finally, the absolute signal from the split Firefly Luciferase based vectors is higher than that from the split *Renilla* Luciferase based vectors under the specific conditions tested.

Testing the Firefly-Luciferase Based Phosphorylation Sensor for the Insulin Receptor Substrate 1 (IRS-1) Using Transiently Transfected CHO-IR Cells Implanted in Living Mice.

Figure 5:
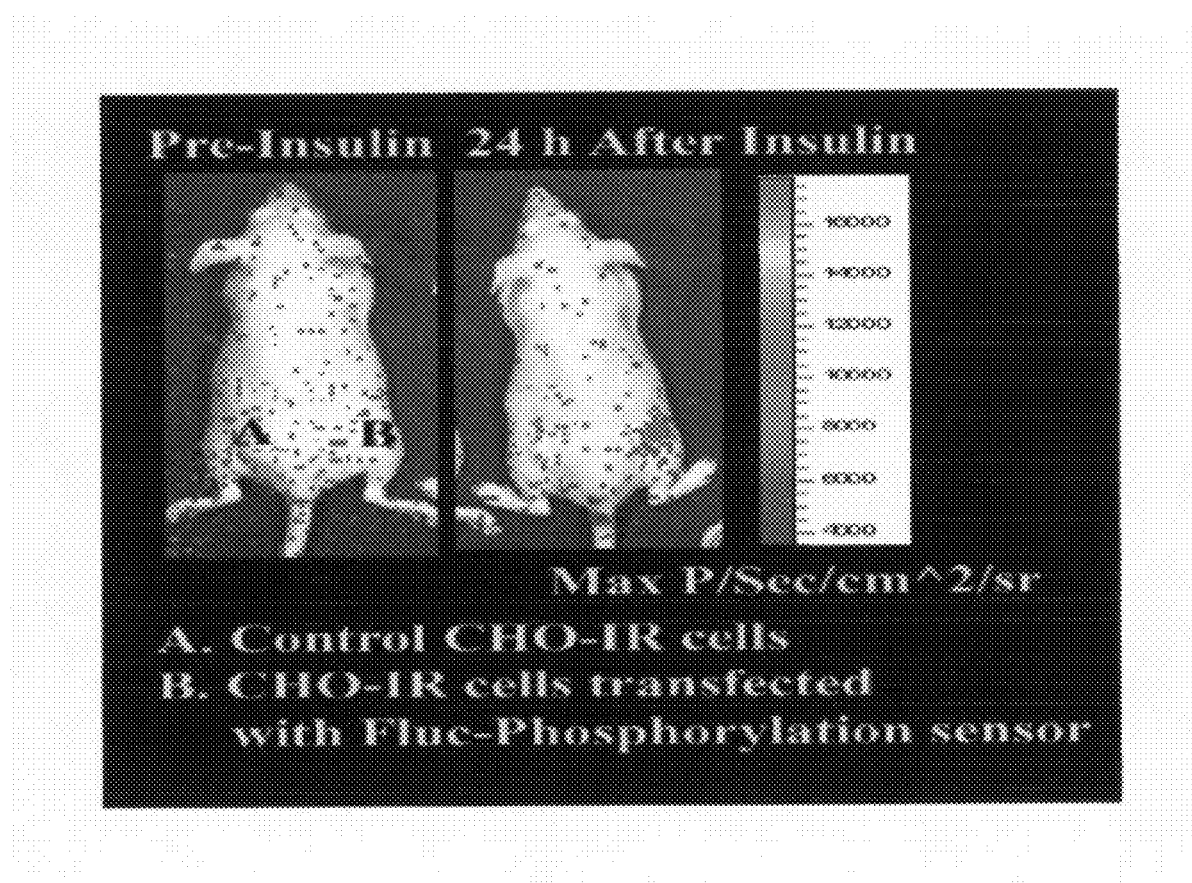
FIG. 5 illustrates a bioluminescence CCD imaging of a split Firefly Luciferase based Insulin Receptor Substrate 1 (IRS-1) phosphorylation sensor in a living mouse. Five million CHO-IR cells transiently transfected with the split Firefly Luciferase phosphorylation sensor were implanted at site B and mock transfected cells at site A. Imaging of the animal prior to insulin shows low background signal and after exposure to insulin site B shows marked increase in signal likely reflecting the insulin mediated activation of insulin receptor as reflected by complementation of the phosphorylation sensor.

Four nude mice were implanted with 5 million CHO-IR cells transiently transfected with the fusion split firefly IRS-1 phosphorylation sensor with linker (EAAAR)$_2$ and also with 5 million CHO-IR mock-transfected cells at two separate sites. The mice were imaged using D-Luciferin (3 mg i.p.) with a CCD camera. Two mice were then given 4 IU human long-acting insulin (s.c.) in twelve hour intervals, and two were not given insulin and all four were imaged again 24 hours later. Results from one mouse imaged pre- and post-insulin are shown in FIG. 5. Consistent results were obtained in the 2 mice in each group with exposure to insulin leading to an increase in signal (~5-fold induction) and lack of insulin exposure leading to minimal change (~1.3 fold induction).

Example 2

Introduction

Protein kinases play a crucial role in cancer initiation, progression and metastasis since they are often over-expressed and/or constitutively active. One prime example is Akt, which is a 57 kDa serine/threonine kinase that is highly activated (phosphorylated) in multiple human cancers, including breast, prostate, ovarian, pancreatic, colon, lung and brain cancers as well as lymphoma, melanoma. Upregulation of Akt phosphorylation correlates with tumor metastasis, and resistance to chemotherapy and radiation therapy. Akt is activated by the phosphatidylinositol-3-kinase (PI-3K) pathway and becomes fully activated upon phosphorylation at $T^{308}$ and $S^{473}$. Phosphorylated Akt translocates from the plasma membrane to the different subcellular locations, where it phosphorylates multiple substrates that are crucial in cell cycle progression, protein synthesis, survival, glucose metabolism and inhibition of apoptosis, at their Akt kinase motif (AKM): RxRxxS/T.

Investigation of Akt kinase activity is usually limited to in vitro analyses such as kinase assays, western blotting using phosphorylation-specific antibodies and cell cytotoxicity assays. These assays can be labor intensive, invasive in nature and affected by the strength of the detergent, which may not reflect the nature of Akt kinase activity in intact cells. Genetically encoded fluorescence reporters have been recently developed to monitor Akt kinase activity in intact cells, including the B kinase activity reporter (BKAR) and Aktus. These reporters monitor Akt kinase activity based on the increase in fluorescence resonance energy transfer (FRET) ratios mediated by the interactions between the phosphorylated human AKM and the yeast FHA2 or phosphothreonine binding domain from human 14-3-3ε protein. Although these reporters provide single cell resolution of Akt kinase activity, these small changes in FRET ratios (maximum of 1.3-fold increase over carrier control treated cells) cannot be easily adapted for small living animal imaging due to the high background fluorescence. Unlike under in vitro and cell culture conditions, the efficacies of Akt inhibitors are limited by their pharmacokinetic properties, including solubility, toxicity, drug delivery and metabolism, as well as cell-cell and cell-extracellular matrix interaction. Although some of these Akt inhibitors have shown efficacy for growth inhibition in cell culture and xenograft models in living mice, their pharmacodynamic properties (i.e., inhibition of Akt kinase activity) have not been directly validated.

To overcome the limitations in studying protein-protein interactions within intact cancer cells in their native tumor microenvironment, the split luciferase protein-fragment-assisted complementation (SL-PFAC) technology for non-invasive monitoring of protein-protein interactions has been developed and validated, both in cell culture and in living mice by optical bioluminescence imaging. SL-PFAC is based on the complementation of two inactive halves on the full length luciferase mediated by the interaction between two positively interacting proteins. The two major luciferases that have been extensively utilized to date are the Firefly Luciferase (FL, 65 kDa) and *Renilla* Luciferase (RL, 36 kDa). FL has been split to yield the N-terminal fragments comprised of amino acids (aa 1-437, 2-435, 21-550, 2-416, SEQ ID No: 33) and the C-terminal fragments comprised of aa 438-550, 21-550, 398-550, 394-550 (SEQ ID No: 33) in the SFL-PFAC system for monitoring the interactions between 14-3-3ε/Cdc25, Stat1 dimerization in cell culture studies and Rapamycin-mediated mTOR kinase/FKBP12 immunophillin, Id/myoD, Hif1-aNHL, TK/TK, ER/ER, ER-folding either in cell culture or in both cell culture and in living mice. Similarly, *Renilla* Luciferase (RL) has also been rationally split for adaptation for SL-PFAC system as SRL-PFAC in cell culture and living mice.

Figure 6A:
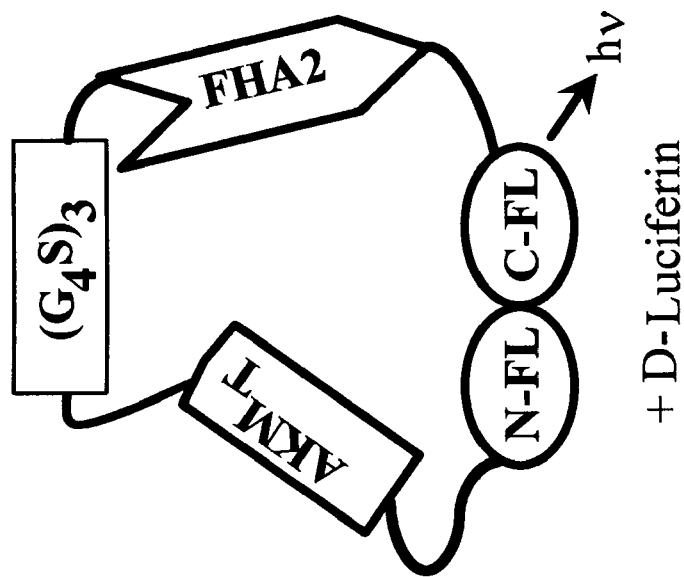
FIG. 6a illustrates a schematic diagram for Akt kinase sensor (AS1T). Inhibition of Akt kinase activity by PI-3K/Akt inhibitors leads to decreased phosphorylation of AS1T at the Akt kinase motif ($AKM_T$) and interaction with the phosphothreonine binding domain (FHA2), which leads to increased complementation of split FL fragments (N-FL and C-FL) and light production in the presence of the FL substrate D-Luciferin. On the other hand, activation of Akt kinase activity (by PI-3K/AKT-P) leads to phosphorylation of AS1T at the $AKM_T$ and increased interaction with FHA2, thus hinders complementation between NFL and CFL. The AS1A sensor with a non-phosphorylatable $AKM_A$ motif served as a negative control.
Figure 6A:
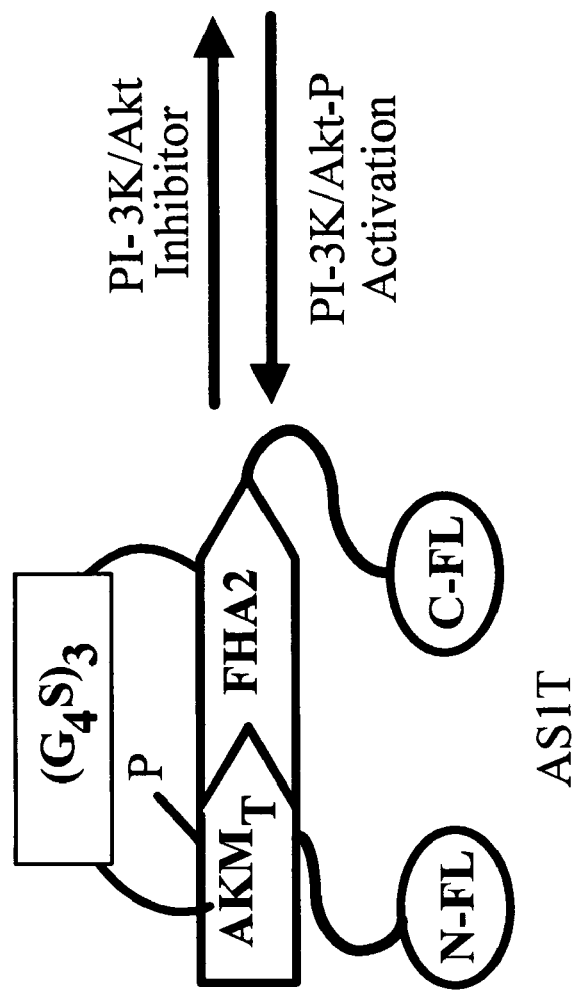

To indirectly monitor Akt kinase activity in intact cells in cell culture and non-invasively in living mice, the present disclosure postulates: 1) the AS serves as a pseudo substrate for activated Akt; 2) upon interaction between the phosphorylated Akt kinase motif (AKM) and the phoshothereonine binding domain (FHA2), complementation of split FL should be hindered; and 3) inhibition of Akt kinase activity should led to reduced interaction between AKM and FHA2 should lead to increase in split FL complementation in the sensor and subsequent complementation of split FL activity leads to signal amplification in the presence of its substrate D-Luciferin (FIG. 6a).

In this example, AS is used to indirectly examine the kinetics of Akt kinase activity and monitored the efficacy of known PI-3K and Akt kinase inhibitors in disruption of these interactions first in cell culture. This was followed by validation of the drug mechanism in living mice by non-invasive, repetitive imaging of the same mouse that allows dynamic indirect monitoring of Akt kinase activity in response to treatment.

Akt kinase is a serine/threonine kinase that is highly activated in human cancers and involved in resistance in cancer progression and resistance to therapy. Using a novel split Firefly Luciferase complementation system, the Akt kinase activity in response to different phosphoinositide-3-kinase (PI-3K) and Akt kinase inhibitors were indirectly monitored in cell culture and non-invasively in living mice. Inhibition of Akt kinase activity was further confirmed by in vitro Akt kinase assay and phosphorylation-specific western blotting while the specificity of the sensor was confirmed using a non-phosphorylatable mutant sensor. Molecular imaging of Akt kinase activity in living subjects with pharmacological modulation has been achieved and can be extended for studying the biology of different kinases and development of novel kinase inhibitors.

Results

Akt Kinase Sensor (AS1T) is a Genetically-Encoded Reporter Based on Complementation of Split FL Fragments Upon Akt Dephosphorylation AS1T was constructed using the overlapping split sites of N-terminus (N-FL, aa 1-416 (SEQ ID NO: 33)) and C-terminus (C-FL. aa 394-550 (SEQ ID NO: 33)) of FL (In; 2346-2353, which is incorporated herein by reference). The Akt kinase motif (AKM) peptide sequence (RKRDRLGTLGI, SEQ ID NO: 31) and the yeast phosphothreonine FHA2 binding domain [previously used for the fluorescence-based Akt phosphorylation reporter (Journal of Biological Chemistry 280:5581-5587, which is incorporated herein by reference)] were cloned in between the NFL and CFL. A corresponding AS with the non-phosphorylable AKM (RKRDRLGALGI, SEQ ID NO: 42) containing an alanine substitution (AS1A) was used as a negative control. The AKM and FHA2 domains were connected by a flexible $(G_4S)_3$ peptide linker. FIG. 6a shows the configuration of the AS1T and AS1A. It is hypothesized that activation of Akt kinase activity results in phosphorylation of AS1T at the AKM. Subsequent interaction with the FHA2 hinders complementation between the N- and C-terminus of split FL. Inhibition of Akt kinase activity by PI-3K/Akt kinase inhibitors leads to inhibition of Akt kinase activities and reduces phosphorylation of AKM in AS1T. Subsequently, this leads to decreased interactions between AKM and FHA2 and increases complementation of NFL and CFL and higher levels of complemented FL activity. On the other hand, complemented AS1A with the non-phosphorylatable AKM should not be affected by the status of Akt kinase activity.

AS was Sensitive and Specific for Monitoring Akt Kinase Activity in Cell Culture Studies.

The sensitivity of AS1T was first tested in BT474 human breast ductal carcinoma cells, which exhibit constitutively active Akt kinase activity. To test the hypothesis that inhibition of PI-3K pathway and subsequent Akt kinase activity leads to increase in split FL complementation in AS1, BT474 cells were transiently transfected with AS1T or AS1A in the presence of different concentrations of LY294002 (LY, a PI-3K inhibitor that inhibits Akt activation) or carrier control for 24 hours. FL activity was determined by luminometer assays using cell lysates and normalized for protein content and transfection efficiency. LY treatment of BT474 cells transiently transfected with AS1T led to a dose dependent increase in FL activity in (1.3-fold maximum increase, $p<0.05$ at 50 µM, relative to carrier control treated cells). On the other hand, in BT474 cells transiently transfected with the non-phosphorylable AS1A, there was no significant increase in complemented FL activity ($p>0.05$) (FIG. 6b).

Figure 6C:
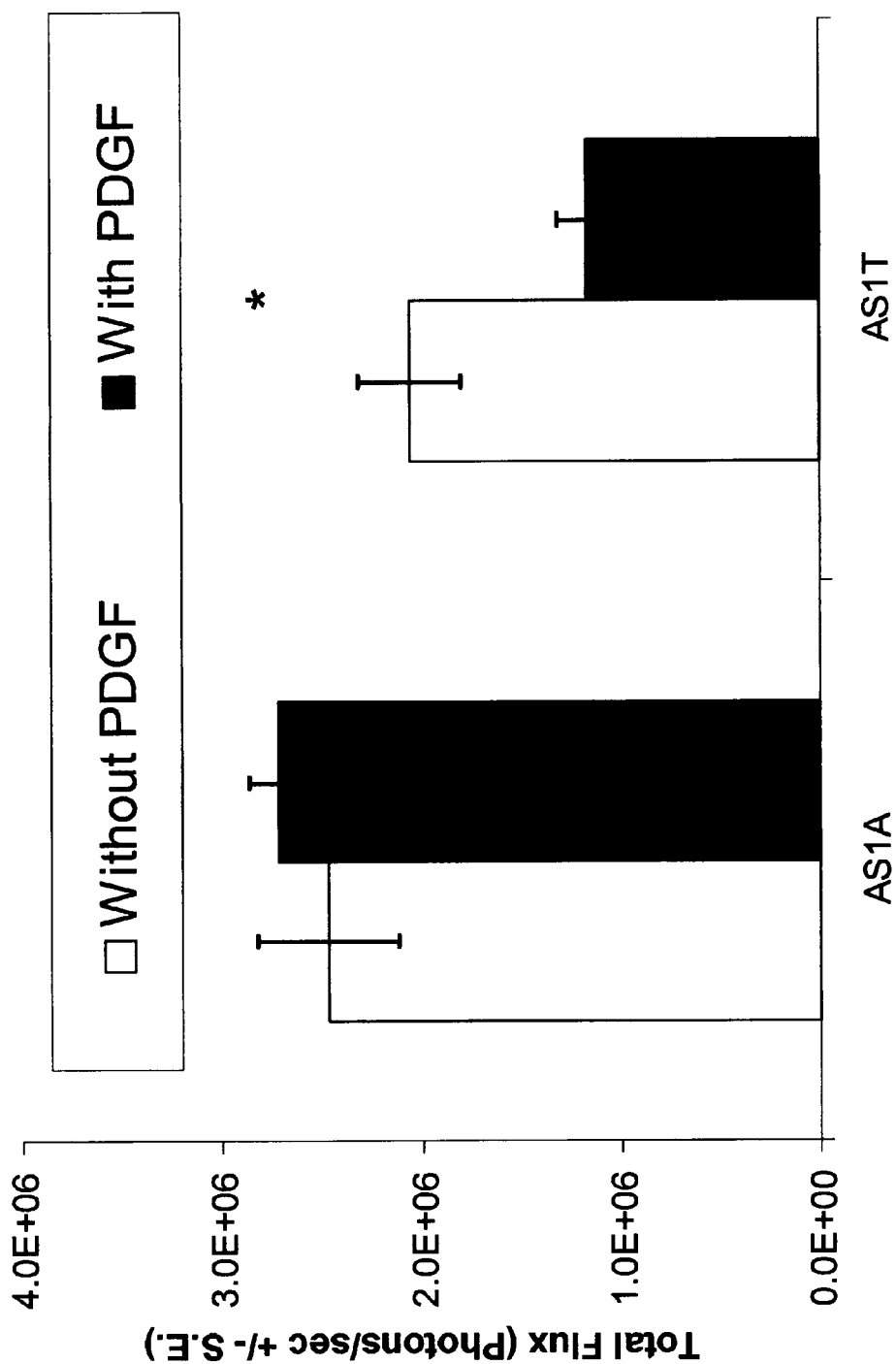
FIG. 6c illustrates the activation of Akt kinase activity by platelet derived growth factor (PDGF) led to decrease in complemented FL activity. 293T cells transiently transfected with AS1A or AS1T for 24 hours were treated with PDGF or carrier control for 30 mins prior to analysis of complemented FL activity as described in FIG. 6b. In 293T cells transiently transfected with AS1T, PDGF led to decrease in complemented FL activity. On the other hand, in 293T cells transiently transfected with AS1A, PDGF did not lead to significant decrease in complemented FL activity. It should be noted that $p<0.05$ relative to carrier control treated cells.

Next the hypothesis that activation of Akt activity would lead to increased phosphorylation of AKM and interaction with FHA2 in AS1T was tested, and subsequent inhibition of split FL complementation. 293T cells transiently transfected with AS1T and AS1A were treated with platelet derived growth factor (PDGF) for 30 minutes prior to analysis of FL activity. A 60% decrease in FL activity was seen in 293T cells transiently transfected with AS1T and treated with PDGF, compared to that of carrier control treated transfected cells ($p<0.05$) (FIG. 6c). PDGF treatment did not significantly decrease FL activity in 293T cells transiently transfected with AS1A ($p>0.05$), thus AS1T can be used to monitor the both activation and inhibition of Akt kinase activity.

Differential Kinetics of PI-3K Inhibitor LY294002 and Akt Kinase Inhibitor Perifosine on Complemented FL Activity.

Figure 7A:
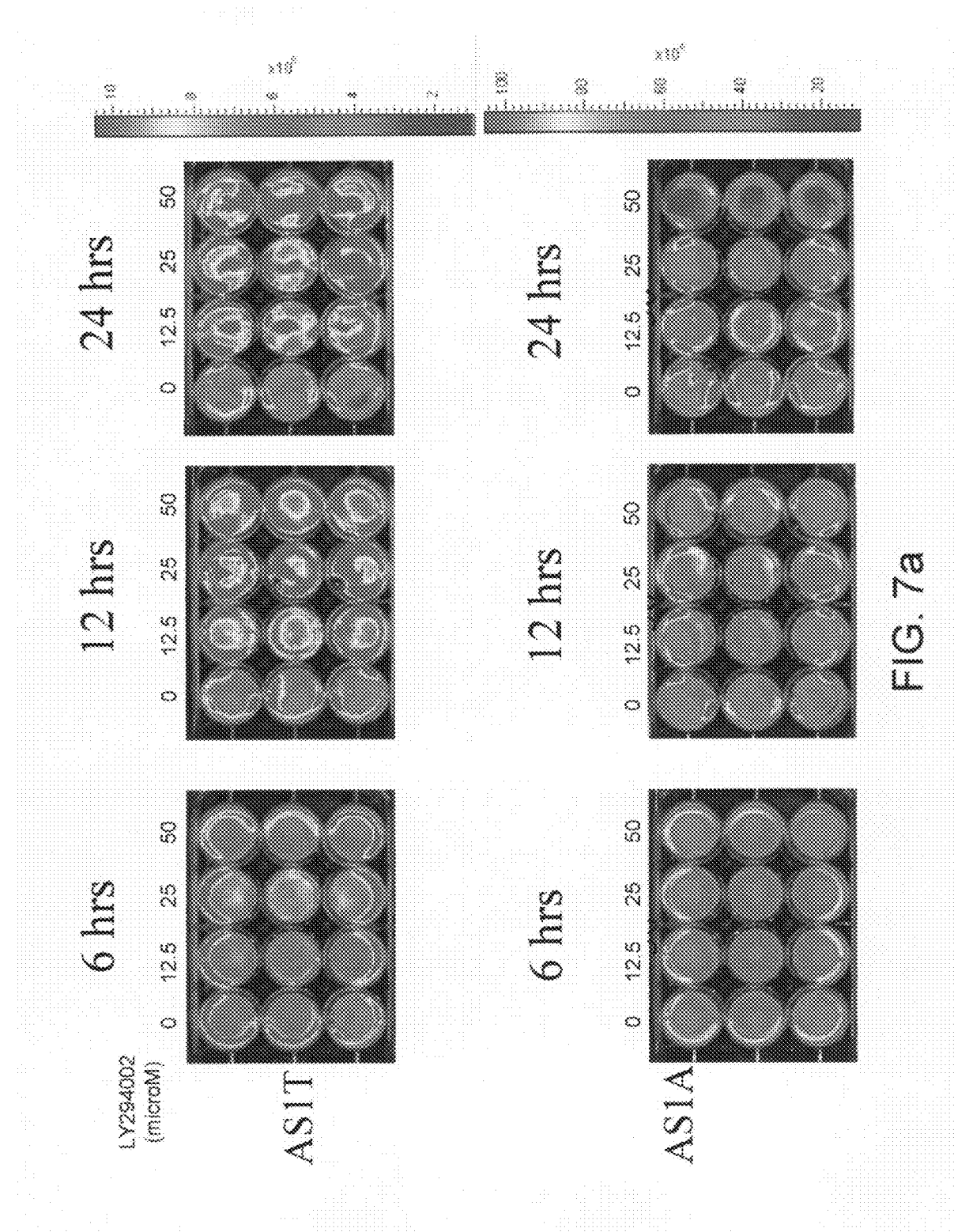
FIGS. 7a-7d illustrates the differential temporal- and dose-dependent increase in complemented FL activity by the PI-3K inhibitor LY294002 (LY) and Akt kinase inhibitor perifosine in 293T cells stably transfected with AS1A (293T/AS1A) or AS1T (293T/AS1T).
Figure 7B:
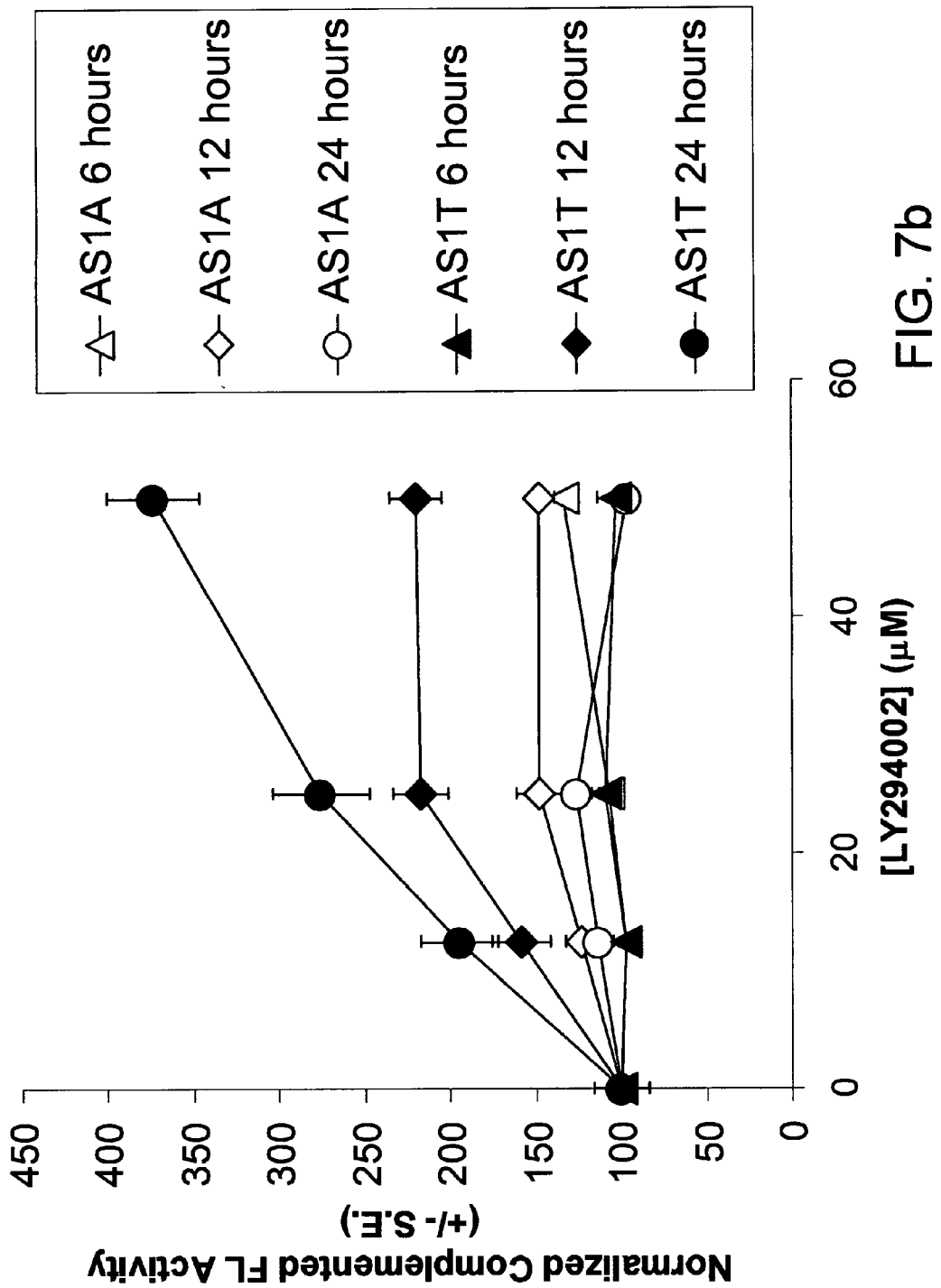

To circumvent the changes in expression of AS1A and AS1T in transient expression studies, 293T cells stably transfected with AS1T (293T/AS1T) or AS1A (293T/AS1A) were used for subsequent studies. To determine the kinetics and dynamic range of using AS1T to indirectly monitor the effect of LY (an upstream inhibitor) on inhibition of Akt kinase activity, 293T/AS1T and 293T/AS1A cells were treated with different concentrations of LY or carrier control (1% DMSO) for 6, 12 and 24 hours. Complemented FL activity at each time point was determined by bioluminescence imaging of intact cells by addition of D-luciferin (FIG. 7a), prior to normalization for protein content (FIG. 7b). LY treatment led to a dose-dependent increase in complemented FL activity for 293T/AS1T at 12 and 24 hours ($p<0.05$ at all LY concentrations) but not at 6 hours ($p>0.05$), compared to that of 293T/AS1A cells. Furthermore, the complemented FL activity in untreated 293T/AS1A cells was 10-fold higher than that of 293T/AS1T cells at all time points.

Figure 7C:
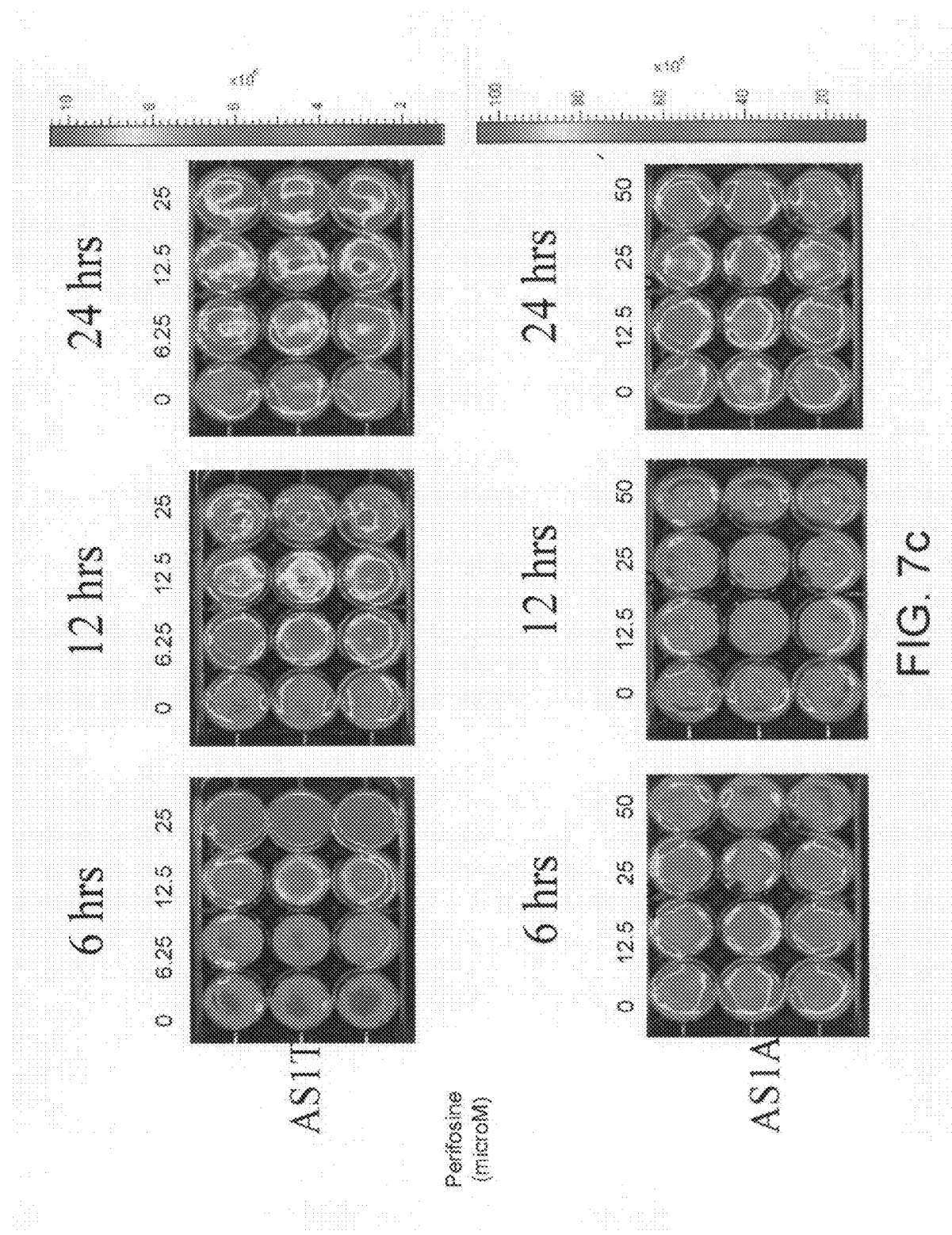
Figure 7D:
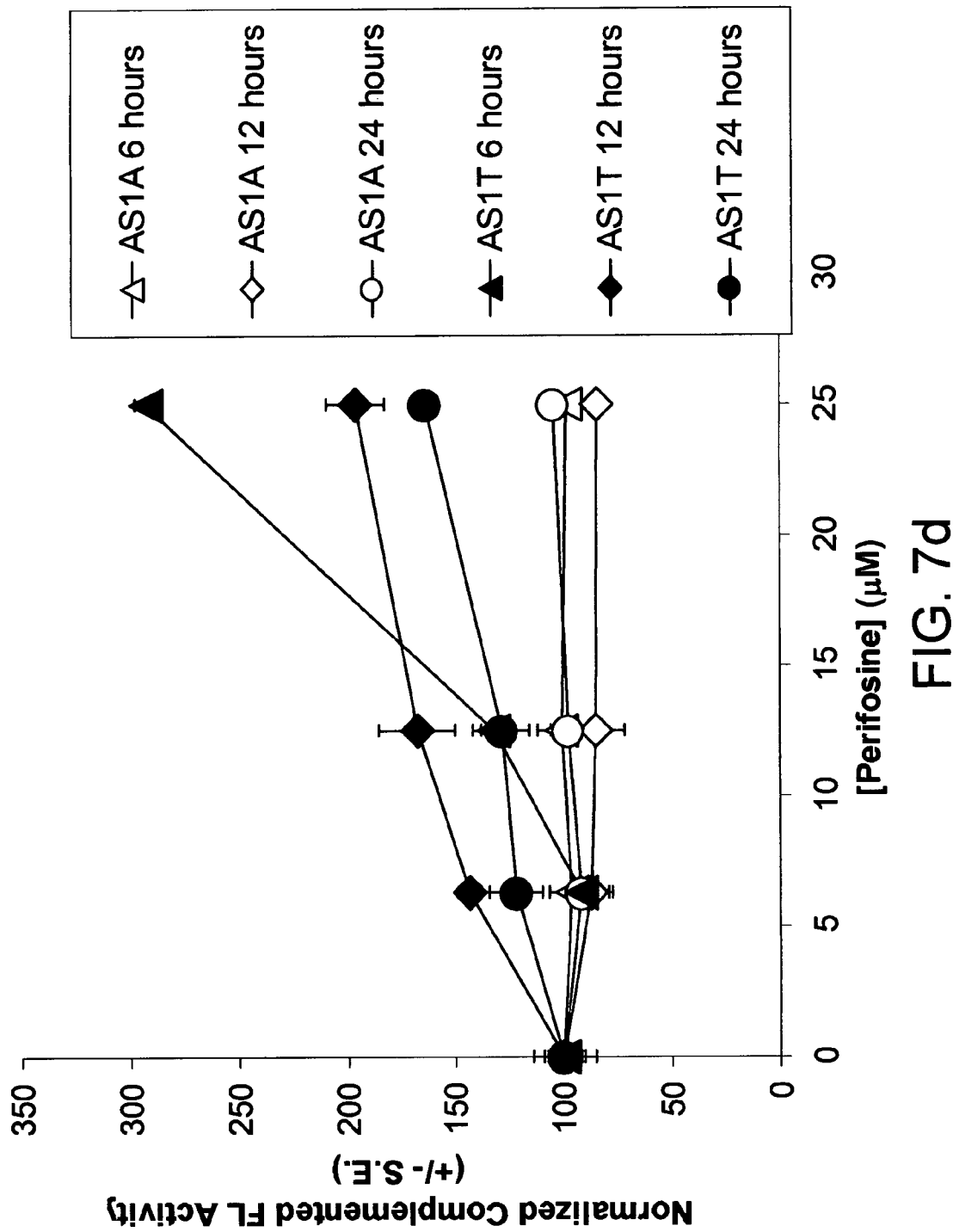

To determine if AS1T can also be used to evaluate the efficacy of Akt kinase inhibitor perifosine, 293T/AS1T and 293T/AS1A cells were treated with different concentrations of perifosine or carrier control (0.8% ethanol) for 6, 12 and 24 hours prior to imaging of complemented FL activity (FIG. 7c) and normalization of protein content, as described above for LY. FIG. 7d shows that perifosine treatment led to a dose-dependent increase in complemented FL activity for 293T/AS1T at all time points and concentrations tested, compared to that of 293T/AS1A cells ($p<0.05$). Furthermore, maximum increase in complemented FL activity in 293T/AS1T cells occurred at 6 hours, compared that of 24 hours for LY treated 293T/AS1T cells. All together, our data suggests AS1T was sensitive and specific for indirect monitoring of Akt kinase activity in intact cells in response to different PI-3K/Akt kinase inhibitors.

AS1T was Validated for Indirect Monitoring of Akt Kinase Activity.

Figure 8A:
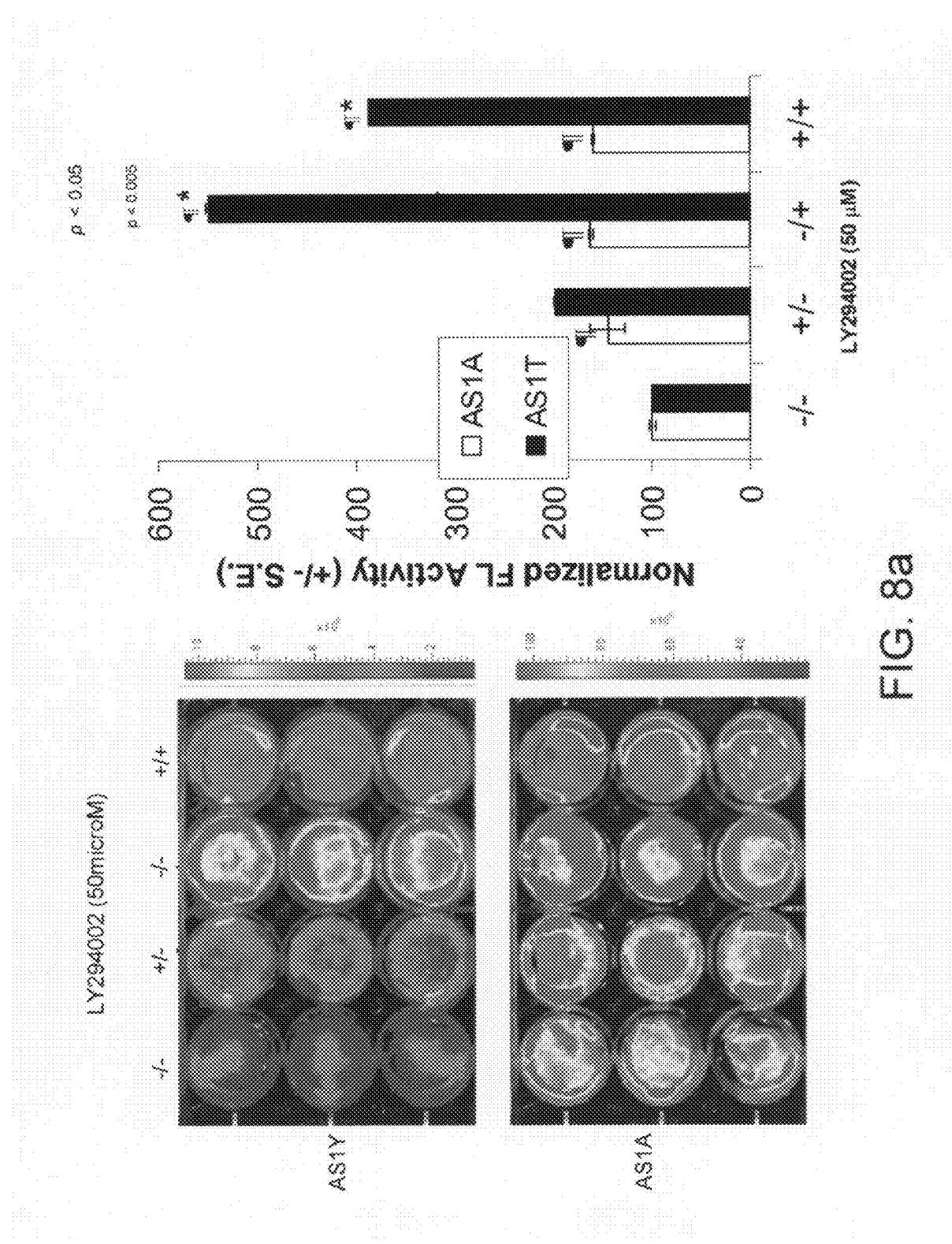
FIG. 8a-8b illustrates the validation of AS1T for indirect imaging of Akt kinase activity in cell culture studies.

To determine the reversibility of AS1T to inhibition of Akt kinase activity by LY and perifosine, 293T/AS1T and 293T/AS1A cells were first treated with LY (24 hours), perifosine (6 hours) or their respective carrier controls that allows maximum induction of complemented FL activity. This was followed by washout and replacement of medium with the same concentrations of LY, perifosine or carrier controls for the same period of time (24 hours for LY and 6 hours for perifosine), prior to determination of complemented FL activity as described above. 293T/AS1A and 293T/AS1T that were first treated with carrier control then with LY (24 hours) or perifosine (6 hours) served as negative and positive controls for the treatment, respectively. FIG. 8a shows that complemented FL activity in 293T/AS1T cells that were treated with LY followed by incubation with carrier control was substantially lowered than that of 293T/AS1T cells that were first treated with carrier control and then with LY ($p<0.05$) or with LY294002 for the entire 48 hours ($p<0.05$). The complemented FL activity in 293T/AS1T cells treated with carrier control first followed by LY, or with LY for the entire 48 hours was also higher than that of corresponding 293T/AS1A cells ($p<0.05$). Furthermore, there was no significant differences between all LY treated 293T/AS1A cells ($p>0.05$). Similar results were seen with perifosine, in which the complemented FL activity in 293T/AS1T cells treated with perifosine followed by carrier control was significantly lower than that of cells treated with carrier control first then with perifosine (p<0.001), or 293T/AS1T cells that were treated with perifosine for 12 hours total (p<0.05).

Figure 8B:
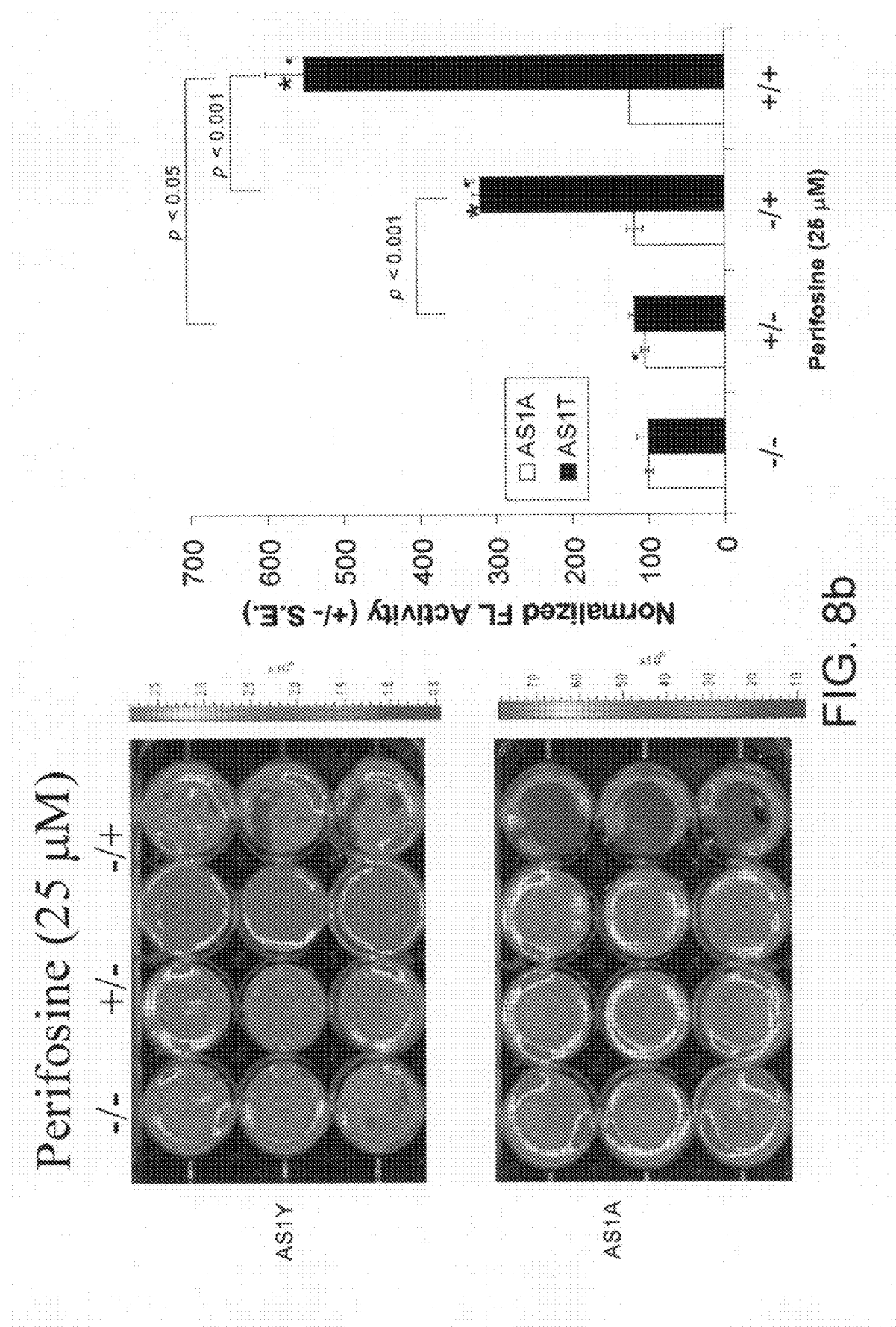
Figure 9A:
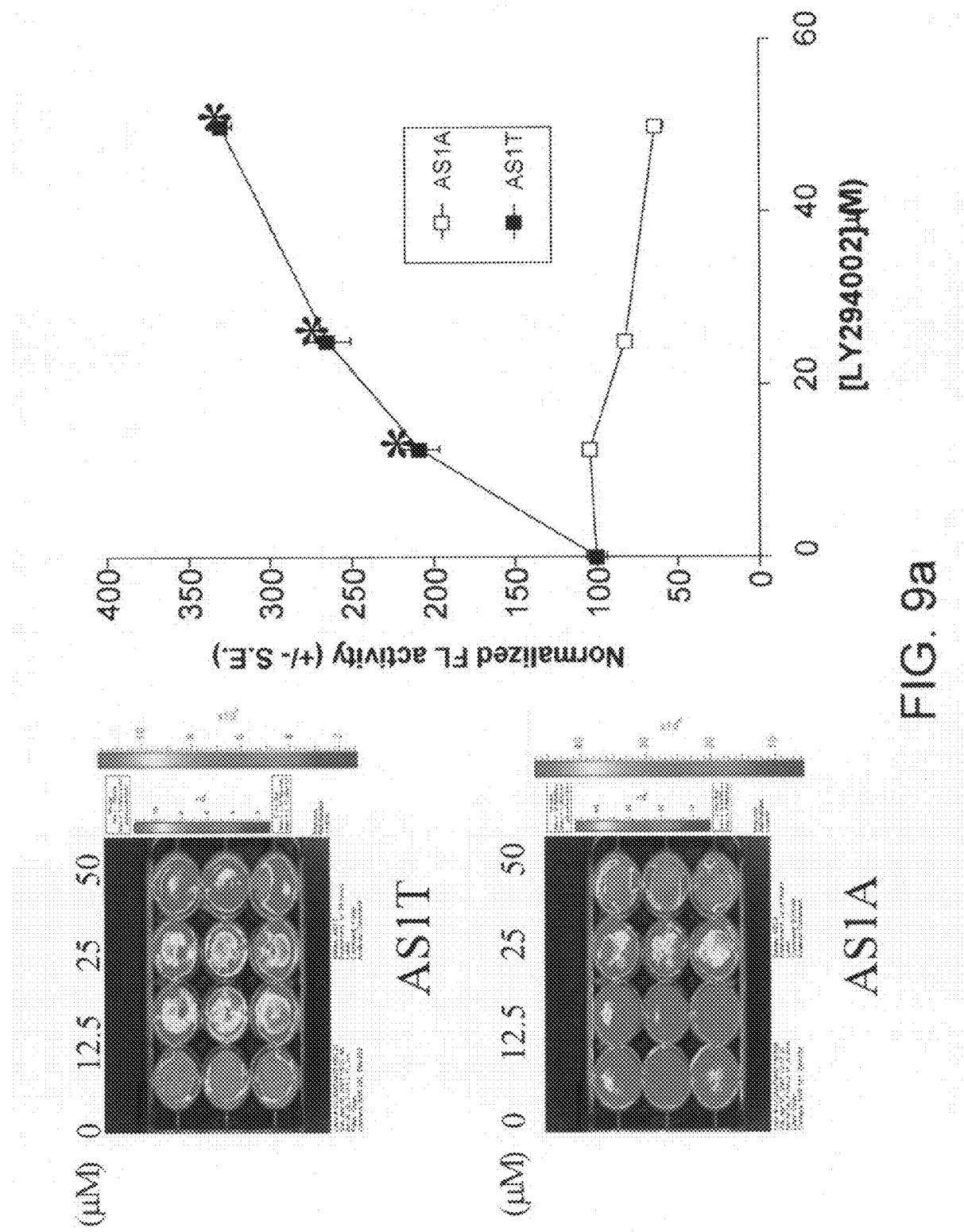
FIGS. 9a-9d illustrate the increase in complemented FL activity corresponded to decrease in endogenous Akt phosphorylation and kinase activities in 293T/AS1T cells but not in 293T/AS1A cells.
Figure 9B:
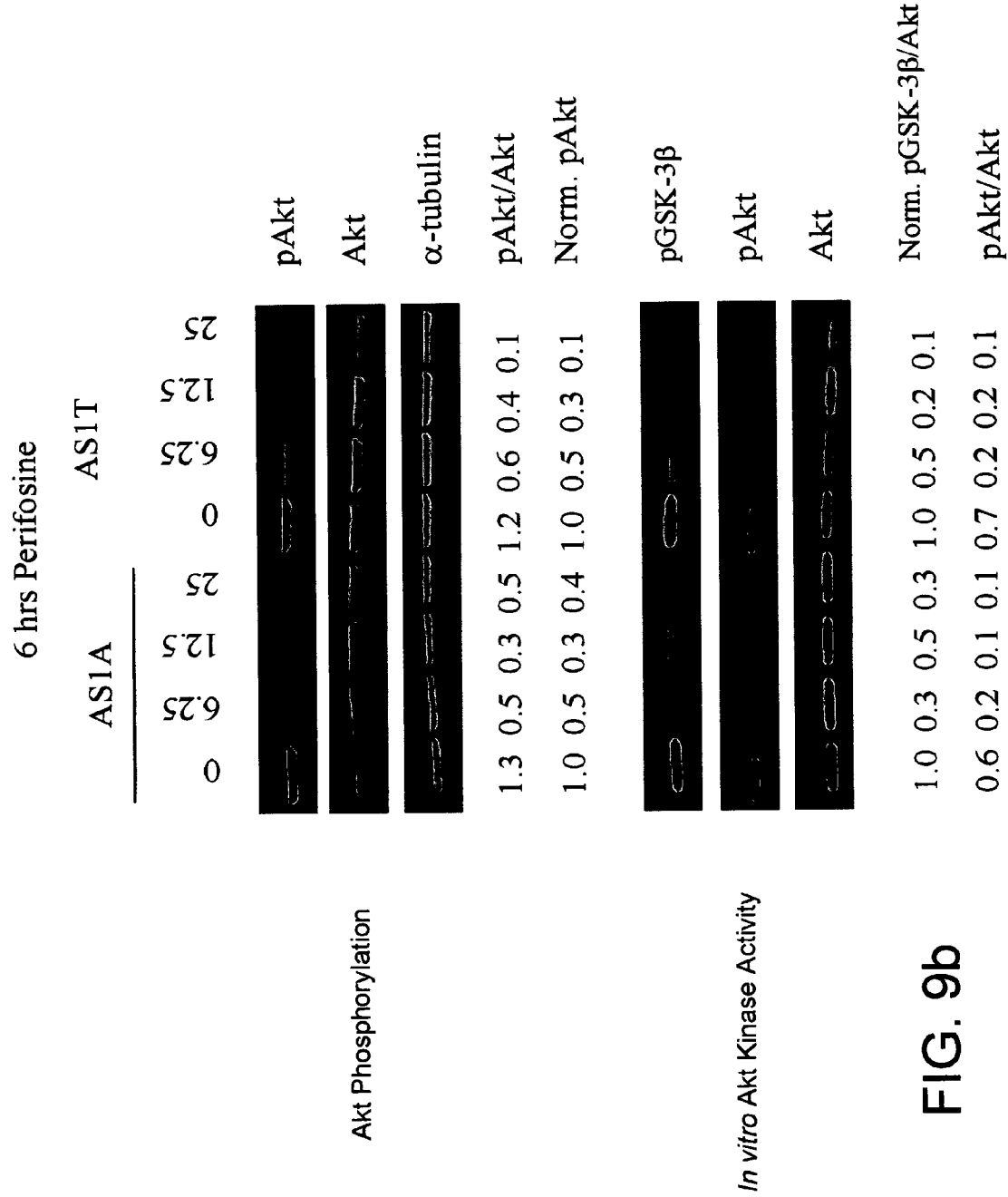
Figure 9C:
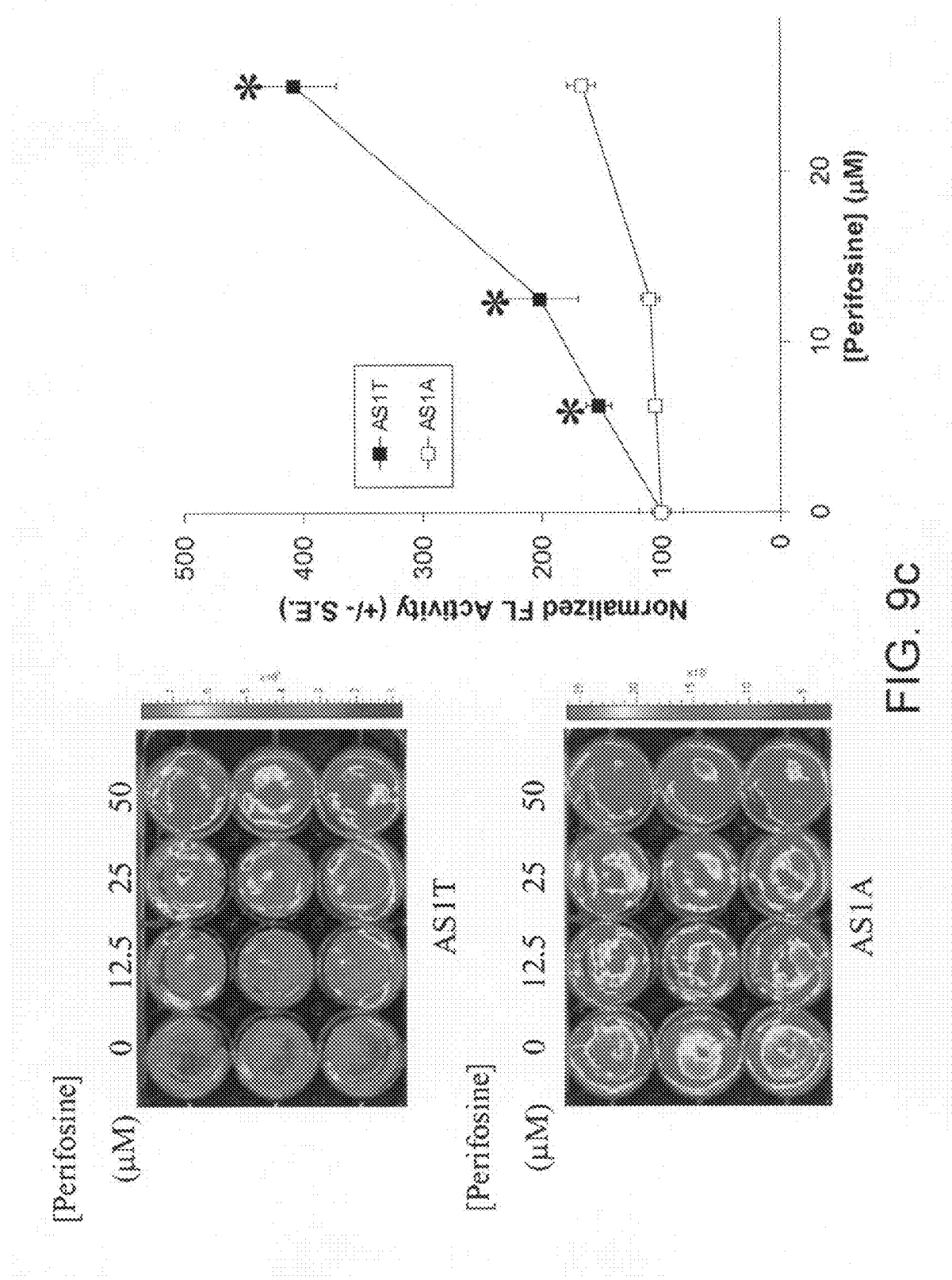
Figure 9D:
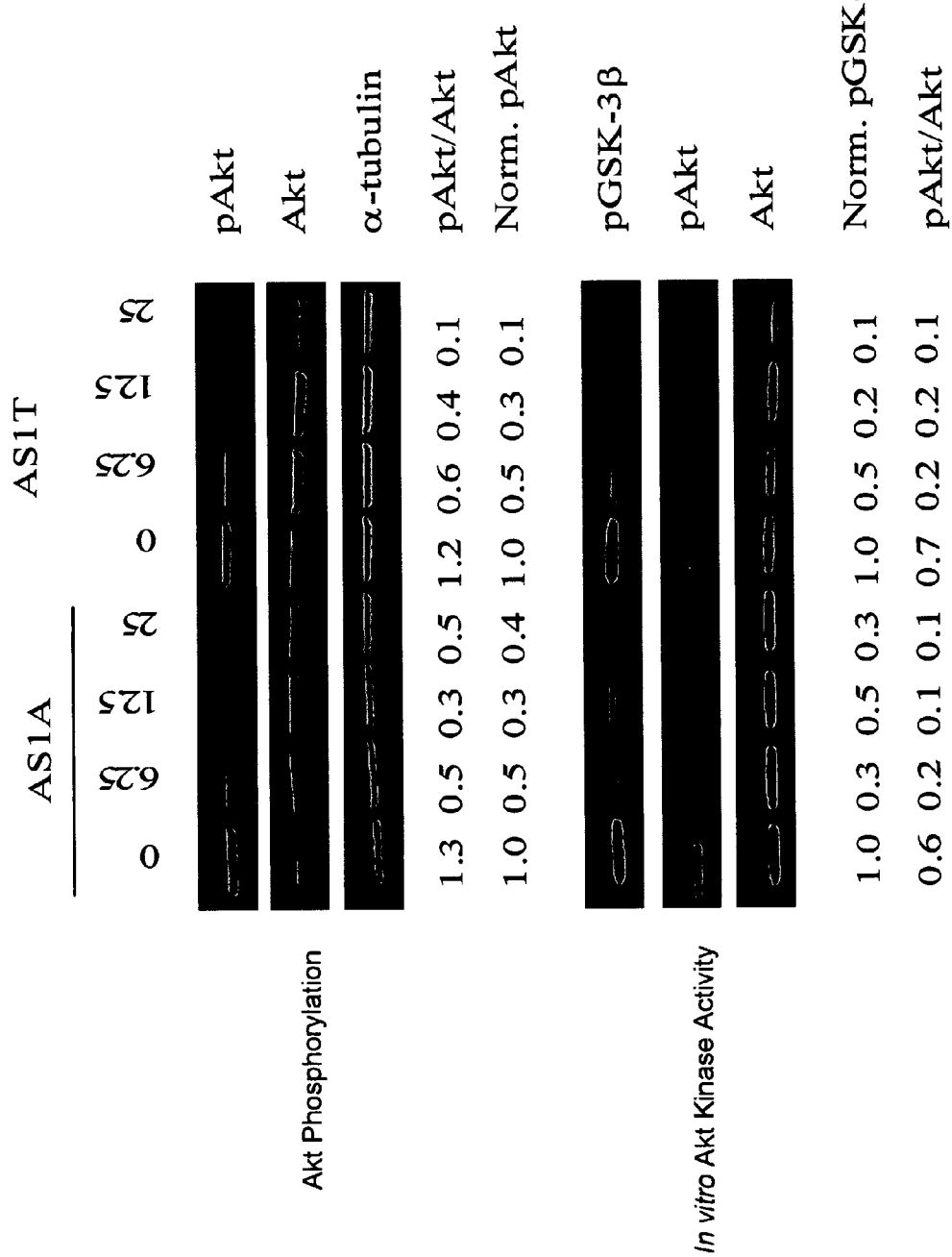

To validate AS1T as a genetically-encoded reporter for indirect imaging of endogenous Akt kinase activity, confirmation needed to be made that inhibition of endogenous Akt phosphorylation/kinase activities by LY and perifosine corresponded to increase in complemented FL activities in 293T/AS1T cells, but not in 293T/AS1A cells. 293T/AS1T and 293T/AS1A cells were treated with perifosine (6 hours), LY (24 hours) and their respective carrier controls. Complemented FL activities were determined by bioluminescence imaging of intact cells while Akt phosphorylation status/kinase activities in cell lysates were determined by phosphorylation-specific western blotting and in vitro kinase assay using purified glycogen synthase kinase 3β (GSK-3β) as the substrate, respectively. In 293T/AS1T cells treated with LY or perifosine, complemented FL activity increased (FIGS. 8a and 8c), while the amount of phosphorylated Akt (FIGS. 8b and 8d, top panels) and phosphorylated GSk-3, (FIGS. 8b and 8d, bottom panel) decreased, relative to carrier control treated cells. On the other hand, in 293T/AS1A cells treated with LY or perifosine, the amount of phosphorylated Akt and GSK-3β (FIGS. 8b and 8d) decreased while the increase in the complemented FL activity was substantially lower than that of 293T/AS1T cells. Furthermore, the amount of phosphorylated GSk3-β also correlated with the level of phosphorylated Akt for both 293T/AS1T and 293T/AS1A cells. All together, this data demonstrated that AS1T is sensitive, reversible and specific for indirect monitoring of endogenous Akt kinase activity in intact cells.

Efficacy of Akt Kinase Inhibitor Perifosine in Living Mice.

Figure 10A:
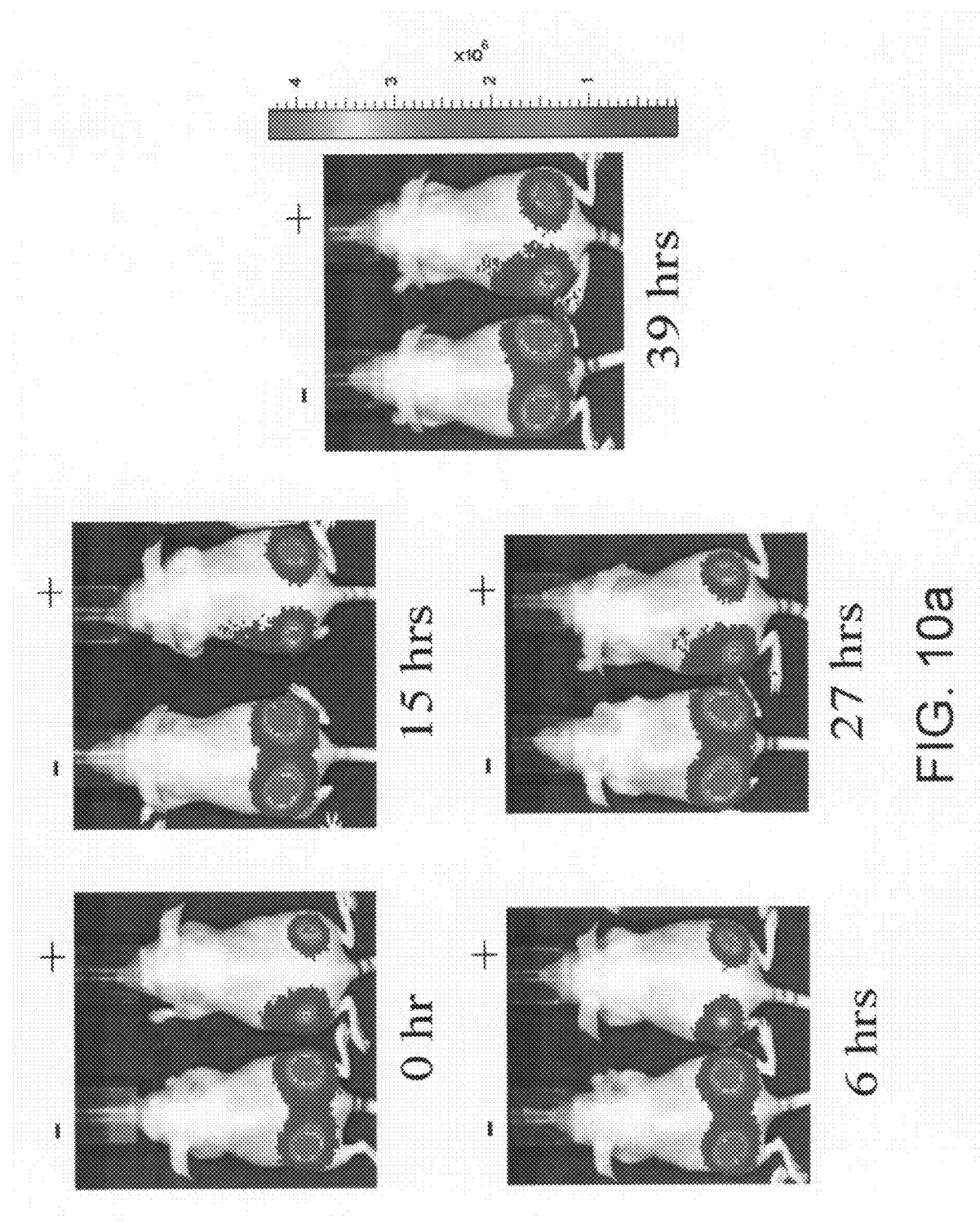
FIGS. 10a-10b illustrate the inhibition of Akt kinase activity by perifosine in living mice.
Figure 10B:
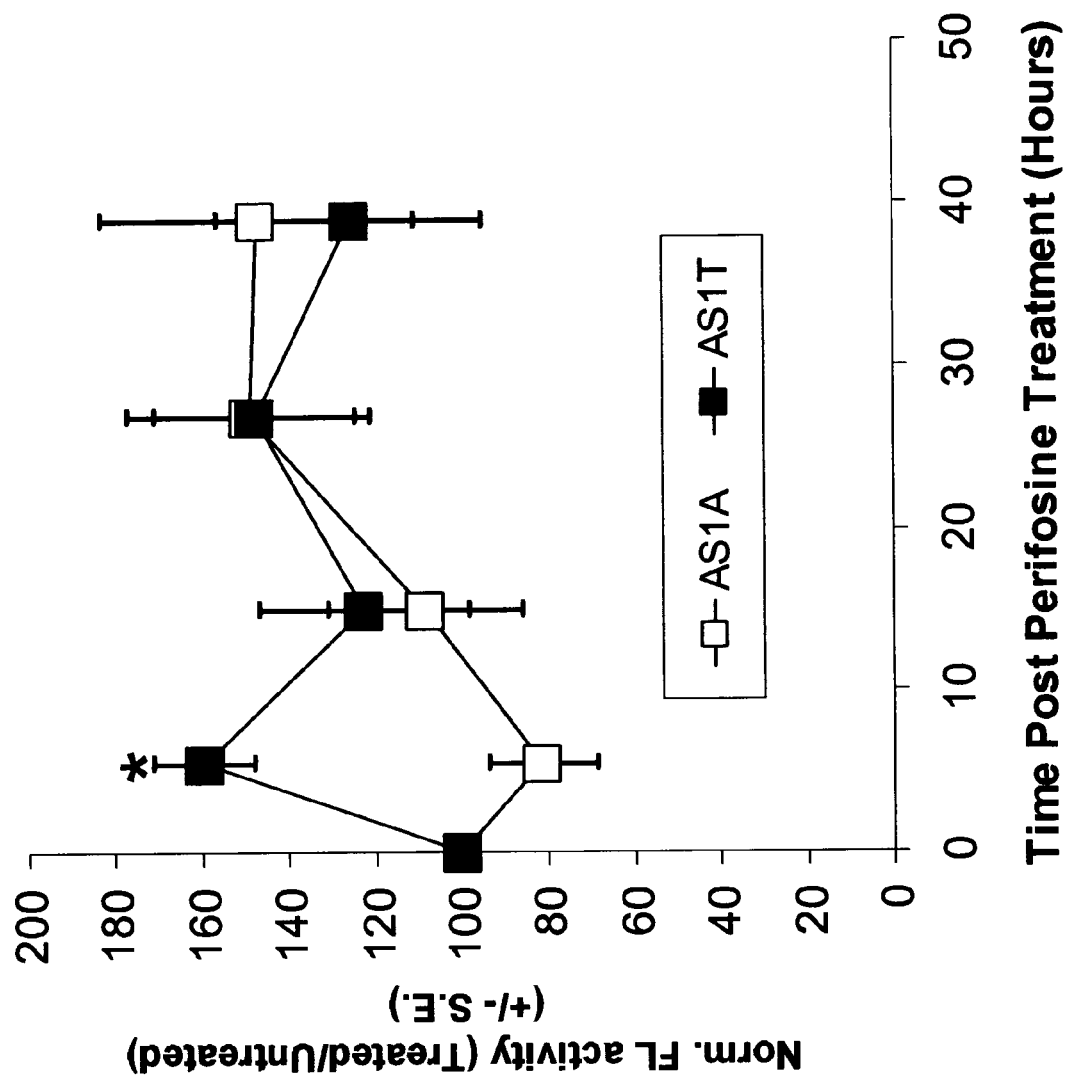

To determine if sufficient sensitivity for indirect imaging of Akt kinase activity has been achieved in living subjects, 293T/AS1T and 293T/AS1A cells were implanted at the lower left and right of nude mice for xenograft establishment. Since the bioluminescence signal from untreated 293T/AS1A cells was about 10-fold higher than that of 293T/AS1T cells in cell culture studies, 10% 293T/AS1A cells were mixed with 90% untransfected 293T cells (no FL activity) prior to implantation to normalize the signals to that of 293T/AS1T cells. Complemented FL activity in living mice was determined by bioluminescence imaging using a cooled coupled charged device (CCD) camera upon i.p. injection of D-luciferin. To monitor the efficacy of perifosine in inhibition of Akt kinase activity, nude mice bearing 293T/AS1T and 293T/AS1A xenografts were imaged at time 0 hr prior to treatment with 30 mg/kg of perifosine and reimaged at 6, 12 and 24 hours thereafter. Perifosine was chosen over LY for these animal experiments since perifosine is water soluble and currently being evaluated in clinical trials. FIG. 10a shows the bioluminescence images of complemented FL activity in 293T/AS1T (left) and 293T/AS1A (right) xenografts. 6 hours of perifosine treatment led of a 20% decrease in complemented FL activity in 293T/AS1A but a 60% increase in complemented FL activity in 293T/AS1T relative to carrier control treated mice (p<0.05), corresponding to the 2-fold difference between AS1T and AS1A (FIG. 10b). At later time points, there was no significant difference in complemented FL activity in 293T/AS1T and 293T/AS1A, relative to carrier control treated mice (p>0.05).

Discussion

Akt is an active target for chemotherapy since it is involved in cycle regulation, apoptosis and drug resistance. Different PI-3K and Akt inhibitors have been developed to inhibit Akt kinase activity. In the current study, the Akt kinase activity was directly monitored in response to the LY and perifosine using a novel split FL protein-fragment-assisted complementation system. The feasibility of using split FL complementation-based sensors (AS1A and AS1T) was first established in BT474 cells treated with the PI-3K inhibitor LY to inhibit Akt phosphorylation, and in 293T cells treated with PDGF to activate Akt phosphorylation. The genetically-encoded AS1T and the corresponding mutant sensor AS1A were then stably transfected into 293T cells to evaluate their kinetics, sensitivity, specificity and reversibility for indirect monitoring of Akt kinase activity in intact cells in response to the PI-3K inhibitor LY and perifosine which inhibits Akt activation (In; 1093-1103, which is incorporated herein by reference). The efficacy of perifosine in inhibition of Akt kinase activity in living mice was further validated by non-invasive optical bioluminescence imaging at different time points post treatment. The specificity of using the AS1T sensor to indirectly monitor Akt kinase activity using the non-phosphorylable AS1A mutant sensor has been confirmed. Furthermore, the decrease in Akt phosphorylation and kinase activity corresponded for the increased in complemented FL activity in 293T/AS1T but not for 293T/AS1A cells.

Even though LY and perifosine both inhibit Akt phosphorylation and its subsequent activation, complemented FL activity in LY treated 293T/AS1T cells increased from 12 to 24 hours. On the other hand, perifosine led to maximum increase in complemented FL activity at 6 hours post treatment, followed by gradual decrease at 12 and 24 hours. Furthermore, the correlations between inhibition of endogenous Akt phosphorylation/kinase activity were stronger for perifosine, compared to that of LY. The difference kinetics between LY and perifosine may be in part due to different solubility and stability under cell culture conditions. However, the phosphorylation status of AS1T under the cell culture conditions using phospho-Akt substrate motif antibodies or by immunoprecipitation of AS1T in conjunction with phosphothreonine antibodies were not monitored, perhaps due to masking of epitopes within the sensor. Even though both AS1T and FRET-based sensors are genetically encoded reporters that allow indirect imaging of Akt kinase activity, AS1T offers the advantages of greater dynamic range (4-fold maximum induction vs. 1.2-fold max induction for FRET-based sensors) in response to LY. Furthermore, the use of bioluminescence-based kinase sensors also allows the adaptation to high-throughput screening of libraries of lead compounds first in cell culture; followed for validation in living mice when coupled with optical bioluminescence imaging, where the pharmacokinetic properties of each Akt inhibitor influence efficacy.

To increase the dynamic range of AS1T for indirect monitoring of Akt kinase activity, the original FL fragments (NFL: 1-416/CFL: 398-550) were replaced with the optimal split FL sites (1-398/394-550) as AS2T. The corresponding FL fragments in AS1A were also replaced to create AS2A. 293T cells transiently transfected with AS2T or AS2A were treated with different concentrations of LY or carrier control for 24 hours prior to analysis of FL activity. A 2-fold increase in FL activity was observed for both 293T cells transiently transfected with AS2T or AS2A that were treated with LY for 24 hours, compared to that of 293T cells transiently transfected with AS1T or AS1A (unpublished data), thus the increase in sensitivity was accompanied by the loss of specificity. To determine if the specificity of AS2 can be restored by using more rigid linkers, the flexible $(G_4S)_3$ linkers were replaced with $(EAAAR)_3$ used for intramolecular folding sensors previously used to studying FRB/FKBP12 interactions. However, there was a loss of specificity in response to LY. Thus, our data suggest that there is a trade-off between sensitivity and specificity of using the split FL protein-fragment-assisted complementation system to monitor Akt kinase activity.

The AS1T sensor can be further optimized for their dynamic range and specificity by using different split reporter systems that are compatible with both cell culture and animal imaging. These changes include but are not limited to using different fragments and introducing mutations in split FL, split RL and other luciferases, as well as bioluminescence resonance energy transfer (BRET) system. Other changes include modifying the peptide linkers that connects the split reporters with that of the AKM and FHA2 domains, novel substrates for luciferases with better pharmacokinetic and imaging properties (such as wavelength and photon production) for imaging in living subjects. The current system could also be generalized to study different kinases of interest and to evaluate new inhibitors and modulators of signal transduction pathways. In summary, the development of the highly sensitive, specific and reversible Akt sensor will aid is investigation of kinases for pre-clinical drug development and target validation.

Materials and Methods

Chemicals, Enzymes and Reagents.

The plasmids pCMV-hRL encoding the full length synthetic Renilla Luciferase (RL) and the pCMV-FL encoding the full-length Firefly Luciferase (FL), LARII substrate for FL assay and 5× passive lysis buffer were purchased from Promega (Madison, Wis.). Restriction enzymes, modification enzymes and ligase were purchased from New England Biolabs (Beverly, Mass.). TripleMaster TaqDNA polymerase for PCR amplification was purchased from Brinkmann Eppendorf (Hamburg, Germany). Site-directed mutageneses were performed using the Stratagene kit (La Jolla, Calif.). Amplicillin and kanamycin for bacterial culture were purchased from Sigma (St. Louis, Mo.). Bacterial culture media were purchased from BD Diagnostic Systems (Sparks, Md.). SuperFect™ transfection reagent, plasmid extraction kits, and DNA gel extraction kits were purchased from Qiagen (Valencia, Calif.). Coelenterazine was purchased from Nanolight technology (Pinetop, Ariz.). All of the animal cell culture media, fetal bovine serum (FBS), the antibiotics streptomycin and penicillin, and plastic wares for cell cultures and Lipofectamine 2000 transfection reagents were purchased from Invitrogen (Carlsbad, Calif.).

Construction of Plasmid Vectors.

Plasmid vectors AS1-A and AS1-T were constructed by using split luciferase fragments, Akt kinase motif (AKM) peptide sequence (RKRDRLGTLGI, SEQ ID NO: 31) flanking the phosphorylation domain and the yeast phosphothreonine FHA2 binding domain. Nfluc fragment flanking amino acids 1-416 (SEQ ID NO: 33) and the Cfluc fragments flanking amino acids 394-550 (SEQ ID NO: 33) were used. The PCR amplified fragment of NFLUC (1-416) (SEQ ID NO: 33) with over hang primers coding for peptides for AKT (RKRDRLGTLGI, SEQ ID NO: 31) and AKA (RKRDRLGALGI, SEQ ID NO: 42) with Hind III restriction enzymes and the forward primer flanking the N-terminus of Firefly Luciferase with start codon and the Nhe I restriction enzyme site were cloned in to corresponding enzyme digested pcDNA 3.1 (+) vector backbone previously cloned with $(G_4S)_3$ linker in Hind III/EcoR I restriction enzyme site (pcDNA 3.1 (+)-NFLUC-AKM/AKT-$(G_4S)_3$. The PCR amplified fragment of FAH2 (cloned in EcoR I/BamH I) and CFLUC (cloned in BamH I/Xho I) in pcDNA 3.1 (−) were digested with Bam HI and Xba I restriction enzymes cloned to the corresponding enzyme digested (pcDNA 3.1 (+)-NFLUC-AKM/AKT-$(G_4S)_3$ site and constructed (pcDNA 3.1 (+)-NFLUC-AKT-$(G_4S)_3$-FAH2-CFLUC and (pcDNA 3.1 (+)-NFLUC-AKA-$(G_4S)_3$-FAH2-CFLUC.

Cell Culture.

All cell lines used in this study were purchased from American Type Culture Collection (Manassa, Va.). Human 293T embryonic kidney cancer cells were grown in minimal essentialmedium (MEM) supplemented with 10% fetal bovine serum (FSB) and 1% penicillin/streptomycin (P/S) solutions. Human BT474 invasive breast ductal carcinoma cells were grown in Dubelcco modified MEM (DMEM) supplemented with 10% FBS and 1% P/S solutions.

Cell Transfection, Firefly and Renilla Luciferase Assays.

Transfections were performed in 80% confluent 24 hr-old cultures of 293T and BT474 cells. For transient transfection, 250 ng/well of pcDNA molar equivalent of each AS1A and AS1T were used in 12-well tissue culture plates and 5 µl Lipofectamine 2000 was used per transfection following the manufacturer's instructions. 5 ng of pcDNA3.1(+) vector expressing full length RL was co-transfected per well to normalize for transfection efficiency. The cells were assayed after 24-hr incubation at 37° C. at 5% $CO_2$ to determine the effect of LY294004 (LY, Cell Signaling, Beverly, Mass.) and plate derived growth factor (PDGF, Calbiochem) on complemented FL activity, cells were treated with LY or PDGF at the time or transfection or 23 hours post-transfection, respectively. The luminometer assays for FL and RL activity were performed as previously described (Analytical Chemistry 75:1584-1589; Cancer Research 64:2113-2119; Proceedings of the National Academy of Sciences of the United States of America 99:15608-15613, each of which are incorporated herein by reference).

In brief, transfected cells were lysed in 200 µl of ice-cold 1× passive lysis buffer supplied by Promega and were shaken for 15 mins on ice. The cell lysates were centrifuged for 5 mins at $1.3 \times 10^4$ g at 4° C. to remove cell debris. To determine RL activity, 20 µl of supernatant was assayed by addition of 100 µl of LARII substrate (Promega), followed by photon counting in the luminometer (model T 20/20, Turner Designs, Sunnyvale, Calif.) for 10 seconds. RL activity was determined as described for FL activity, except 0.5 µg of coelenterazine dissolved in 100 µl of was used. Protein concentrations in cell lysates were determined by Bradford Assay (Bio-Rad). FL activities were normalized for protein content and for transfection efficiency using RL activity and expressed as relative light units per microgram protein per minute of counting (RLU/µg protein/min).

Selection of 293T Cells Stably Expressing AS1T and AS1A and Evaluation of the Efficacies of Different PI-3K and Akt Inhibitors in Cell Culture.

To generate 293T cells stably expressing AS1A or AS1T, $5 \times 10^6$ 293T cells were plated in each 10 cm tissue culture plate and allowed to attach for 24 hrs. Cells were co-transfected with 2 µg each of pcDNA3.1+ plasmids expressing AS1A or AS1T or 24 hours using 20 µl of Lipofectamine 2000, prior to trypsinizing and replating in 1.5 µg/ml of puromycin hydrochloride for 2 weeks at low density (~2000 cells/10 cm tissue culture plate) to allow formation of individual colonies. To screen for 293T cells expressing AS1A or AS1T, cell culture medium was aspirated and 0.5 µg of D-Luciferin (40 mg/ml in PBS) diluted in 1 ml of PBS was added and bioluminescence imaging of FL activity was performed using the IVIS 50 Imaging System (Xenogen Corp., Alameda, Calif.) with an acquisition time of 30 seconds. Positive colonies with the highest FL activity were trypsinized and transferred to individual wells in a 24-well plate and grown in medium containing 1.5 μg/ml puromycin, expanded and re-imaged once a week.

To determine the effect of PI-3K and Akt inhibitors on complementation of FL activity, $2.5 \times 10^5$ 293T cells stably transfected with AS1A (293T/AS1A) and AS1T (293T/AS1T) were plated in each 12 well plate and allowed to attach for 24 hours, prior to treatment with different concentrations of LY, perifosine or their respective carrier controls for 6, 12 and 24 hours. FL activities in intact cells were determined by bioluminescence imaging of intact cells as described above. Cells were lysed in 1% NP40 buffer (Cell Signaling, Beverly, Mass.) for 15 mins on ice followed by centrifugation at $1 \times 10^4$ g to remove cell debris. Protein concentrations were determined by Biorad protein Dc assay (Biorad). FL activities were normalized to protein content and then to that of carrier control treated cells and expressed as normalized FL activity±standard error of means (S.E.M.)

Akt Western Blotting and Kinase Assay.

To determine the expression of total and phosphorylated Akt in 293T/AS1A and 293T/AS1T, cell lysates from the triplicate wells from the above FL assay were combined and the protein concentrations were re-determined. 40 μg of total protein prepared in 1× Laemmli loading buffer with β-mercaptoethanol (Biorad) was heated at 95° C. for 3 mins and resolved using a 4-12% SDS-PAGE gradient gel (Invitrogen, Carlsbad, Calif.) and electroblotted onto a 0.2 μm nitrocellulose membrane (Schleicher & Schuell, Keene, N.H.). The membrane was blocked with 5% non-fat dry milk in Tris buffered saline containing 0.01% Tween 20 (TBS-T, pH=7.6) for 1 hour and probed overnight at 4° C. on a rotating platform with the appropriate antibodies as follow: horseradish peroxidase-conjugated goat anti-Firefly Luciferase polyclonal antibodies (1:5000 dilution, Biodesign International, Saco, Me.), rabbit polyclonal antibodies against human phosphorylated Akt($S^{473}$) or total Akt (1:1000 dilution for both, Cell Signaling). All western membranes were probed with a mouse monoclonal antibody against human α-tubulin (1:5000, clone B-5-1-2, Sigma) to control for protein loading. Secondary antibodies were peroxidase conjugated goat anti-mouse IgG or peroxidase conjugated goat anti-rabbit IgG (1:3000 dilution for both, Cell Signaling). Immunoblots were developed using the Pierce enhanced ECL Western blot substrate (Pierce, Rockford, Ill.) following manufacturer's instructions and developed using blue films (Midwest Scientific, St Louis, Mo.).

To measure Akt kinase activities, 200 μg of whole cell lysates were used in an in vitro Akt kinase assay using a Cell Signaling kit (Beverly, Mass.). Briefly, Akt was immunoprecipitated using the immobilized Akt antibody, followed by an in vitro kinase assay at 30° C. for 1 hour using 1 μg of the purified GSK-3β fusion protein as the substrate. The kinase reaction was terminated with 3× loading buffer and heated at 95° C. for 3 mins. One third of the kinase reaction (25 μl) was resolved by 4-16% SDS-PAGE gel and transferred to a nitrocellulose membrane for Western analysis. Phospho-Akt ($S^{473}$) and phospho-GSK-3β were detected using phosphospecific antibodies (1:1000), followed by stripping and reprobing with total Akt antibody (1:1000) as described above. Membranes were developed as described above. In all cases, band intensities were quantified by Image J (National Institute of Health, Bethesada, Md.).

Optical CCD Imaging in Living Mice.

All of the animal handling was performed in accordance with Stanford University Animal Research Committee guidelines, Mice were gas anesthetized using isofluorane (2% isofluorane in 100% oxygen) during all injection and imaging procedures. Mice were imaged using a cooled CCD camera (Xenogen IVIS29; Xenogen Corp., Alameda, Calif.). $3 \times 10^6$ 293T cells stably co-transfected with AS1T or $3 \times 10^5$ 293T cells stably transfected with AS1A mixed with $2.7 \times 10^6$ 293T cells were implanted subcutaneously in the bottom left and right flanks of each female nude mouse of 7 weeks old (nulnu, Charles River), respectively for 7 days for tumor establishment. To determine complemented FL activity in the implanted tumors in living mice, 4 mg of D-luciferin in 100 μl of PBS were injected I.P. prior to serial imaging with the IVIS system an acquisition time of 10 seconds. The animals were placed prone in a light-tight chamber, and a gray scale reference image was obtained under low-level illumination. Photons emitted from cells implanted in the mice were collected and integrated for 10 seconds. Images were obtained using Living Image Software (Xenogen Corp.) and Igor Image Analysis Software (Wavemetrics, Seattle, Wash.). To quantify the measured light, regions of interest were drawn over the area of the implanted cells, and the maximum photons/s/$cm^2$/steradian (sr) were obtained as validated previously. Mice were then given 30 mg/kg of Perifosine dissolved in 200 μl saline or 200 μl saline as carrier control by oral galvage and re-imaged at 6, 12 and 24 hours upon i.p. injection of 4 mg D-luciferin. Max photons at time 6, 12 and 24 hours were normalized to that of time 0 hr for each individual mouse, and expressed as normalized average max photons±S.E.M.

Data Analysis.

Each experiment was repeated at least three times and results were expressed as mean+/−standard deviation (S.D.) or standard error of means (S.E.M.). Statistical differences were determined by student t-test using p<0.05 as the cut-off point.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Sequences

SEQ ID No. 1, *Renilla* Luciferase protein maskvydpeq rkrmitgpqw warckqmnyl dsfinyydse khaenavifl hgnaassylw rhvvphiepv arciipdlig mgksgksgng syrlldhyky ltawfellnl pkkiifvghd wgaclafhys yehqdkikai vhaesvvdvi eswdewpdie edialiksee gekmvlennf fvetmlpski mrklepeefa aylepfkekg evrrptlswp reiplvkggk pdvvqivrny naylrasddl pkmfiesdpg ffsnaivega kkfpntefvk vkglhfsqed apdemgkyik sfvervlkne q SEQ ID No. 2, Double mutant (C124A/M185V) *Renilla* Luciferase protein maskvydpeq rkrmitgpqw warckqmnyl dsfinyydse khaenavifl hgnaassylw rhvvphiepv arciipdlig mgksgksgng syrlldhyky ltawfellnl pkkiifvghd wgaalafhys yehqdkikai vhaesvvdvi eswdewpdie edialiksee gekmvlennf fvetylpski mrklepeefa aylepfkekg evrrptlswp reiplvkggk pdvvqivrny naylrasddl pkmfiesdpg ffsnaivega kkfpntefvk vkglhfsqed apdemgkyik sfvervlkne q SEQ ID No. 3, Mutated (8) *Renilla* Luciferase protein maskvydpeq rkrmitgpqw warckqmnyl dsfinyydse khaenavifl hgnatssylw rhvvphiepv arciipdlig mgksgksgng syrlldhyky ltawfellnl pkkiifvghd wgaalafhya yehqdrikai vhmesvvdvi eswdewpdie edialiksee gekmvlennf fvetylpski mrklepeefa aylepfkekg evrrptlswp reiplvkggk pdvvqivrny naylrasddl pklfiesdpg ffsnaivega kkfpntefvk vkglhflqed apdemgkyik sfvervlkne q

```
SEQ. ID No. 4, Nucleotide sequence of full length Firefly Luciferase (amino acids 1-
550)
atggaagacgccaaaaacataaagaaaggcccggcgccattctatccgctggaagatggaaccgctggagagc aactgcataaggctatgaagagatacgccctggttcctggaacaattgcttttacagatgcacatatcgaggtggacat cacttacgctgagtacttcgaaatgtccgttcggttggcagaagctatgaaacgatatgggctgaatacaaatcacag aatcgtcgtatgcagtgaaaactctcttcaattctttatgccggtgttgggcgcgttatttatcggagttgcagttgcgcccg cgaacgacatttataatgaacgtgaattgctcaacagtatgggcatttcgcagcctaccgtggtgttcgtttccaaaaag gggttgcaaaaaattttgaacgtgcaaaaaaagctcccaatcatccaaaaaattattatcatggattctaaaacggatt accagggatttcagtcgatgtacacgttcgtcacatctcatctacctcccggttttaatgaatacgattttgtgccagagtc cttcgatagggacaagacaattgcactgatcatgaactcctctggatctactggtctgcctaaaggtgtcgctctgcctc atagaactgcctgcgtgagattctcgcatgccagagatcctattttggcaatcaaatcattccggatactgcgattttaa gtgttgttccattccatcacggttttggaatgtttactacactcggatatttgatatgtggatttcgagtcgtcttaatgtataga tttgaagaagagctgtttctgaggagccttcaggattacaagattcaaagtgcgctgctggtgccaaccctattctccttct tcgccaaaagcactctgattgacaaatacgatttatctaatttacacgaaattgcttctggtggcgctcccctctctaagg aagtcggggaagcggttgccaagaggttccatctgccaggtatcaggcaaggatatgggctcactgagactacatc agctattctgattacacccgaggggatgataaaccgggcgcggtcggtaaagttgttccatttttgaagcgaaggttg tggatctggataccgggaaaacgctgggcgttaatcaaagaggcgaactgtgtgtgagaggtcctatgattatgtccg gttatgtaaacaatccggaagcgaccaacgccttgattgacaaggatggatggctacattctggagacatagcttact gggacgaagacgaacacttcttcatcgttgaccgcctgaagtctctgattaagtacaaaggctatcaggtggctcccg ctgaattggaatccatcttgctccaacaccccaacatcttcgacgcaggtgtcgcaggtcttcccgacgatgacgccg gtgaacttcccgccgccgttgttgttttggagcacggaaagacgatgacggaaaaagagatcgtggattacgtcgcc agtcaagtaacaaccgcgaaaaagttgcgcggaggagttgtgtttgtggacgaagtaccgaaaggtcttaccggaa aactcgacgcaagaaaaatcagagagatcctcataaaggccaagaagggcggaaagatcgccgtgtaa SEQ. ID No. 5, Nucleotide sequence of NLUC-1-475 fragment
atggaagacgccaaaaacataaagaaaggcccggcgccattctatcctctagaggatggaaccgctggagagca actgcataaggctatgaagagatacgccctggttcctggaacaattgcttttacagatgcacatatcgaggtgaacatc acgtacgcggaatacttcgaaatgtccgttcggttggcagaagctatgaaacgatatgggctgaatacaaatcacag aatcgtcgtatgcagtgaaaactctcttcaattctttatgccggtgttgggcgcgttatttatcggagttgcagttgcgcccg cgaacgacatttataatgaacgtgaattgctcaacagtatgaacatttcgcagcctaccgtagtgtttgtttccaaaaag gggttgcaaaaaattttgaacgtgcaaaaaaaattaccaataatccagaaaattattatcatggattctaaaacggatt accagggatttcagtcgatgtacacgttcgtcacatctcatctacctcccggttttaatgaatacgattttgtaccagagtc ctttgatcgtgacaaaacaattgcactgataatgaattcctctggatctactgggttacctaagggtgtggcccttccgcat agagctgcctgcgtcagattctcgcatgccagagatcctattttggcaatcaaatcgctccggatactgcgattttaagt gttgttccattccatcacggttttggaatgtttactacactcggatatttgatatgtggatttcgagtcgtcttaatgtatagatt tgaagaagagctgtttttacgatcccttcaggattacaaaattcaaagtgcgttgctagtaccaaccctatttttcattcctgg
```

-continued ccaaaagcactctgattgacaaatacgatttatctaatttacacgaaattgcttctgggggcgcacctctttcgaaagaa gtcggggaagcggttgcaaaacgcttccatcttccagggatacgacaaggatatgggctcactgagactacatcagc tattctgattacacccaaggggatgataaaccgggcgcggtcggtaaagttgttccatttttttgaagcgaaggttgtgg atctggataccggaaaacgctgggcgttaatcagagaggcgaattatgtgtcagaggacctatgattatgtccggtt atgtaaacaatccggaagcgaccaacgccttgattgacaaggatggatggctacattctggagacatagcttactgg gacgaagacgaacacttcttcatagttgaccgcttgaagtctttaattaaatacaaaggatatcaggtggcccccgctg aattggaatcgatattgttacaacaccccaacatcttcgacgcgggcgtggcaggtcttcccgacgattaa SEQ ID No. 6, Amino Acid sequence corresponding to NLUC-1-475 fragment
MEDAKNIKKGPAPFYPLEDGTAGEQLHKAMKRYALVPGTIAFTDAHIEVDITYAEYF

EMSVRLAEAMKRYGLNTNHRIVVCSENSLQFFMPVLGALFIGVAVAPANDIYNEREL

LNSMGISQPTVVFVSKKGLQKILNVQKKLPIIQKIIIMDSKTDYQGFQSMYTFVTSHLP

PGFNEYDFVPESFDRDKTIALIMNSSGSTGLPKGVALPHRTACVRFSHARDPIFGN

QIIPDTAILSVVPFHHGFGMFTTLGYLICGFRVVLMYRFEEELFLRSLQDYKIQSALLV

PTLFSFFAKSTLIDKYDLSNLHEIASGGAPLSKEVGEAVAKRFHLPGIRQGYGLTETT

SAILITPEGDDKPGAVGKVVPFFEAKVVDLDTGKTLGVNQRGELCVRGPMIMSGYV

NNPEATNALIDKDGWLHSGDIAYWDEDEHFFIVDRLKSLIKYKGYQVAPAELESILLQ

HPNIFDAGVAGLPDD

SEQ ID No. 7, Nucleotide sequence of CLUC-265-550 fragment
atgtatagatttgaagaagagctgtttctgaggagccttcaggattacaagattcaaagtgcgctgctggtgccaaccct attctccttcttcgccaaaagcactctgattgacaaatacgatttatctaatttacacgaaattgcttctggtggcgctcccc tctctaaggaagtcggggaagcggttgccaagaggttccatctgccaggtatcaggcaaggatatgggctcactgag actacatcagctattctgattacacccgaggggatgataaaccgggcgcggtcggtaaagttgttccattttttgaagc gaaggttgtggatctggataccgggaaaacgctgggcgttaatcaaagaggcgaactgtgtgtgagaggtcctatga ttatgtccggttatgtaaacaatccggaagcgaccaacgccttgattgacaaggatggatggctacattctggagacat agcttactgggacgaagacgaacacttcttcatcgttgaccgcctgaagtctctgattaagtacaaaggctatcaggtg gctcccgctgaattggaatccatcttgctccaacaccccaacatcttcgacgcaggtgtcgcaggtcttcccgacgatg acgccggtgaacttcccgccgccgttgttgftttggagcacggaaagacgatgacggaaaaagagatcgtggattac gtcgccagtcaagtaacaaccgcgaaaaagttgcgcggaggagttgtgtttgtggacgaagtaccgaaaggtcttac cggaaaactcgacgcaagaaaaatcagagagatcctcataaaggccaagaagggcggaaagatcgccgtgtaa SEQ ID No. 8, Amino Acid sequence corresponding to CLUC-265-550 fragment
MYRFEEELFLRSLQDYKIQSALLVPTLFSFFAKSTLIDKYDLSNLHEIASGGAPLSKE

VGEAVAKRFHLPGIRQGYGLTETTSAILITPEGDDKPGAVGKVVPFFEAKVVDLDTG

KTLGVNQRGELCVRGPMIMSGYVNNPEATNALIDKDGWLHSGDIAYWDEDEHFFIV

DRLKSLIKYKGYQVAPAELESILLQHPNIFDAGVAGLPDDDAGELPAAVVVLEHGKT

MTEKEIVDYVASQVTTAKKLRGGVVFVDEVPKGLTGKLDARKIREILIKAKKGGKIAV

SEQ ID No. 9, NLUC-398 (1-398)
atggaagacgccaaaaacataaagaaaggcccggcgccattctatccgctggaagatggaaccgctggagagc aactgcataaggctatgaagagatacgccctggttcctggaacaattgcttttacagatgcacatatcgaggtggacat cacttacgctgagtacttcgaaatgtccgttcggttggcagaagctatgaaacgatatgggctgaatacaaatcacag aatcgtcgtatgcagtgaaaactctcttcaattctttatgccggtgttgggcgcgttatttatcggagttgcagttgcgcccg cgaacgacatttataatgaacgtgaattgctcaacagtatgggcatttcgcagcctaccgtggtgttcgtttccaaaaag gggttgcaaaaaattttgaacgtgcaaaaaaagctcccaatcatccaaaaaattattatcatggattctaaaacggatt -continued

```
accagggatttcagtcgatgtacacgttcgtcacatctcatctacctcccggttttaatgaatacgattttgtgccagagtc cttcgatagggacaagacaattgcactgatcatgaactcctctggatctactggtctgcctaaaggtgtcgctctgcctc atagaactgcctgcgtg agattctcgcatgccagagatcctattttttggcaatcaaatcattccggatactgcgattttaa gtgttgttccattccatcacggttttggaatgtttactacactcggatatttgatatgtggatttcgagtcgtcttaatgtataga tttgaagaagagctgtttctgaggagccttcaggattacaagattcaaagtgcgctgctggtgccaaccctattctccttct tcgccaaaagcactctgattgacaaatacgatttatctaatttacacgaaattgcttctggtggcgctcccctctctaagg aagtcggggaagcggttgccaagaggttccatctgccaggtatcaggcaaggatatgggctcactgagactacatc agctattctgattacacccgaggggatgataaaccgggcgcggtcggtaaagttgttccatttttttgaagcgaaggttg tggatctggataccgggaaaacgctgggcgttaatcaaagaggcgaactgtgtgtgagaggtcctatgattatg
```

SEQ ID No. 10, amino acid sequence corresponding to NLUC-1-398
MEDAKNIKKGPAPFYPLEDGTAGEQLHKAMKRYALVPGTIAFTDAHIEVDITYAEYF

EMSVRLAEAMKRYGLNTNHRIVVCSENSLQFFMPVLGALFIGVAVAPANDIYNEREL

LNSMGISQPTVVFVSKKGLQKILNVQKKLPIIQKIIIMDSKTDYQGFQSMYTFVTSHLP

PGFNEYDFVPESFDRDKTIALIMNSSGSTGLPKGVALPHRTACVRFSHARDPIFGN

QIIPDTAILSVVPFHHGFGMFTTLGYLICGFRVVLMYRFEEELFLRSLQDYKIQSALLV

PTLFSFFAKSTLIDKYDLSNLHEIASGGAPLSKEVGEAVAKRFHLPGIRQGYGLTETT

SAILITPEGDDKPGAVGKVVPFFEAKVVDLDTGKTLGVNQRGELCVRGPMIM

SEQ ID No. 11, CLUC-398 (398-550)
```
tccggttatgtaaacaatccggaagcgaccaacgccttgattgacaaggatggatggctacattctggagacatagct tactgggacgaagacgaacacttcttcatcgttgaccgcctgaagtctctgattaagtacaaaggctatcaggtggctc ccgctgaattggaatccatcttgctccaacaccccaacatcttcgacgcaggtgtcgcaggtcttcccgacgatgacg ccggtgaacttcccgccgccgttgttgttttggagcacggaaagacgatgacggaaaaagagatcgtggattacgtc gccagtcaagtaacaaccgcgaaaaagttgcgcggaggagttgtgtttgtggacgaagtaccgaaaggtcttaccg gaaaactcgacgcaagaaaaatcagagagatcctcataaaggccaagaagggcggaaagatcgccgtgtaa
```

SEQ ID No. 12, amino acid sequence corresponding to CLUC-398-550
MSGYVNNPEATNALIDKDGWLHSGDIAYWDEDEHFFIVDRLKSLIKYKGYQVAPAE

LESILLQHPNIFDAGVAGLPDDDAGELPAAVVVLEHGKTMTEKEIVDYVASQVTTAK

KLRGGWFVDEVPKGLTGKLDARKIREILIKAKKGGKIAV

SEQ ID No. 13, CLUC-394 (394-550)
```
cctatgattatgtccggttatgtaaacaatccggaagcgaccaacgccttgattgacaaggatggatggctacattctg gagacatagcttactgggacgaagacgaacacttcttcatcgttgaccgcctgaagtctctgattaagtacaaaggct atcaggtggctcccgctgaattggaatccatcttgctccaacaccccaacatcttcgacgcaggtgtcgcaggtcttcc cgacgatgacgccggtgaacttcccgccgccgttgttgttttggagcacggaaagacgatgacggaaaaagagatc gtggattacgtcgccagtcaagtaacaaccgcgaaaaagttgcgcggaggagttgtgtttgtggacgaagtaccgaa aggtcttaccggaaaactcgacgcaagaaaaatcagagagatcctcataaaggccaagaagggcggaaagatc gccgtgtaa
```

SEQ ID No. 14, amino acid sequence corresponding to CLUC-394-550
GPMIMSGYVNNPEATNALIDKDGWLHSGDIAYWDEDEHFFIVDRLKSLIKYKGYQV

APAELESILLQHPNIFDAGVAGLPDDDAGELPAAVVVLEHGKTMTEKEIVDYVASQV

TTAKKLRGGVVFVDEVPKGLTGKLDARKIREILIKAKKGGKIAV

-continued

SEQ ID No. 15, nucleotide sequence of *Coleoptera Luciferase*
ATG GTAAAGCGTGAGAAAAATGT CATCTATGGC CCTGAGCCTC TCCATCCTTT

GGAGGATTTGACTGCCGGCG AAATGCTGTT TCGTGCTCTC CGCAAGCACT

CTCATTTGCCTCAAGCCTTG GTCGATGTGG TCGGCGATGA ATCTTTGAGC

TACAAGGAGTTTTTTGAGGC AACCGTCTTG CTGGCTCAGT CCCTCCACAA

TTGTGGCTACAAGATGAACG ACGTCGTTAG TATCTGTGCT GAAAACAATA

CCCGTTTCTTCATTCCAGTC ATCGCCGCAT GGTATATCGG TATGATCGTG

GCTCCAGTCAACGAGAGCTA CATTCCCGAC GAACTGTGTA AAGTCATGGG

TATCTCTAAGCCACAGATTG TCTTCACCAC TAAGAATATT CTGAACAAAG

TCCTGGAAGTCCAAAGCCGC ACCAACTTTA TTAAGCGTAT CATCATCTTG

GACACTGTGGAGAATATTCA CGGTTGCGAA TCTTTGCCTA ATTTCATCTC

TCGCTATTCAGACGGCAACA TCGCAAACTT TAAACCACTC CACTTCGACC

CTGTGGAACAAGTTGCAGCC ATTCTGTGTA GCAGCGGTAC TACTGGACTC

CCAAAGGGAGTCATGCAGAC CCATCAAAAC ATTTGCGTGC GTCTGATCCA

TGCTCTCGATCCACGCTACG GCACTCAGCT GATTCCTGGT GTCACCGTCT

TGGTCTACTTGCCTTTCTTC CATGCTTTCG GCTTTCATAT TACTTTGGGT

TACTTTATGGTCGGTCTCCG CGTGATTATG TTCCGCCGTT TTGATCAGGA

GGCTTTCTTGAAAGCCATCC AAGATTATGA AGTCCGCAGT GTCATCAACG

TGCCTAGCGTGATCCTGTTT TTGTCTAAGA GCCCACTCGT GGACAAGTAC

GACTTGTCTTCACTGCGTGA ATTGTGTTGC GGTGCCGCTC CACTGGCTAA

GGAGGTCGCTGAAGTGGCCG CCAAACGCTT GAATCTTCCA GGGATTCGTT

GTGGCTTCGGCCTCACCGAA TCTACCAGTG CGATTATCCA GACTCTCGGG

GATGAGTTTAAGAGCGGCTC TTTGGGCCGT GTCACTCCAC TCATGGCTGC

TAAGATCGCTGATCGCGAAA CTGGTAAGGC TTTGGGCCCG AACCAAGTGG

GCGAGCTGTGTATCAAAGGC CCTATGGTGA GCAAGGGTTA TGTCAATAAC

GTTGAAGCTACCAAGGAGGC CATCGACGAC GACGGCTGGT TGCATTCTGG

TGATTTTGGATATTACGACG AAGATGAGCA TTTTTACGTC GTGGATCGTT

ACAAGGAGCTGATCAAATAC AAGGGTAGCC AGGTTGCTCC AGCTGAGTTG

GAGGAGATTCTGTTGAAAAA TCCATGCATT CGCGATGTCG CTGTGGTCGG

CATTCCTGATCTGGAGGCCG GCGAACTGCC TTCTGCTTTC GTTGTCAAGC

AGCCTGGTACAGAAATTACC GCCAAAGAAG TGTATGATTA CCTGGCTGAA

CGTGTGAGCCATACTAAGTA CTTGCGTGGC GGCGTGCGTT TTGTTGACTC

CATCCCTCGTAACGTAACAG GCAAAATTAC CCGCAAGGAG CTGTTGAAAC

AATTGTTGGTGAAGGCCGGC GGTTAG

SEQ ID No. 16, amino acid sequence of *Coleoptera Luciferase*
MVKREKNVIYGPEPLHPLEDLTAGEMLFRALRKHSHLPQALVDVVGDESLSYKEFF

EATVLLAQSLHNCGYKMNDVVSICAENNTRFFIPVIAAWYIGMIVAPVNESYIPDELC

KVMGISKPQIVFTTKNILNKVLEVQSRTNFIKRIIILDTVENIHGCESLPNFISRYSDGNI

ANFKPLHFDPVEQVAAILCSSGTTGLPKGVMQTHQNICVRLIHALDPRYGTQLIPGV

TVLVYLPFFHAFGFHITLGYFMVGLRVIMFRRFDQEAFLKAIQDYEVRSVINVPSVILF

LSKSPLVDKYDLSSLRELCCGAAPLAKEVAEVAAKRLNLPGIRCGFGLTESTSAIIQT

-continued

LGDEFKSGSLGRVTPLMAAKIADRETGKALGPNQVGELCIKGPMVSKGYVNNVEAT

KEAIDDDGWLHSGDFGYYDEDEHFYVVDRYKELIKYKGSQVAPAELEEILLKNPCIR

DVAVVGIPDLEAGELPSAFVVKQPGTEITAKEVYDYLAERVSHTKYLRGGVRFVDSI

PRNVTGKITRKELLKQLLVKAGG

SEQ ID No. 17, nucleotide sequence of *Gaussia Luciferase*
atgggagtgaa agttcttttt gcccttattt gtattgctgt ggccgaggcc aaaccaactg aaaacaatga agatttcaac attgtagctg tagctagcaa ctttgctaca acggatctcg atgctgaccg tggtaaattg cccggaaaaa aattaccact tgaggtactc aaagaaatgg aagccaatgc taggaaagct ggctgcacta ggggatgtct gatatgcctg tcacacatca agtgtacacc caaaatgaag aagtttatcc caggaagatg ccacacctat gaaggagaca agaaagtgc acagggagga ataggagagg ctattgttga cattcctgaa attcctgggt ttaaggattt ggaacccatg aacaattca ttgcacaagt tgacctatgt gtagactgca caactggatg cctcaaaggt cttgccaatg tgcaatgttc tgatttactc aagaaatggc tgccacaaag atgtgcaact tttgctagca aaattcaagg ccaagtggac aaaataaagg gtgccggtgg tgattaa SEQ ID No. 18, amino acid sequence of *Gaussia Luciferase*
MGVKVLFALICIAVAEAKPTENNEDFNIVAVASNFATTDLDADRGKLPGKKLPLEVLK

EMEANARKAGCTRGCLICLSHIKCTPKMKKFIPGRCHTYEGDKESAQGGIGEAIVDI

PEIPGFKDLEPMEQFIAQVDLCVDCTTGCLKGLANVQCSDLLKKWLPQRCATFASKI

QGQVDKIKGAGGD

SEQ ID No. 19, nucleotide sequence of *Aqueorin Photoprotein Luciferase*
ATG CTT ACA TCA GAC TTC GAC AAC CCA AGA TGG ATT GGA CGA CAC AAG

CAT ATG TTC AAT TTC CTT GAT GTC AAC CAC AAT GGA AAA ATC TCT CTT

GAC GAG ATG GTC TAC AAG GCA TCT GAT ATT GTC ATC AAT AAC CTT GGA

GCA ACA CCT GAG CAA GCC AAA CGA CAC AAA GAT GCT GTA GAA GCC

TTC TTC GGA GGA GCT GGA ATG AAA TAT GGT GTG GAA ACT GAT TGG CCT

GCA TAT ATT GAA GGA TGG AAA AAA TTG GCT ACT GAT GAA TTG GAG AAA

TAC GCC AAA AAC GAA CCA ACG CTC ATC CGT ATA TGG GGT GAT GCT TTG

TTT GAT ATC GTT GAC AAA GAT CAA AAT GGA GCC ATT ACA CTG GAT GAA

TGG AAA GCA TAC ACC AAA GCT GCT GGT ATC ATC CAA TCA TCA GAA GAT

TGC GAG GAA ACA TTC AGA GTG TGC GAT ATT GAT GAA AGT GGA CAA CTC

GAT GTT GAT GAG ATG ACA AGA CAA CAT TTA GGA TTT TGG TAC ACC ATG

GAT CCT GCT TGC GAA AAG CTC TAC GGT GGA GCT GTC CCC TAA

SEQ ID No. 20, amino acid sequence of *Aqueorin Photoprotein Luciferase*
MLTSDFDNPRWIGRHKHMFNFLDVNHNGKISLDEMVYKASDIVINNLGATPEQAKR

HKDAVEAFFGGAGMKYGVETDWPAYIEGWKKLATDELEKYAKNEPTLIRIWGDALF

DIVDKDQNGAITLDEWKAYTKAAGIIQSSEDCEETFRVCDIDESGQLDVDEMTRQHL

GFWYTMDPACEKLYGGAVP

SEQ ID No. 21, nucleotide sequence of *Bacterial Luciferase*
atgaataa atggaattac ggagtcttct tcgttaactt ttataataaa ggccaacaag agccatcaaa acgatgaat aatgcattag aaacattacg tattattgat aagatacat ctatttatga tgtgattaat attgatgacc actatcttgt aaagaaagac agtgaagata aaaagctagc gtcttttat acactaggag aaaaactata tgtgcttgct accagtgaaa acacagttga tattgcagcg aaatatgcat taccgttagt tttcaaatgg gatgatataa atgaggaacg acttaaattg ttgagttttt ataatgcatc cgcaagtaaa tataacaaga atatagattt ggttcgacac cagcttatgt tacatgtcaa tgttaatgag gcagaaactg -continued

```
tagcaaaaga agaactcaaa ttatatattg aaaactatgt agcatgtaca cagcctagta attttaatgg ctcgattgat agtattattc agagtaacgt gacagggagt tataaagact gtttgtcata tgtagcgaat cttgctggta aatttgataa tactgtggac ttcttacttt gttttgagtc aatgcaagat caaaataaga aaaaatcagt aatgatagat cttaataatc aagttattaa gttccgccaa gataataatc taa
```

SEQ ID No. 22, amino acid sequence of *Bacterial Luciferase*
MNKWNYGVFFVNFYNKGQQEPSKTMNNALETLRIIDEDTSIYDVINIDDHYLVKKDS

EDKKLASFITLGEKLYVLATSENTVDIAAKYALPLVFKWDDINEERLKLLSFYNASAS

KYNKNIDLVRHQLMLHVNVNEAETVAKEELKLYIENYVACTQPSNFNGSIDSIIQSNV

TGSYKDCLSYVANLAGKFDNTVDFLLCFESMQDQNKKKSVMIDLNNQVIKFRQDNN

LX

SEQ ID No. 23, nucleotide sequence of NRLUC (N-fragment of *Renilla Luciferase*)
ATG GCT TCC AAG GTG TAC GAC CCC GAG CAA CGC AAA CGC ATG ATC

ACT GGG CCT CAG TGG TGG GCT CGC TGC AAG CAA ATG AAC GTG CTG

GAC TCC TTC ATC AAC TAC TAT GAT TCC GAG AAG CAC GCC GAG AAC GCC

GTG ATT TTT CTG CAT GGT AAC GCT GCC TCC AGC TAC CTG TGG AGG CAC

GTC GTG CCT CAC ATC GAG CCC GTG GCT AGA TGC ATC ATC CCT GAT

CTG ATC GGA ATG GGT AAG TCC GGC AAG AGC GGG AAT GGC TCA TAT

CGC CTC CTG GAT CAC TAC AAG TAC CTC ACC GCT TGG TTC GAG CTG

CTG AAC CTT CCA AAG AAA ATC ATC TTT GTG GGC CAC GAC TGG GGG

GCT TGT CTG GCC TTT CAC TAC TCC TAC GAG CAC CAA GAC AAG ATC AAG

GCC ATC GTC CAT GCT GAG AGT GTC GTG GAC GTG ATC GAG TCC TGG

GAC GAG TGG CCT GAC ATC GAG GAG GAT ATC GCC CTG ATC AAG AGC

GAA GAG GGC GAG AAA ATG GTG CTT GAG AAT AAC TTC TTC GTC GAG

ACC ATG CTC CCA AGC AAG ATC ATG CGG AAA CTG GAG CCT GAG GAG

TTC GCT GCC TAC CTG GAG CCA TTC AAG GAG AAG GGC GAG GTT AGA

CGG CCT ACC CTC TCC TGG CCT CGC GAG ATC CCT CTC GTT AAG GGA

GGC

SEQ ID No. 24, amino acid sequence of NRLUC (N-fragment of *Renilla Luciferase*)
ASMASKVYDPEQRKRMITGPQWWARCKQMNVLDSFINYYDSEKHAENAVIFLHGN

AASSYLWRHVVPHIEPVARCIIPDLIGMGKSGKSGNGSYRLLDHYKYLTAWFELLNL

PKKIIFVGHDWGACLAFHYSYEHQDKIKAIVHAESVVDVIESWDEWPDIEEDIALIKS

EEGEKMVLENNFFVETMLPSKIMRKLEPEEFAAYLEPFKEKGEVRRPTLSWPREIPL

VK

SEQ ID No. 25, nucleotide sequence of CRLUC (C-fragment of *Renilla Luciferase*)
AAGCCCGACGTCGTCCAGATTGTCCGCAACTACAACGCCTACCTTCGGGCCAG

CGACGATGTGCCTAAGATGTTCATCGAGTCCGACCCTGGGTTGTTTTCCAACGC

TATTGTCGAGGGAGCTAAGAAGTTCCCTAACACCGAGTTCGTGAAGGTGAAGG

GCCTCCACTTCAGCCAGGAGGACGCTCCAGATGAAATGGGTAAGTACATCAAG

AGCTTCGTGGAGCGCGTGCTGAAGAACGAGCAGTAA

SEQ ID No. 26, amino acid sequence of CRLUC (C-fragment of *Renilla Luciferase*)
KPDVVQIVRNYNAYLRASDDLPKMFIESDPGFFSNAIVEGAKKFPN

TEFVKVKGLHFSQEDAPDEMGKYIKSFVERVLKNEQ

-continued

SEQ ID No. 27, SH2-substrate recognition domain
DAEWYWGDISREEVNEKLRDTADGTFLVRDASTKMHGDYTLTLRKGGNNKLIKIFH

RDGKYGFSDPLTFSSVVELINHYRNESLAQYNPKLDVKLLYPVSKYQQ

SEQ ID No. 28, IRS-1-Phosphorylation domain
Thr-Glu-Glu-Ala-Tyr-Met-Lys-Met-Asp-Leu-Gly-Pro-Gly SEQ ID No. 29, IRS-2-Phosphorylation domain
Lys-Lys-His-Thr-Asp-Asp-Gly-Tyr-Met-Pro-Met-Ser-Pro-Gly-Val-Ala SEQ ID No. 30, FHA2-Substrate recognition domain
TAATGGTAGGTTTTTAACTTTAAAACCATTGCCTGACAGCATTATTCAAGAAAGC

CTGGAGATTCAGCAAGGTGTGAATCCATTTTTCATTGGTAGATCCGAGGATTGC

AATTGTAAAATTGAAGACAATAGGTTGTCTCGAGTTCATTGCTTCATTTTCAAAAA

GAGGCATGCTGTAGGCAAAAGCATGTATGAATCTCCGGCACAAGGTTTAGATGA

TATTTGGTATTGCCACACCGGAACTAACGTGAGCTATTTAAATAATAACCGCATG

ATACAGGGTACGAAATTCCTTTTACAAGACGGAGATGAAATCAAGATCATTTGG

GATAAAAACAATAAATTTGTCATTGGCTTTAAAGTGGAAATTAACGATACTACAG

GTCTGTTTAACGAGGGATTAGGTATGTTACAAGAACAAAGAGTAGTACTTAAGC

AAACAGCCGAAGAAAAAGATTTGGTGAAAAAGTTA

SEQ ID No. 31, PKB-Phosphorylation domain
RKRDRLGTLGI

SEQ ID No. 32, PKC- Phosphorylation domain
RFRRFQTLKIKAKA

SEQ ID No. 33, full length Firefly Luciferase amino acid sequence
MEDAKNIKKGPAPFYPLEDGTAGEQLHKAMKRYALVPGTIAFTDAHIEVDITYAEYF

EMSVRLAEAMKRYGLNTNHRIVVCSENSLQFFMPVLGALFIGVAVAPANDIYNEREL

LNSMGISQPTVVFVSKKGLQKILNVQKKLPIIQKIIIMDSKTDYQGFQSMYTFVTSHLP

PGFNEYDFVPESFDRDKTIALIMNSSGSTGLPKGVALPHRTACVRFSHARDPIFGN

QIIPDTAILSVVPFHHGFGMFTTLGYLICGFRVVLMYRFEEELFLRSLQDYKIQSALLV

PTLFSFFAKSTLIDKYDLSNLHEIASGGAPLSKEVGEAVAKRFHLPGIRQGYGLTETT

SAILITPEGDDKPGAVGKVVPFFEAKVVDLDTGKTLGVNQRGELCVRGPMIMSGYV

NNPEATNALIDKDGWLHSGDIAYWDEDEHFFIVDRLKSLIKYKGYQVAPAELESILLQ

HPNIFDAGVAGLPDDDAGELPAAVVVLEHGKTMTEKEIVDYVASQVTTAKKLRGGV

VFVDEVPKGLTGKLDARKIREILIKAKKGGKIAV

SEQ ID No. 34,
GGGGSGGGGS

SEQ ID No. 35,
ACGSLSCGSF

SEQ ID No. 36,
EAAAREAAAR

SEQ ID No. 37,
EAAAREAAAREAAAREAAAR

SEQ ID No. 38,
ACGSLSCGSFACGSLSCGSF

SEQ ID No. 39,
ATSATATSAT

SEQ ID No. 40,
Thr-Glu-Glu-Ala-Tyr-Met-Lys-Met-Asp-Leu-Gly-Pro-Gly

-continued

SEQ ID No. 41,
Lys-Lys-His-Thr-Asp-Asp-Gly-Tyr-Met-Pro-Met-Ser-Pro-Gly-Val-Ala

SEQ ID No. 42,
RKRDRLGTLGI

SEQ ID No. 43,
RFRRFQTLKIKAKA

SEQ ID No. 44, non-phosphorylable AKM
RKRDRLGALGI

SEQ ID No. 45,
EAAAREAAAREAAAREAAAREAAAR

SEQ ID No. 46, Firefly Luciferase amino acid 245-550
HGFGMFTTLGYLICGFRVVLMYRFEEELFLRSLQDYKIQSALLVPTLFSFFAKSTL

IDKYDLSNLHEIASGGAPLSKEVGEAVAKRFHLPGIRQGYGLTETTSAILITPEGDDK

PGAVGKVVPFFEAKVVDLDTGKTLGVNQRGELCVRGPMIMSGYVNNPEATNALIDK

DGWLHSGDIAYWDEDEHFFIVDRLKSLIKYKGYQVAPAELESILLQHPNIFDAGVAG

LPDDDAGELPAAVVVLEHGKTMTEKEIVDYVASQVTTAKKLRGGVVFVDEVPKGLT

GKLDARKIREILIKAKKGGKIAV

SEQ ID No. 47, Firefly Luciferase amino acid 300-550
LIDKYDLSNLHEIASGGAPLSKEVGEAVAKRFHLPGIRQGYGLTETTSAILITPEGDD

KPGAVGKVVPFFEAKVVDLDTGKTLGVNQRGELCVRGPMIMSGYVNNPEATNALID

KDGWLHSGDIAYWDEDEHFFIVDRLKSLIKYKGYQVAPAELESILLQHPNIFDAGVA

GLPDDDAGELPAAVVVLEHGKTMTEKEIVDYVASQVTTAKKLRGGVVFVDEVPKGL

TGKLDARKIREILIKAKKGGKIAV

---

We claim the following:

1. A phosphorylation sensing system, comprising:
a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein.

2. The phosphorylation sensing system of claim 1, wherein the first split protein fragment and the second split protein fragment are part of the bioluminescent protein selected from a luciferase and a photoprotein.

3. The phosphorylation sensing system of claim 1, wherein the first split protein fragment and the second split protein fragments are part of the bioluminescent protein selected from: *Renilla* Luciferases, portions thereof, mutants thereof, variants thereof; Coleoptera Luciferase, portions thereof, mutants thereof, variants thereof; Firefly Luciferase, portions thereof, mutants thereof, variants thereof; Gaussia Luciferase, portions thereof, mutants thereof, variants thereof; and aequorin photoproteinm Luciferase, portions thereof, mutants thereof, variants thereof.

4. The phosphorylation sensing system of claim 1, wherein the first linker peptide is rigid to separate the first split protein fragment and the second split protein fragment when the phosphorylation domain is de-phosphorylated.

5. The phosphorylation sensing system of claim 4, wherein the first linker is selected from: EAAAREAAAR (SEQ ID No. 36), EAAAREAAAREAAAR (SEQ ID No. 37), and EAAAREAAAREAAAREAAAREAAAR (SEQ ID No. 45).

6. The phosphorylation sensing system of claim 4, wherein the first split protein fragment and the second split protein fragment are adapted to self complement to substantially form the bioluminescent protein when the phosphorylation domain is phosphorylated.

7. The phosphorylation sensing system of claim 1, wherein the first split protein fragment and the second split protein fragment are adapted to self complement to substantially form the bioluminescent protein when the phosphorylation domain is not phosphorylated.

8. The phosphorylation sensing system of claim 1, wherein the substrate recognition domain includes PI3 Kinase.

9. The phosphorylation sensing system of claim 1, wherein the components of the phosphorylation sensing system include a structure in the following order: the first split protein fragment, the phosphorylation domain, the first linker peptide, the substrate recognition domain, and the second split protein fragment.

10. A kit, comprising:
a first split protein fragment, a phosphorylation domain, a first linker peptide, a substrate recognition domain, and a second split protein fragment, wherein the phosphorylation domain is attached to a first end of the first split protein fragment, wherein the substrate recognition domain is attached to the first end of the second split protein fragment, wherein a first linker peptide is attached to each of the phosphorylation domain and the substrate recognition domain, wherein the phosphorylation domain and the substrate recognition domain bind if the phosphorylation domain is phosphorylated, wherein the first split protein fragment and the second split protein fragment are not bioluminescent, and wherein the first split protein fragment and the second split protein fragment are adapted to self complement to substantially form a bioluminescent protein; and
directions for use.

11. The kit of claim 10, further comprising a bioluminescence initiating compound.

12. The kit of claim 10, wherein the first split protein fragment and the second split protein fragment are part of the bioluminescent protein selected from a luciferase or a photoprotein.

13. The kit of claim 10, wherein the first split protein fragment and the second split protein fragment are part of the bioluminescent protein selected from: *Renilla* Luciferase, portions thereof, mutants thereof, variants thereof; Coleoptera Luciferase, portions thereof, mutants thereof, variants thereof; Firefly Luciferase, portions thereof, variants thereof; Gaussia Luciferase, portions thereof, mutants thereof, variants thereof, and aequorin photoprotein Luciferase, portions thereof, mutants thereof, variants thereof.

14. The kit of claim 10, wherein the first linker peptide is rigid to separate the first split protein fragment and the second split protein fragment when the phosphorylation domain is de-phosphorylated.

15. The kit of claim 14, wherein the first linker is selected from: EAAAREAAAR (SEQ ID NO:36), EAAAREAAAR-EAAAR (SEQ ID NO:37), and EAAAREAAAREAAAR-EAAAREAAAR (SEQ ID NO:45).

16. The kit of claim 14, wherein the first split protein fragment and the second split protein fragment are adopted to self complement to substantially form the bioluminescent protein when the phosphorylation domain is phosphorylated.

17. The kit of claim 10, wherein the first split protein fragment and the second split protein fragment are adapted to self complement to substantially form the bioluminescent protein when the phosphorylation domain is phosphorylated.

18. The kit of claim 10, wherein the substrate recognition domain comprises PI3 Kinase.

19. The kit of claim 10, wherein the components of the phosphorylation sensing system include a structure in the following order: the first split protein fragment, the phosphorylation domain, the first linker peptide, the substrate recognition domain, and the second split protein fragment.

20. The kit of claim 10, wherein the phosphorylation domain is selected from "SEQ ID NO:28, SEQ ID NO:29, SEQ ID NO:31 or SEQ ID NO:32.

21. The kit of claim 10, wherein the substrate recognition domain is selected from SEQ ID NO:27, SEQ ID NOP:40, SEQ ID NO:41, SEQ ID NO:42 or SEQ ID NO;43.

22. The phosphorylation sensing system of claim 1, wherein the phosphorylation domain is selected from SEQ ID NO:28, SEQ ID NO;29, SEQ ID NO:31, or SEQ ID NO:32.

23. The phosphorylation sensing system of claim 1, wherein the substrate recognition domain is selected from SEQ ID NO:27, SEQ ID NO:40, SEQ ID NO:41, SEQ ID NO:42 or SEQ ID NO:43.

* * * * *

SEQUENCE LISTING

<160> NUMBER OF SEQ ID NOS: 47

<210> SEQ ID NO 1
<211> LENGTH: 311
<212> TYPE: PRT
<213> ORGANISM: Renilla Luciferase

<400> SEQUENCE: 1

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
            85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125
```

```
Tyr Ser Tyr Glu His Gln Asp Lys Ile Lys Ala Ile Val His Ala Glu
         130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 2
<211> LENGTH: 311
<212> TYPE: PRT
<213> ORGANISM: Renilla Luciferase

<400> SEQUENCE: 2

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190
```

```
Lys Leu Glu Pro Glu Glu Phe Ala Ala Tyr Leu Glu Pro Phe Lys Glu
        195                 200                 205
Lys Gly Glu Val Arg Arg Pro Thr Leu Ser Trp Pro Arg Glu Ile Pro
    210                 215                 220
Leu Val Lys Gly Gly Lys Pro Asp Val Val Gln Ile Val Arg Asn Tyr
225                 230                 235                 240
Asn Ala Tyr Leu Arg Ala Ser Asp Leu Pro Lys Met Phe Ile Glu
                245                 250                 255
Ser Asp Pro Gly Phe Phe Ser Asn Ala Ile Val Glu Gly Ala Lys Lys
                260                 265                 270
Phe Pro Asn Thr Glu Phe Val Lys Val Lys Gly Leu His Phe Ser Gln
                275                 280                 285
Glu Asp Ala Pro Asp Glu Met Gly Lys Tyr Ile Lys Ser Phe Val Glu
                290                 295                 300
Arg Val Leu Lys Asn Glu Gln
305                 310

<210> SEQ ID NO 3
<211> LENGTH: 1653
<212> TYPE: DNA
<213> ORGANISM: Firefly Luciferase

<400> SEQUENCE: 3
atggaagacg ccaaaaacat aaagaaaggc ccggcgccat tctatccgct ggaagatgga    60
accgctggag agcaactgca taaggctatg aagagatacg ccctggttcc tggaacaatt   120
gcttttacag atgcacatat cgaggtggac atcacttacg ctgagtactt cgaaatgtcc   180
gttcggttgg cagaagctat gaaacgatat gggctgaata caaatcacag aatcgtcgta   240
tgcagtgaaa actctcttca attctttatg ccggtgttgg gcgcgttatt tatcggagtt   300
gcagttgcgc ccgcgaacga catttataat gaacgtgaat tgctcaacag tatgggcatt   360
tcgcagccta ccgtggtgtt cgtttccaaa aagggggttgc aaaaaatttt gaacgtgcaa   420
aaaaagctcc caatcatcca aaaaattatt atcatggatt ctaaaacgga ttaccaggga   480
tttcagtcga tgtacacgtt cgtcacatct catctacctc ccggttttaa tgaatacgat   540
tttgtgccag agtccttcga tagggacaag acaattgcac tgatcatgaa ctcctctgga   600
tctactggtc tgcctaaagg tgtcgctctg cctcatagaa ctgcctgcgt gagattctcg   660
catgccagag atcctatttt tggcaatcaa atcattccgg atactgcgat tttaagtgtt   720
gttccattcc atcacggttt tggaatgttt actacactcg atatttgat atgtggattt   780 cgagtcgtct taatgtatag atttgaagaa gagctgtttc tgaggagcct tcaggattac   840
aagattcaaa gtgcgctgct ggtgccaacc ctattctcct tcttcgccaa agcactctg    900 attgacaaat acgatttatc taatttacac gaaattgctt ctggtggcgc tcccctctct   960
aaggaagtcg ggaagcggt tgccaagagg ttccatctgc aggtatcag caaggatat   1020 gggctcactg agactacatc agctattctg attacacccg aggggatga taaaccgggc   1080 gcggtcggta aagttgttcc attttttgaa gcgaaggttg tggatctgga taccgggaaa   1140
acgctgggcg ttaatcaaag aggcgaactg tgtgtgagag gtcctatgat tatgtccggt   1200
tatgtaaaca atccggaagc gaccaacgcc ttgattgaca aggatggatg gctacattct   1260
ggagacatag cttactggga cgaagacgaa cacttcttca tcgttgaccg cctgaagtct   1320
ctgattaagt acaaaggcta tcaggtggct cccgctgaat tggaatccat cttgctccaa   1380
caccccaaca tcttcgacgc aggtgtcgca ggtcttcccg acgatgacgc cggtgaactt   1440
```

```
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aggtcttac cggaaaactc gacgcaagaa aaatcagaga gatcctcata    1620
aaggccaaga agggcggaaa gatcgccgtg taa                                 1653
```

<210> SEQ ID NO 4
<211> LENGTH: 311
<212> TYPE: PRT
<213> ORGANISM: Renilla Luciferase

<400> SEQUENCE: 4

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Thr Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Ala Leu Ala Phe His
        115                 120                 125

Tyr Ala Tyr Glu His Gln Asp Arg Ile Lys Ala Ile Val His Met Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Val Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Leu Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Leu Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310
```

<210> SEQ ID NO 5
<211> LENGTH: 1428
<212> TYPE: DNA
<213> ORGANISM: Firefly Luciferase

<400> SEQUENCE: 5

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aagggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggccctt ccgcatagag ctgcctgcgt cagattctcg     660
catgccagag atcctatttt tggcaatcaa atcgctccgg atactgcgat tttaagtgtt     720
gttccattcc atcacggttt tggaatgttt actacactcg atatttgat atgtggattt     780
cgagtcgtct taatgtatag atttgaagaa gagctgtttt tacgatccct tcaggattac     840
aaaattcaaa gtgcgttgct agtaccaacc ctatttttcat tcctggccaa aagcactctg     900
attgacaaat acgatttatc taatttacac gaaattgctt ctgggggcgc acctctttcg     960
aaagaagtcg gggaagcggt tgcaaaacgc ttccatcttc cagggatacg acaaggatat    1020
gggctcactg agactacatc agctattctg attacaccca agggggatga taaaccgggc    1080
gcggtcggta aagttgttcc attttttgaa gcgaaggttg tggatctgga taccgggaaa    1140
acgctgggcg ttaatcagag aggcgaatta tgtgtcagag acctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
cacccccaaca tcttcgacgc gggcgtggca ggtcttcccg acgattaa                1428
```

<210> SEQ ID NO 6
<211> LENGTH: 475
<212> TYPE: PRT
<213> ORGANISM: Firefly Luciferase

<400> SEQUENCE: 6

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

-continued

```
Cys Ser Glu Asn Ser Leu Gln Phe Phe Met Pro Val Leu Gly Ala Leu
             85                  90                  95
Phe Ile Gly Val Ala Val Ala Pro Ala Asn Asp Ile Tyr Asn Glu Arg
            100                 105                 110
Glu Leu Leu Asn Ser Met Gly Ile Ser Gln Pro Thr Val Val Phe Val
            115                 120                 125
Ser Lys Lys Gly Leu Gln Lys Ile Leu Asn Val Gln Lys Lys Leu Pro
            130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
            195                 200                 205
Ala Leu Pro His Arg Thr Ala Cys Val Arg Phe Ser His Ala Arg Asp
            210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
            275                 280                 285
Pro Thr Leu Phe Ser Phe Phe Ala Lys Ser Thr Leu Ile Asp Lys Tyr
            290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
            370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
            450                 455                 460
Phe Asp Ala Gly Val Ala Gly Leu Pro Asp Asp
465                 470                 475
```

<210> SEQ ID NO 7
<211> LENGTH: 861
<212> TYPE: DNA
<213> ORGANISM: Firefly Luciferase

<400> SEQUENCE: 7

```
atgtatagat tgaagaaga gctgtttctg aggagccttc aggattacaa gattcaaagt    60
gcgctgctgg tgccaaccct attctccttc ttcgccaaaa gcactctgat tgacaaatac   120
gatttatcta atttacacga aattgcttct ggtggcgctc ccctctctaa ggaagtcggg   180
gaagcggttg ccaagaggtt ccatctgcca ggtatcaggc aaggatatgg gctcactgag   240
actacatcag ctattctgat tacacccgag ggggatgata aaccgggcgc ggtcggtaaa   300
gttgttccat tttttgaagc gaaggttgtg gatctggata ccgggaaaac gctgggcgtt   360
aatcaaagag gcgaactgtg tgtgagaggt cctatgatta tgtccggtta tgtaaacaat   420
ccggaagcga ccaacgcctt gattgacaag gatggatggc tacattctgg agacatagct   480
tactgggacg aagacgaaca cttcttcatc gttgaccgcc tgaagtctct gattaagtac   540
aaaggctatc aggtggctcc cgctgaattg gaatccatct tgctccaaca ccccaacatc   600
ttcgacgcag tgtcgcagg tcttcccgac gatgacgccg tgaacttcc cgccgccgtt   660
gttgttttgg agcacggaaa gacgatgacg gaaaaagaga tcgtggatta cgtcgccagt   720
caagtaacaa ccgcgaaaaa gttgcgcgga ggagttgtgt ttgtggacga agtaccgaaa   780
ggtcttaccg aaaaactcga cgcaagaaaa atcagagaga tcctcataaa ggccaagaag   840
ggcggaaaga tcgccgtgta a                                             861
```

<210> SEQ ID NO 8
<211> LENGTH: 286
<212> TYPE: PRT
<213> ORGANISM: Firefly Luciferase

<400> SEQUENCE: 8

```
Met Tyr Arg Phe Glu Glu Glu Leu Phe Leu Arg Ser Leu Gln Asp Tyr
1               5                  10                  15

Lys Ile Gln Ser Ala Leu Leu Val Pro Thr Leu Phe Ser Phe Phe Ala
            20                  25                  30

Lys Ser Thr Leu Ile Asp Lys Tyr Asp Leu Ser Asn Leu His Glu Ile
        35                  40                  45

Ala Ser Gly Gly Ala Pro Leu Ser Lys Glu Val Gly Glu Ala Val Ala
    50                  55                  60

Lys Arg Phe His Leu Pro Gly Ile Arg Gln Gly Tyr Gly Leu Thr Glu
65                  70                  75                  80

Thr Thr Ser Ala Ile Leu Ile Thr Pro Glu Gly Asp Asp Lys Pro Gly
                85                  90                  95

Ala Val Gly Lys Val Val Pro Phe Phe Glu Ala Lys Val Val Asp Leu
            100                 105                 110

Asp Thr Gly Lys Thr Leu Gly Val Asn Gln Arg Gly Glu Leu Cys Val
        115                 120                 125

Arg Gly Pro Met Ile Met Ser Gly Tyr Val Asn Asn Pro Glu Ala Thr
    130                 135                 140

Asn Ala Leu Ile Asp Lys Asp Gly Trp Leu His Ser Gly Asp Ile Ala
145                 150                 155                 160

Tyr Trp Asp Glu Asp Glu His Phe Phe Ile Val Asp Arg Leu Lys Ser
                165                 170                 175
```

-continued

Leu Ile Lys Tyr Lys Gly Tyr Gln Val Ala Pro Ala Glu Leu Glu Ser
            180                 185                 190

Ile Leu Leu Gln His Pro Asn Ile Phe Asp Ala Gly Val Ala Gly Leu
        195                 200                 205

Pro Asp Asp Asp Ala Gly Glu Leu Pro Ala Ala Val Val Val Leu Glu
    210                 215                 220

His Gly Lys Thr Met Thr Glu Lys Glu Ile Val Asp Tyr Val Ala Ser
225                 230                 235                 240

Gln Val Thr Thr Ala Lys Lys Leu Arg Gly Gly Val Val Phe Val Asp
                245                 250                 255

Glu Val Pro Lys Gly Leu Thr Gly Lys Leu Asp Ala Arg Lys Ile Arg
            260                 265                 270

Glu Ile Leu Ile Lys Ala Lys Lys Gly Gly Lys Ile Ala Val
        275                 280                 285

<210> SEQ ID NO 9
<211> LENGTH: 1194
<212> TYPE: DNA
<213> ORGANISM: Firefly Luciferase

<400> SEQUENCE: 9

```
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgggcatt     360
tcgcagccta ccgtggtgtt cgtttccaaa aagggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt     720
gttccattcc atcacggttt tggaatgttt actacactcg atatttgat atgtggattt     780
cgagtcgtct taatgtatag atttgaagaa gagctgtttc tgaggagcct tcaggattac     840
aagattcaaa gtgcgctgct ggtgccaacc ctattctcct tcttcgccaa agcactctg     900
attgacaaat acgatttatc taatttacac gaaattgctt ctggtggcgc tcccctctct     960
aaggaagtcg ggaagcggt tgccaagagg ttccatctgc aggtatcag caaggatat    1020
gggctcactg agactacatc agctattctg attacacccg aggggatga taaaccggc    1080
gcggtcggta aagttgttcc attttttgaa gcgaaggttg tggatctgga taccgggaaa    1140
acgctgggcg ttaatcaaag aggcgaactg tgtgtgagag gtcctatgat tatg         1194
```

<210> SEQ ID NO 10
<211> LENGTH: 398
<212> TYPE: PRT
<213> ORGANISM: Firefly Luciferase

<400> SEQUENCE: 10

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asp Ile Thr Tyr Ala Glu Tyr Phe Glu Met Ser Val Arg Leu Ala
50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Gly Ile Ser Gln Pro Thr Val Val Phe Val
        115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met
385                 390                 395
```

<210> SEQ ID NO 11
<211> LENGTH: 459
<212> TYPE: DNA
<213> ORGANISM: Firefly Luciferase

<400> SEQUENCE: 11

```
tccggttatg taaacaatcc ggaagcgacc aacgccttga ttgacaagga tggatggcta      60
cattctggag acatagctta ctgggacgaa gacgaacact tcttcatcgt tgaccgcctg     120
aagtctctga ttaagtacaa aggctatcag gtggctcccg ctgaattgga atccatcttg     180
ctccaacacc ccaacatctt cgacgcaggt gtcgcaggtc ttcccgacga tgacgccggt     240
gaacttcccg ccgccgttgt tgttttggag cacggaaaga cgatgacgga aaagagatc      300
gtggattacg tcgccagtca agtaacaacc gcgaaaaagt tgcgcggagg agttgtgttt     360
gtggacgaag taccgaaagg tcttaccgga aaactcgacg caagaaaaat cagagagatc     420
ctcataaagg ccaagaaggg cggaaagatc gccgtgtaa                           459
```

<210> SEQ ID NO 12
<211> LENGTH: 153
<212> TYPE: PRT
<213> ORGANISM: Firefly Luciferase

<400> SEQUENCE: 12

Met Ser Gly Tyr Val Asn Asn Pro Glu Ala Thr Asn Ala Leu Ile Asp
1               5                   10                  15

Lys Asp Gly Trp Leu His Ser Gly Asp Ile Ala Tyr Trp Asp Glu Asp
            20                  25                  30

Glu His Phe Phe Ile Val Asp Arg Leu Lys Ser Leu Ile Lys Tyr Lys
        35                  40                  45

Gly Tyr Gln Val Ala Pro Ala Glu Leu Glu Ser Ile Leu Leu Gln His
    50                  55                  60

Pro Asn Ile Phe Asp Ala Gly Val Ala Gly Leu Pro Asp Asp Asp Ala
65                  70                  75                  80

Gly Glu Leu Pro Ala Ala Val Val Val Leu Glu His Gly Lys Thr Met
                85                  90                  95

Thr Glu Lys Glu Ile Val Asp Tyr Val Ala Ser Gln Val Thr Thr Ala
            100                 105                 110

Lys Lys Leu Arg Gly Gly Val Val Phe Val Asp Glu Val Pro Lys Gly
        115                 120                 125

Leu Thr Gly Lys Leu Asp Ala Arg Lys Ile Arg Glu Ile Leu Ile Lys
    130                 135                 140

Ala Lys Lys Gly Gly Lys Ile Ala Val
145                 150

<210> SEQ ID NO 13
<211> LENGTH: 471
<212> TYPE: DNA
<213> ORGANISM: Firefly Luciferase

<400> SEQUENCE: 13

```
cctatgatta tgtccggtta tgtaaacaat ccggaagcga ccaacgcctt gattgacaag      60
gatggatggc tacattctgg agacatagct tactgggacg aagacgaaca cttcttcatc     120
gttgaccgcc tgaagtctct gattaagtac aaaggctatc aggtggctcc cgctgaattg     180
gaatccatct tgctccaaca ccccaacatc ttcgacgcag gtgtcgcagg tcttcccgac     240
gatgacgccg gtgaacttcc cgccgccgtt gttgttttgg agcacggaaa gacgatgacg     300
```

| gaaaaagaga tcgtggatta cgtcgccagt caagtaacaa ccgcgaaaaa gttgcgcgga | 360 |
| ggagttgtgt ttgtggacga agtaccgaaa ggtcttaccg gaaaactcga cgcaagaaaa | 420 |
| atcagagaga tcctcataaa ggccaagaag ggcggaaaga tcgccgtgta a | 471 |

<210> SEQ ID NO 14
<211> LENGTH: 157
<212> TYPE: PRT
<213> ORGANISM: Firefly Luciferase

<400> SEQUENCE: 14

```
Gly Pro Met Ile Met Ser Gly Tyr Val Asn Asn Pro Glu Ala Thr Asn
1               5                   10                  15

Ala Leu Ile Asp Lys Asp Gly Trp Leu His Ser Gly Asp Ile Ala Tyr
            20                  25                  30

Trp Asp Glu Asp Glu His Phe Phe Ile Val Asp Arg Leu Lys Ser Leu
        35                  40                  45

Ile Lys Tyr Lys Gly Tyr Gln Val Ala Pro Ala Glu Leu Glu Ser Ile
    50                  55                  60

Leu Leu Gln His Pro Asn Ile Phe Asp Ala Gly Val Ala Gly Leu Pro
65                  70                  75                  80

Asp Asp Asp Ala Gly Glu Leu Pro Ala Ala Val Val Val Leu Glu His
                85                  90                  95

Gly Lys Thr Met Thr Glu Lys Glu Ile Val Asp Tyr Val Ala Ser Gln
            100                 105                 110

Val Thr Thr Ala Lys Lys Leu Arg Gly Gly Val Val Phe Val Asp Glu
        115                 120                 125

Val Pro Lys Gly Leu Thr Gly Lys Leu Asp Ala Arg Lys Ile Arg Glu
    130                 135                 140

Ile Leu Ile Lys Ala Lys Lys Gly Gly Lys Ile Ala Val
145                 150                 155
```

<210> SEQ ID NO 15
<211> LENGTH: 1629
<212> TYPE: DNA
<213> ORGANISM: Coleoptera Luciferase

<400> SEQUENCE: 15

| atggtaaagc gtgagaaaaa tgtcatctat ggccctgagc tctccatcc tttggaggat | 60 |
| ttgactgccg gcgaaatgct gtttcgtgct ctccgcaagc actctcattt gcctcaagcc | 120 |
| ttggtcgatg tggtcggcga tgaatctttg agctacaagg agttttttga ggcaaccgtc | 180 |
| ttgctggctc agtccctcca caattgtggc tacaagatga cgacgtcgt tagtatctgt | 240 |
| gctgaaaaca tacccgtttt cttcattcca gtcatcgccg catggtatat cggtatgatc | 300 |
| gtggctccag tcaacgagag ctacattccc gacgaactgt gtaaagtcat gggtatctct | 360 |
| aagccacaga ttgtcttcac cactaagaat attctgaaca agtcctgga agtccaaagc | 420 |
| cgcaccaact ttattaagcg tatcatcatc ttggacactg tggagaatat tcacggttgc | 480 |
| gaatctttgc ctaatttcat ctctcgctat tcagacggca catcgcaaa ctttaaacca | 540 |
| ctccacttcg accctgtgga acaagttgca gccattctgt gtagcagcgg tactactgga | 600 |
| ctcccaaagg gagtcatgca gacccatcaa aacatttgcg tgcgtctgat ccatgctctc | 660 |
| gatccacgct acggcactca gctgattcct ggtgtcaccg tcttggtcta cttgcctttc | 720 |
| ttccatgctt tcggctttca tattactttg ggttactttt tggtcggtct ccgcgtgatt | 780 |
| atgttccgcc gttttgatca ggaggctttc ttgaaagcca tccaagatta tgaagtccgc | 840 |

```
agtgtcatca acgtgcctag cgtgatcctg tttttgtcta agagcccact cgtggacaag    900
tacgacttgt cttcactgcg tgaattgtgt tgcggtgccg ctccactggc taaggaggtc    960
gctgaagtgg ccgccaaacg cttgaatctt ccagggattc gttgtggctt cggcctcacc   1020
gaatctacca gtgcgattat ccagactctc ggggatgagt ttaagagcgg ctctttgggc   1080
cgtgtcactc cactcatggc tgctaagatc gctgatcgcg aaactggtaa ggctttgggc   1140
ccgaaccaag tgggcgagct gtgtatcaaa ggccctatgg tgagcaaggg ttatgtcaat   1200
aacgttgaag ctaccaagga ggccatcgac gacgacggct ggttgcattc tggtgatttt   1260
ggatattacg acgaagatga gcatttttac gtcgtggatc gttacaagga gctgatcaaa   1320
tacaagggta gccaggttgc tccagctgag ttggaggaga ttctgttgaa aaatccatgc   1380
attcgcgatg tcgctgtggt cggcattcct gatctgagg ccggcgaact gccttctgct   1440
ttcgttgtca agcagcctgg tacagaaatt accgccaaag aagtgtatga ttacctggct   1500
gaacgtgtga gccatactaa gtacttgcgt ggcggcgtgc gttttgttga ctccatccct   1560
cgtaacgtaa caggcaaaat tacccgcaag gagctgttga acaattgtt ggtgaaggcc   1620
ggcggttag                                                          1629

<210> SEQ ID NO 16
<211> LENGTH: 542
<212> TYPE: PRT
<213> ORGANISM: Coleoptera Luciferase

<400> SEQUENCE: 16

Met Val Lys Arg Glu Lys Asn Val Ile Tyr Gly Pro Glu Pro Leu His
1               5                   10                  15

Pro Leu Glu Asp Leu Thr Ala Gly Glu Met Leu Phe Arg Ala Leu Arg
            20                  25                  30

Lys His Ser His Leu Pro Gln Ala Leu Val Asp Val Val Gly Asp Glu
        35                  40                  45

Ser Leu Ser Tyr Lys Glu Phe Phe Glu Ala Thr Val Leu Leu Ala Gln
    50                  55                  60

Ser Leu His Asn Cys Gly Tyr Lys Met Asn Asp Val Val Ser Ile Cys
65                  70                  75                  80

Ala Glu Asn Asn Thr Arg Phe Phe Ile Pro Val Ile Ala Ala Trp Tyr
                85                  90                  95

Ile Gly Met Ile Val Ala Pro Val Asn Glu Ser Tyr Ile Pro Asp Glu
            100                 105                 110

Leu Cys Lys Val Met Gly Ile Ser Lys Pro Gln Ile Val Phe Thr Thr
        115                 120                 125

Lys Asn Ile Leu Asn Lys Val Leu Glu Val Gln Ser Arg Thr Asn Phe
    130                 135                 140

Ile Lys Arg Ile Ile Ile Leu Asp Thr Val Glu Asn Ile His Gly Cys
145                 150                 155                 160

Glu Ser Leu Pro Asn Phe Ile Ser Arg Tyr Ser Asp Gly Asn Ile Ala
                165                 170                 175

Asn Phe Lys Pro Leu His Phe Asp Pro Val Glu Gln Val Ala Ala Ile
            180                 185                 190

Leu Cys Ser Ser Gly Thr Thr Gly Leu Pro Lys Gly Val Met Gln Thr
        195                 200                 205

His Gln Asn Ile Cys Val Arg Leu Ile His Ala Leu Asp Pro Arg Tyr
    210                 215                 220
```

```
Gly Thr Gln Leu Ile Pro Gly Val Thr Val Leu Val Tyr Leu Pro Phe
225                 230                 235                 240

Phe His Ala Phe Gly Phe His Ile Thr Leu Gly Tyr Phe Met Val Gly
                245                 250                 255

Leu Arg Val Ile Met Phe Arg Arg Phe Asp Gln Glu Ala Phe Leu Lys
            260                 265                 270

Ala Ile Gln Asp Tyr Glu Val Arg Ser Val Ile Asn Val Pro Ser Val
        275                 280                 285

Ile Leu Phe Leu Ser Lys Ser Pro Leu Val Asp Lys Tyr Asp Leu Ser
    290                 295                 300

Ser Leu Arg Glu Leu Cys Cys Gly Ala Ala Pro Leu Ala Lys Glu Val
305                 310                 315                 320

Ala Glu Val Ala Ala Lys Arg Leu Asn Leu Pro Gly Ile Arg Cys Gly
                325                 330                 335

Phe Gly Leu Thr Glu Ser Thr Ser Ala Ile Ile Gln Thr Leu Gly Asp
            340                 345                 350

Glu Phe Lys Ser Gly Ser Leu Gly Arg Val Thr Pro Leu Met Ala Ala
        355                 360                 365

Lys Ile Ala Asp Arg Glu Thr Gly Lys Ala Leu Gly Pro Asn Gln Val
    370                 375                 380

Gly Glu Leu Cys Ile Lys Gly Pro Met Val Ser Lys Gly Tyr Val Asn
385                 390                 395                 400

Asn Val Glu Ala Thr Lys Glu Ala Ile Asp Asp Gly Trp Leu His
                405                 410                 415

Ser Gly Asp Phe Gly Tyr Tyr Asp Glu Asp Glu His Phe Tyr Val Val
            420                 425                 430

Asp Arg Tyr Lys Glu Leu Ile Lys Tyr Lys Gly Ser Gln Val Ala Pro
        435                 440                 445

Ala Glu Leu Glu Glu Ile Leu Leu Lys Asn Pro Cys Ile Arg Asp Val
    450                 455                 460

Ala Val Val Gly Ile Pro Asp Leu Glu Ala Gly Glu Leu Pro Ser Ala
465                 470                 475                 480

Phe Val Val Lys Gln Pro Gly Thr Glu Ile Thr Ala Lys Glu Val Tyr
                485                 490                 495

Asp Tyr Leu Ala Glu Arg Val Ser His Thr Lys Tyr Leu Arg Gly Gly
            500                 505                 510

Val Arg Phe Val Asp Ser Ile Pro Arg Asn Val Thr Gly Lys Ile Thr
        515                 520                 525

Arg Lys Glu Leu Leu Lys Gln Leu Leu Val Lys Ala Gly Gly
    530                 535                 540

<210> SEQ ID NO 17
<211> LENGTH: 558
<212> TYPE: DNA
<213> ORGANISM: Goussia Luciferase

<400> SEQUENCE: 17
atgggagtga agttctcttt tgcccttatt tgtattgctg tggccgaggc caaaccaact      60
gaaaacaatg aagatttcaa cattgtagct gtagctagca actttgctac aacggatctc     120
gatgctgacc gtggtaaatt gcccggaaaa aaattaccac ttgaggtact caaagaaatg     180
gaagccaatg ctaggaaagc tggctgcact aggggatgtc tgatatgcct gtcacacatc     240
aagtgtacac ccaaaatgaa gaagtttatc ccaggaagat gccacaccta tgaaggagac     300
aaagaaagtg cacagggagg aataggagag gctattgttg acattcctga aattcctggg     360
```

```
tttaaggatt tggaacccat ggaacaattc attgcacaag ttgacctatg tgtagactgc    420
acaactggat gcctcaaagg tcttgccaat gtgcaatgtt ctgatttact caagaaatgg    480
ctgccacaaa gatgtgcaac ttttgctagc aaaattcaag gccaagtgga caaataaag    540 ggtgccggtg gtgattaa                                                  558
```

<210> SEQ ID NO 18
<211> LENGTH: 185
<212> TYPE: PRT
<213> ORGANISM: Goussia Luciferase

<400> SEQUENCE: 18

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

Gly Lys Lys Leu Pro Leu Glu Val Leu Lys Glu Met Glu Ala Asn Ala
50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185
```

<210> SEQ ID NO 19
<211> LENGTH: 567
<212> TYPE: DNA
<213> ORGANISM: Aqueorin Photoprotein Luciferase

<400> SEQUENCE: 19

```
atgcttacat cagacttcga caacccaaga tggattggac gacacaagca tatgttcaat     60
ttccttgatg tcaaccacaa tggaaaaatc tctcttgacg agatggtcta caggcatct    120 gatattgtca tcaataacct tggagcaaca cctgagcaag ccaaacgaca caagatgct    180 gtagaagcct tcttcggagg agctggaatg aaatatggtg tggaaactga ttggcctgca    240
tatattgaag gatggaaaaa attggctact gatgaattgg agaaatacgc caaaaacgaa    300
ccaacgctca tccgtatatg gggtgatgct tgtttgata tcgttgacaa agatcaaaat    360
ggagccatta cactggatga atggaaagca tacaccaaag ctgctggtat catccaatca    420
tcagaagatt gcgaggaaac attcagagtg tgcgatattg atgaaagtgg acaactcgat    480
gttgatgaga tgacaagaca acatttagga ttttggtaca ccatggatcc tgcttgcgaa    540
aagctctacg gtggagctgt cccctaa                                        567
```

<210> SEQ ID NO 20
<211> LENGTH: 188
<212> TYPE: PRT
<213> ORGANISM: Aqueorin Photoprotein Luciferase

<400> SEQUENCE: 20

```
Met Leu Thr Ser Asp Phe Asp Asn Pro Arg Trp Ile Gly Arg His Lys
1               5                   10                  15

His Met Phe Asn Phe Leu Asp Val Asn His Asn Gly Lys Ile Ser Leu
            20                  25                  30

Asp Glu Met Val Tyr Lys Ala Ser Asp Ile Val Ile Asn Asn Leu Gly
        35                  40                  45

Ala Thr Pro Glu Gln Ala Lys Arg His Lys Asp Ala Val Glu Ala Phe
    50                  55                  60

Phe Gly Gly Ala Gly Met Lys Tyr Gly Val Glu Thr Asp Trp Pro Ala
65                  70                  75                  80

Tyr Ile Glu Gly Trp Lys Lys Leu Ala Thr Asp Glu Leu Glu Lys Tyr
                85                  90                  95

Ala Lys Asn Glu Pro Thr Leu Ile Arg Ile Trp Gly Asp Ala Leu Phe
            100                 105                 110

Asp Ile Val Asp Lys Asp Gln Asn Gly Ala Ile Thr Leu Asp Glu Trp
        115                 120                 125

Lys Ala Tyr Thr Lys Ala Ala Gly Ile Ile Gln Ser Ser Glu Asp Cys
    130                 135                 140

Glu Glu Thr Phe Arg Val Cys Asp Ile Asp Glu Ser Gly Gln Leu Asp
145                 150                 155                 160

Val Asp Glu Met Thr Arg Gln His Leu Gly Phe Trp Tyr Thr Met Asp
                165                 170                 175

Pro Ala Cys Glu Lys Leu Tyr Gly Gly Ala Val Pro
            180                 185
```

<210> SEQ ID NO 21
<211> LENGTH: 691
<212> TYPE: DNA
<213> ORGANISM: Bacterial Luciferase

<400> SEQUENCE: 21

```
atgaataaat ggaattacgg agtcttcttc gttaactttt ataataaagg ccaacaagag    60
ccatcaaaaa cgatgaataa tgcattagaa acattacgta ttattgatga agatacatct   120
atttatgatg tgattaatat tgatgaccac tatcttgtaa agaaagacag tgaagataaa   180
aagctagcgt ctttttattac actaggagaa aaactatatg tgcttgctac cagtgaaaac   240
acagttgata ttgcagcgaa atatgcatta ccgttagttt caaatgggga tatataaat   300 gaggaacgac ttaaattgtt gagttttat aatgcatccg caagtaaata taacaagaat   360
atagatttgg ttcgacacca gcttatgtta catgtcaatg ttaatgaggc agaaactgta   420 gcaaagaag aactcaaatt atatattgaa actatgtag catgtacaca gcctagtaat   480
tttaatggct cgattgatag tattattcag agtaacgtga cagggagtta taagactgt   540 ttgtcatatg tagcgaatct tgctggtaaa tttgataata ctgtggactt cttactttgt   600
tttgagtcaa tgcaagatca aaataagaaa aaatcagtaa tgatagatct taataatcaa   660
gttattaagt tccgccaaga taataatcta a                                  691
```

<210> SEQ ID NO 22
<211> LENGTH: 231
<212> TYPE: PRT
<213> ORGANISM: Bacterial Luciferase
<220> FEATURE:
<221> NAME/KEY: misc_feature
<222> LOCATION: (231)..(231)
<223> OTHER INFORMATION: Xaa can be any naturally occurring amino acid

<400> SEQUENCE: 22

Met Asn Lys Trp Asn Tyr Gly Val Phe Phe Val Asn Phe Tyr Asn Lys
1               5                   10                  15

Gly Gln Gln Glu Pro Ser Lys Thr Met Asn Asn Ala Leu Glu Thr Leu
            20                  25                  30

Arg Ile Ile Asp Glu Asp Thr Ser Ile Tyr Asp Val Ile Asn Ile Asp
        35                  40                  45

Asp His Tyr Leu Val Lys Lys Asp Ser Glu Asp Lys Lys Leu Ala Ser
    50                  55                  60

Phe Ile Thr Leu Gly Glu Lys Leu Tyr Val Leu Ala Thr Ser Glu Asn
65                  70                  75                  80

Thr Val Asp Ile Ala Ala Lys Tyr Ala Leu Pro Leu Val Phe Lys Trp
                85                  90                  95

Asp Asp Ile Asn Glu Glu Arg Leu Lys Leu Leu Ser Phe Tyr Asn Ala
            100                 105                 110

Ser Ala Ser Lys Tyr Asn Lys Asn Ile Asp Leu Val Arg His Gln Leu
        115                 120                 125

Met Leu His Val Asn Val Asn Glu Ala Glu Thr Val Ala Lys Glu Glu
    130                 135                 140

Leu Lys Leu Tyr Ile Glu Asn Tyr Val Ala Cys Thr Gln Pro Ser Asn
145                 150                 155                 160

Phe Asn Gly Ser Ile Asp Ser Ile Ile Gln Ser Asn Val Thr Gly Ser
                165                 170                 175

Tyr Lys Asp Cys Leu Ser Tyr Val Ala Asn Leu Ala Gly Lys Phe Asp
            180                 185                 190

Asn Thr Val Asp Phe Leu Leu Cys Phe Glu Ser Met Gln Asp Gln Asn
        195                 200                 205

Lys Lys Lys Ser Val Met Ile Asp Leu Asn Asn Gln Val Ile Lys Phe
    210                 215                 220

Arg Gln Asp Asn Asn Leu Xaa
225                 230

<210> SEQ ID NO 23
<211> LENGTH: 687
<212> TYPE: DNA
<213> ORGANISM: Renilla Luciferase

<400> SEQUENCE: 23
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gattttctg catggtaacg ctgcctccag ctacctgtgg     180
aggcacgtcg tgcctcacat cgagcccgtg ctagatgca tcatccctga tctgatcgga     240
atgggtaagt ccggcaagag cgggaatggc tcatatcgcc cctggatca ctacaagtac     300 ctcaccgctt ggttcgagct gctgaacctt ccaaagaaaa tcatctttgt gggccacgac     360 tgggggggctt gtctggcctt tcactactcc tacgagcacc aagacaagat caaggccatc     420
gtccatgctg agagtgtcgt ggacgtgatc gagtcctggg acgagtggcc tgacatcgag     480

```
gaggatatcg ccctgatcaa gagcgaagag ggcgagaaaa tggtgcttga gaataacttc    540
ttcgtcgaga ccatgctccc aagcaagatc atgcggaaac tggagcctga ggagttcgct    600
gcctacctgg agccattcaa ggagaagggc gaggttagac ggcctaccct ctcctggcct    660
cgcgagatcc ctctcgttaa gggaggc                                       687
```

```
<210> SEQ ID NO 24
<211> LENGTH: 229
<212> TYPE: PRT
<213> ORGANISM: Renilla Luciferase

<400> SEQUENCE: 24
```

```
Ala Ser Met Ala Ser Lys Val Tyr Asp Pro Glu Gln Arg Lys Arg Met
1               5                   10                  15

Ile Thr Gly Pro Gln Trp Trp Ala Arg Cys Lys Gln Met Asn Val Leu
            20                  25                  30

Asp Ser Phe Ile Asn Tyr Tyr Asp Ser Glu Lys His Ala Glu Asn Ala
        35                  40                  45

Val Ile Phe Leu His Gly Asn Ala Ala Ser Ser Tyr Leu Trp Arg His
    50                  55                  60

Val Val Pro His Ile Glu Pro Val Ala Arg Cys Ile Ile Pro Asp Leu
65                  70                  75                  80

Ile Gly Met Gly Lys Ser Gly Lys Ser Gly Asn Gly Ser Tyr Arg Leu
                85                  90                  95

Leu Asp His Tyr Lys Tyr Leu Thr Ala Trp Phe Glu Leu Leu Asn Leu
            100                 105                 110

Pro Lys Lys Ile Ile Phe Val Gly His Asp Trp Gly Ala Cys Leu Ala
        115                 120                 125

Phe His Tyr Ser Tyr Glu His Gln Asp Lys Ile Lys Ala Ile Val His
    130                 135                 140

Ala Glu Ser Val Val Asp Val Ile Glu Ser Trp Asp Glu Trp Pro Asp
145                 150                 155                 160

Ile Glu Glu Asp Ile Ala Leu Ile Lys Ser Glu Glu Gly Glu Lys Met
                165                 170                 175

Val Leu Glu Asn Asn Phe Phe Val Glu Thr Met Leu Pro Ser Lys Ile
            180                 185                 190

Met Arg Lys Leu Glu Pro Glu Glu Phe Ala Ala Tyr Leu Glu Pro Phe
        195                 200                 205

Lys Glu Lys Gly Glu Val Arg Arg Pro Thr Leu Ser Trp Pro Arg Glu
    210                 215                 220

Ile Pro Leu Val Lys
225
```

```
<210> SEQ ID NO 25
<211> LENGTH: 249
<212> TYPE: DNA
<213> ORGANISM: Renilla Luciferase

<400> SEQUENCE: 25
```

```
aagcccgacg tcgtccagat tgtccgcaac tacaacgcct accttcgggc cagcgacgat    60
ctgcctaaga tgttcatcga gtccgaccct gggttctttt ccaacgctat tgtcgaggga    120
gctaagaagt ccctaacac cgagttcgtg aaggtgaagg cctccactt cagccaggag    180 gacgctccag atgaaatggg taagtacatc aagagcttcg tggagcgcgt gctgaagaac    240
gagcagtaa                                                           249
```

```
<210> SEQ ID NO 26
<211> LENGTH: 82
<212> TYPE: PRT
<213> ORGANISM: Renilla Luciferase

<400> SEQUENCE: 26

Lys Pro Asp Val Val Gln Ile Val Arg Asn Tyr Asn Ala Tyr Leu Arg
1               5                   10                  15

Ala Ser Asp Asp Leu Pro Lys Met Phe Ile Glu Ser Asp Pro Gly Phe
            20                  25                  30

Phe Ser Asn Ala Ile Val Glu Gly Ala Lys Lys Phe Pro Asn Thr Glu
        35                  40                  45

Phe Val Lys Val Lys Gly Leu His Phe Ser Gln Glu Asp Ala Pro Asp
    50                  55                  60

Glu Met Gly Lys Tyr Ile Lys Ser Phe Val Glu Arg Val Leu Lys Asn
65                  70                  75                  80

Glu Gln

<210> SEQ ID NO 27
<211> LENGTH: 104
<212> TYPE: PRT
<213> ORGANISM: Synthetic

<400> SEQUENCE: 27

Asp Ala Glu Trp Tyr Trp Gly Asp Ile Ser Arg Glu Glu Val Asn Glu
1               5                   10                  15

Lys Leu Arg Asp Thr Ala Asp Gly Thr Phe Leu Val Arg Asp Ala Ser
            20                  25                  30

Thr Lys Met His Gly Asp Tyr Thr Leu Thr Leu Arg Lys Gly Gly Asn
        35                  40                  45

Asn Lys Leu Ile Lys Ile Phe His Arg Asp Gly Lys Tyr Gly Phe Ser
    50                  55                  60

Asp Pro Leu Thr Phe Ser Ser Val Val Glu Leu Ile Asn His Tyr Arg
65                  70                  75                  80

Asn Glu Ser Leu Ala Gln Tyr Asn Pro Lys Leu Asp Val Lys Leu Leu
                85                  90                  95

Tyr Pro Val Ser Lys Tyr Gln Gln
            100

<210> SEQ ID NO 28
<211> LENGTH: 13
<212> TYPE: PRT
<213> ORGANISM: Synthetic

<400> SEQUENCE: 28

Thr Glu Glu Ala Tyr Met Lys Met Asp Leu Gly Pro Gly
1               5                   10

<210> SEQ ID NO 29
<211> LENGTH: 16
<212> TYPE: PRT
<213> ORGANISM: Synthetic

<400> SEQUENCE: 29

Lys Lys His Thr Asp Asp Gly Tyr Met Pro Met Ser Pro Gly Val Ala
1               5                   10                  15
```

```
<210> SEQ ID NO 30
<211> LENGTH: 472
<212> TYPE: DNA
<213> ORGANISM: Synthetic

<400> SEQUENCE: 30
taatggtagg ttttaactt taaaaccatt gcctgacagc attattcaag aaagcctgga     60
gattcagcaa ggtgtgaatc catttttcat tggtagatcc gaggattgca attgtaaaat    120
tgaagacaat aggttgtctc gagttcattg cttcattttc aaaaagaggc atgctgtagg    180
caaaagcatg tatgaatctc cggcacaagg tttagatgat atttggtatt gccacaccgg    240
aactaacgtg agctatttaa ataataaccg catgatacag ggtacgaaat ccttttaca     300 agacggagat gaaatcaaga tcatttggga taaaaacaat aaatttgtca ttggctttaa    360
agtggaaatt aacgatacta caggtctgtt taacgaggga ttaggtatgt tacaagaaca    420
aagagtagta cttaagcaaa cagccgaaga aaagatttg gtgaaaaagt ta            472

<210> SEQ ID NO 31
<211> LENGTH: 11
<212> TYPE: PRT
<213> ORGANISM: Synthetic

<400> SEQUENCE: 31

Arg Lys Arg Asp Arg Leu Gly Thr Leu Gly Ile
1               5                   10

<210> SEQ ID NO 32
<211> LENGTH: 14
<212> TYPE: PRT
<213> ORGANISM: Synthetic

<400> SEQUENCE: 32

Arg Phe Arg Arg Phe Gln Thr Leu Lys Ile Lys Ala Lys Ala
1               5                   10

<210> SEQ ID NO 33
<211> LENGTH: 550
<212> TYPE: PRT
<213> ORGANISM: Firefly  Luciferase

<400> SEQUENCE: 33

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140
```

```
Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Lys Pro Gly Ala Val Gly Lys Val Val Pro Phe
    355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550
```

```
<210> SEQ ID NO 34
<211> LENGTH: 10
<212> TYPE: PRT
<213> ORGANISM: Protein Synthetic

<400> SEQUENCE: 34

Gly Gly Gly Gly Ser Gly Gly Gly Gly Ser
1               5                   10

<210> SEQ ID NO 35
<211> LENGTH: 10
<212> TYPE: PRT
<213> ORGANISM: Protein Synthetic

<400> SEQUENCE: 35

Ala Cys Gly Ser Leu Ser Cys Gly Ser Phe
1               5                   10

<210> SEQ ID NO 36
<211> LENGTH: 10
<212> TYPE: PRT
<213> ORGANISM: Protein Synthetic

<400> SEQUENCE: 36

Glu Ala Ala Ala Arg Glu Ala Ala Ala Arg
1               5                   10

<210> SEQ ID NO 37
<211> LENGTH: 20
<212> TYPE: PRT
<213> ORGANISM: Protein Synthetic

<400> SEQUENCE: 37

Glu Ala Ala Ala Arg Glu Ala Ala Ala Arg Glu Ala Ala Ala Arg Glu
1               5                   10                  15

Ala Ala Ala Arg
            20

<210> SEQ ID NO 38
<211> LENGTH: 20
<212> TYPE: PRT
<213> ORGANISM: Protein Synthetic

<400> SEQUENCE: 38

Ala Cys Gly Ser Leu Ser Cys Gly Ser Phe Ala Cys Gly Ser Leu Ser
1               5                   10                  15

Cys Gly Ser Phe
            20

<210> SEQ ID NO 39
<211> LENGTH: 10
<212> TYPE: PRT
<213> ORGANISM: Protein Synthetic

<400> SEQUENCE: 39

Ala Thr Ser Ala Thr Ala Thr Ser Ala Thr
1               5                   10

<210> SEQ ID NO 40
<211> LENGTH: 13
<212> TYPE: PRT
<213> ORGANISM: Protein Synthetic
```

-continued

```
<400> SEQUENCE: 40

Thr Glu Glu Ala Tyr Met Lys Met Asp Leu Gly Pro Gly
1               5                   10

<210> SEQ ID NO 41
<211> LENGTH: 16
<212> TYPE: PRT
<213> ORGANISM: Protein Synthetic

<400> SEQUENCE: 41

Lys Lys His Thr Asp Asp Gly Tyr Met Pro Met Ser Pro Gly Val Ala
1               5                   10                  15

<210> SEQ ID NO 42
<211> LENGTH: 11
<212> TYPE: PRT
<213> ORGANISM: Protein Synthetic

<400> SEQUENCE: 42

Arg Lys Arg Asp Arg Leu Gly Thr Leu Gly Ile
1               5                   10

<210> SEQ ID NO 43
<211> LENGTH: 14
<212> TYPE: PRT
<213> ORGANISM: Protein Synthetic

<400> SEQUENCE: 43

Arg Phe Arg Arg Phe Gln Thr Leu Lys Ile Lys Ala Lys Ala
1               5                   10

<210> SEQ ID NO 44
<211> LENGTH: 11
<212> TYPE: PRT
<213> ORGANISM: Protein Synthetic

<400> SEQUENCE: 44

Arg Lys Arg Asp Arg Leu Gly Ala Leu Gly Ile
1               5                   10

<210> SEQ ID NO 45
<211> LENGTH: 25
<212> TYPE: PRT
<213> ORGANISM: Protein Synthetic

<400> SEQUENCE: 45

Glu Ala Ala Ala Arg Glu Ala Ala Ala Arg Glu Ala Ala Ala Arg Glu
1               5                   10                  15

Ala Ala Ala Arg Glu Ala Ala Ala Arg
            20                  25

<210> SEQ ID NO 46
<211> LENGTH: 306
<212> TYPE: PRT
<213> ORGANISM: Firefly Luciferase

<400> SEQUENCE: 46

His Gly Phe Gly Met Phe Thr Thr Leu Gly Tyr Leu Ile Cys Gly Phe
1               5                   10                  15

Arg Val Val Leu Met Tyr Arg Phe Glu Glu Leu Phe Leu Arg Ser
            20                  25                  30

Leu Gln Asp Tyr Lys Ile Gln Ser Ala Leu Leu Val Pro Thr Leu Phe
        35                  40                  45
```

```
Ser Phe Phe Ala Lys Ser Thr Leu Ile Asp Lys Tyr Asp Leu Ser Asn
 50                  55                  60

Leu His Glu Ile Ala Ser Gly Gly Ala Pro Leu Ser Lys Glu Val Gly
 65                  70                  75                  80

Glu Ala Val Ala Lys Arg Phe His Leu Pro Gly Ile Arg Gln Gly Tyr
                 85                  90                  95

Gly Leu Thr Glu Thr Thr Ser Ala Ile Leu Ile Thr Pro Glu Gly Asp
            100                 105                 110

Asp Lys Pro Gly Ala Val Gly Lys Val Val Pro Phe Phe Glu Ala Lys
        115                 120                 125

Val Val Asp Leu Asp Thr Gly Lys Thr Leu Gly Val Asn Gln Arg Gly
130                 135                 140

Glu Leu Cys Val Arg Gly Pro Met Ile Met Ser Gly Tyr Val Asn Asn
145                 150                 155                 160

Pro Glu Ala Thr Asn Ala Leu Ile Asp Lys Asp Gly Trp Leu His Ser
                165                 170                 175

Gly Asp Ile Ala Tyr Trp Asp Glu Asp Glu His Phe Phe Ile Val Asp
            180                 185                 190

Arg Leu Lys Ser Leu Ile Lys Tyr Lys Gly Tyr Gln Val Ala Pro Ala
        195                 200                 205

Glu Leu Glu Ser Ile Leu Leu Gln His Pro Asn Ile Phe Asp Ala Gly
210                 215                 220

Val Ala Gly Leu Pro Asp Asp Ala Gly Glu Leu Pro Ala Ala Val
225                 230                 235                 240

Val Val Leu Glu His Gly Lys Thr Met Thr Glu Lys Glu Ile Val Asp
                245                 250                 255

Tyr Val Ala Ser Gln Val Thr Thr Ala Lys Lys Leu Arg Gly Gly Val
            260                 265                 270

Val Phe Val Asp Glu Val Pro Lys Gly Leu Thr Gly Lys Leu Asp Ala
        275                 280                 285

Arg Lys Ile Arg Glu Ile Leu Ile Lys Ala Lys Lys Gly Gly Lys Ile
290                 295                 300

Ala Val
305

<210> SEQ ID NO 47
<211> LENGTH: 251
<212> TYPE: PRT
<213> ORGANISM: Firefly Luciferase

<400> SEQUENCE: 47

Leu Ile Asp Lys Tyr Asp Leu Ser Asn Leu His Glu Ile Ala Ser Gly
 1               5                  10                  15

Gly Ala Pro Leu Ser Lys Glu Val Gly Glu Ala Val Ala Lys Arg Phe
             20                  25                  30

His Leu Pro Gly Ile Arg Gln Gly Tyr Gly Leu Thr Glu Thr Thr Ser
         35                  40                  45

Ala Ile Leu Ile Thr Pro Glu Gly Asp Asp Lys Pro Gly Ala Val Gly
     50                  55                  60

Lys Val Val Pro Phe Phe Glu Ala Lys Val Val Asp Leu Asp Thr Gly
 65                  70                  75                  80

Lys Thr Leu Gly Val Asn Gln Arg Gly Glu Leu Cys Val Arg Gly Pro
                 85                  90                  95

Met Ile Met Ser Gly Tyr Val Asn Asn Pro Glu Ala Thr Asn Ala Leu
            100                 105                 110
```

-continued

```
Ile Asp Lys Asp Gly Trp Leu His Ser Gly Asp Ile Ala Tyr Trp Asp
        115                 120                 125
Glu Asp Glu His Phe Phe Ile Val Asp Arg Leu Lys Ser Leu Ile Lys
        130                 135                 140
Tyr Lys Gly Tyr Gln Val Ala Pro Ala Glu Leu Glu Ser Ile Leu Leu
145                 150                 155                 160
Gln His Pro Asn Ile Phe Asp Ala Gly Val Ala Gly Leu Pro Asp Asp
                165                 170                 175
Asp Ala Gly Glu Leu Pro Ala Ala Val Val Val Leu Glu His Gly Lys
            180                 185                 190
Thr Met Thr Glu Lys Glu Ile Val Asp Tyr Val Ala Ser Gln Val Thr
        195                 200                 205
Thr Ala Lys Lys Leu Arg Gly Gly Val Val Phe Val Asp Glu Val Pro
        210                 215                 220
Lys Gly Leu Thr Gly Lys Leu Asp Ala Arg Lys Ile Arg Glu Ile Leu
225                 230                 235                 240
Ile Lys Ala Lys Lys Gly Gly Lys Ile Ala Val
                245                 250
```